(12) United States Patent
Galagan et al.

(10) Patent No.: US 11,536,685 B2
(45) Date of Patent: Dec. 27, 2022

(54) HIGH THROUGHPUT ASSAY FOR IDENTIFYING MICROBIAL REDOX ENZYMES

(71) Applicant: TRUSTEES OF BOSTON UNIVERSITY, Boston, MA (US)

(72) Inventors: James Galagan, Needham, MA (US); Uros Kuzmanovic, Brookline, MA (US); Luis Ortiz, Brookline, MA (US); Douglas Densmore, Malden, MA (US); Nicolas Shijie Shu, Levittown, NY (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/169,171

(22) Filed: Feb. 5, 2021

(65) Prior Publication Data

US 2021/0262969 A1 Aug. 26, 2021

Related U.S. Application Data

(60) Provisional application No. 62/970,997, filed on Feb. 6, 2020.

(51) Int. Cl.
*G01N 27/327* (2006.01)
*C12Q 1/00* (2006.01)
(Continued)

(52) U.S. Cl.
CPC ......... *G01N 27/3272* (2013.01); *C12Q 1/005* (2013.01); *C12Q 1/32* (2013.01); *G01N 27/3274* (2013.01); *C12N 15/52* (2013.01)

(58) Field of Classification Search
CPC .......... G01N 27/3272; G01N 27/3274; C12Q 1/005; C12Q 1/32; C12Q 1/6888;
(Continued)

(56) References Cited

U.S. PATENT DOCUMENTS 4,340,458 A 7/1982 Lerner et al.
4,436,094 A 3/1984 Cerami
(Continued)

FOREIGN PATENT DOCUMENTS

CN 102053161 A 5/2011
CN 105136885 A 12/2015
(Continued)

OTHER PUBLICATIONS

Aparicio et al., Mol. BioSyst., 2008, 804-809 (Year: 2008).*
(Continued)

*Primary Examiner* — Gurpreet Kaur
(74) *Attorney, Agent, or Firm* — Burns & Levinson LLP; Steven M. Mills

(57) ABSTRACT

Described herein are systems, assays, methods and compositions for identification of oxidase microbial redox-enzymes (MREs) specific to an analyte of interest from an environmental source. The technology relates to identification of analyte-responsive MREs that can quantify the concentration of a target analyte with high specificity and high sensitivity, for example, where the identified analyte-responsive redox-enzyme can be used to engineer an electrochemical biosensor.

21 Claims, 53 Drawing Sheets

Specification includes a Sequence Listing.

(51) Int. Cl.
*C12Q 1/32* (2006.01)
*C12N 15/52* (2006.01)

(58) Field of Classification Search
CPC .......... C12Q 1/00; C12Q 1/001; C12Q 1/004; C12Q 1/02; C12Q 1/04
See application file for complete search history.

(56) References Cited

U.S. PATENT DOCUMENTS

| | | | |
|---|---|---|---|
| 4,633,878 | A | 1/1987 | Bombardieri |
| 4,911,794 | A | 3/1990 | Parce et al. |
| 5,387,327 | A | 2/1995 | Khan |
| 5,783,056 | A | 7/1998 | Hampp et al. |
| 6,241,863 | B1 | 6/2001 | Monbouquette |
| 6,605,200 | B1 | 8/2003 | Mao et al. |
| 6,736,777 | B2 | 5/2004 | Kim et al. |
| 7,341,846 | B2 | 3/2008 | Yamaoka et al. |
| 7,794,994 | B2 | 9/2010 | Cranley et al. |
| 9,034,262 | B2 | 5/2015 | Belbruno et al. |
| 9,228,988 | B2 | 1/2016 | Belbruno |
| 9,429,536 | B2 | 8/2016 | Belbruno et al. |
| 9,820,692 | B2 | 11/2017 | Wang et al. |
| 10,024,814 | B2 | 7/2018 | Belbruno |
| 10,182,795 | B2 | 1/2019 | Heikenfeld et al. |
| 10,415,050 | B2 | 9/2019 | Liedschulte et al. |
| 10,451,598 | B2 | 10/2019 | Belbruno et al. |
| 10,646,142 | B2 | 5/2020 | Heikenfeld et al. |
| 2002/0127623 | A1 | 9/2002 | Minshull et al. |
| 2003/0027239 | A1 | 2/2003 | Schaffar |
| 2005/0043515 | A1 | 2/2005 | Brown et al. |
| 2007/0136825 | A1 | 6/2007 | Frommer et al. |
| 2008/0160625 | A1 | 7/2008 | Palleschi et al. |
| 2009/0061451 | A1 | 3/2009 | Achim et al. |
| 2009/0099434 | A1 | 4/2009 | Liu et al. |
| 2010/0218270 | A1 | 8/2010 | Xu et al. |
| 2012/0181189 | A1 | 7/2012 | Merchant |
| 2013/0172705 | A1 | 7/2013 | Petillo et al. |
| 2015/0132857 | A1 | 5/2015 | Belbruno et al. |
| 2015/0260674 | A1 | 9/2015 | Tsao |
| 2016/0370310 | A1 | 12/2016 | Belbruno et al. |
| 2018/0292341 | A1 | 10/2018 | Belbruno |
| 2019/0004005 | A1 | 1/2019 | Oja et al. |
| 2019/0195894 | A1 | 6/2019 | Galagan |
| 2020/0191740 | A1 | 6/2020 | Arduini et al. |

FOREIGN PATENT DOCUMENTS

| | | |
|---|---|---|
| CN | 110573868 A | 12/2019 |
| EP | 1845371 A1 | 10/2007 |
| EP | 1194585 B1 | 11/2008 |
| EP | 3735904 A1 | 11/2020 |
| WO | 2005/048834 A1 | 6/2005 |
| WO | 2006/091194 A1 | 8/2006 |
| WO | 2008/070274 A2 | 6/2008 |
| WO | 2009/064771 A2 | 5/2009 |
| WO | 2011/088180 A1 | 7/2011 |
| WO | 2012/034115 A1 | 3/2012 |
| WO | 2013/059534 A1 | 4/2013 |
| WO | 2017/210465 A1 | 12/2017 |
| WO | 2018/144879 A1 | 8/2018 |
| WO | 2018/202793 A2 | 11/2018 |
| WO | 2019/224628 A1 | 11/2019 |

OTHER PUBLICATIONS

Guo et al., Journal of Biomedical Optics, 2013, 106002-1 (Year: 2013).*
Wang et al., Nature Biotechnology, 2014, 473-480 (Year: 2014).*
Guzman et al., Sensors and Actuators B, 242, 2017, 95-101 (Year: 2017).*
Gabler et al. (Enzyme and Microbial Technology, 2000, 27, 605-611) (Year: 2000).*
Clarridge III, Clinical Microbiology Reviews, 2004, 840-862. (Year: 2004).*
Kneitsch et al., Applied and Enviornmental Microbiology, 2003, 1408-1416. (Year: 2003).*
Alenus et al., "Detection of L-nicotine with dissipation mode quartz crystal microbalance using molecular imprinted polymers." Physica status solidi (a) 209.5 (2012): 905-910.
Alenus et al., "Molecularly imprinted polymers as synthetic receptors forthe QCM-D-based detection of L-nicotine in diluted saliva and urine samples." Analytical and bioanalytical chemistry 405.20 (2013): 6479-6487.
Ang et al., "Study on different molecular weights of chitosan as an immobilization matrix for a glucose biosensor." PLoS One 8.8 (2013): e70597.
Antwi-Boampong et al., "A molecularly imprinted fluoral-p/polyaniline double layer sensor system for selective sensing of formaldehyde." IEEE Sensors Journal 14.5 (2014): 1490-1498.
Antwi-Boampong et al., "Detection of formaldehyde vapor using conductive polymer films." Sensors and Actuators B: Chemical 182 (2013): 300-306.
Arugula et al., "Novel trends in affinity biosensors: current challenges and perspectives." Measurement Science and Technology 25.3 (2014): 032001.
Bellin et al., "Integrated circuit-based electrochemical sensor for spatially resolved detection of redox-active metabolites in biofilms." Nature communications 5.1 (2014): 3256.
Benowitz "Cotinine as a biomarker of environmental tobacco smoke exposure." Epidemiologic reviews 18.2 (1996): 188-204.
Campanella et al., "Direct determination of nicotine in antismoking pharmaceutical products and in tobacco using an inhibition biosensor." Analytical letters 34.6 (2001): 855-866.
Carlson et al., "An automated, handheld biosensor for aflatoxin." Biosensors and Bioelectronics 14.10-11 (2000): 841-848.
Cennamo et al., "High selectivity and sensitivity sensor based on MIP and SPR in tapered plastic optical fibers forthe detection of L-nicotine." Sensors and Actuators B: Chemical 191 (2014): 529-536.
Choi et al., "Toward a generalized and high-throughput enzyme screening system based on artificial genetic circuits." ACS synthetic biology 3.3 (2014): 163-171.
Croux et al., "Development of multichannel quartz crystal microbalances for MIP-based biosensing." Physica status solidi (a) 209.5 (2012): 892-899.
Daniel "Construction of environmental libraries for functional screening of enzyme activity." Directed Molecular Evolution of Proteins: or How to Improve Enzymes for Biocatalysis (2002): 63-78.
Debon et al., "Ultrahigh-throughput screening enables efficient single-round oxidase remodelling." Nature Catalysis 2.9 (2019): 740-747.
Diaz-Gonzalez et al., "Recent advances in electrochemical enzyme immunoassays." Electroanalysis: An International Journal Devoted to Fundamental and Practical Aspects of Electroanalysis 17.21 (2005): 1901-1918.
Dzyadavych et al., "Amperometric enzyme biosensors: Past, present and future." Irbm 29.2-3 (2008): 171-180.
Egorov et al., "Horseradish peroxidase isozyme C. A comparative study of native and recombinant enzyme produced by *E. coli* transformants." Annals of the New York Academy of Sciences 721 (1994): 73-81.
El-Amrawy et al., "Are currently available wearable devices for activity tracking and heart rate monitoring accurate, precise, and medically beneficial?." Healthcare informatics research 21.4 (2015): 315-320.
Etter et al., "Saliva cotinine levels in smokers and nonsmokers." American Journal of Epidemiology 151.3 (2000): 251-258.
Fei et al., "Screening small-molecule compound microarrays for protein ligands without fluorescence labeling with a high-throughput scanning microscope." Journal of biomedical optics 15.1 (2010): 016018.
Fekry et al., "A novel electrochemical nicotine sensor based on cerium nanoparticles with anionic surfactant." RSC Advances 5.64 (2015): 51662-51671.

(56) References Cited

OTHER PUBLICATIONS

Ferrer et al., "Metagenomics for mining new genetic resources of microbial communities." Journal of molecular microbiology and biotechnology 16 1-2 (2009): 109-123.
Ferrer et al., "Interplay of metagenomics and in vitro compartmentalization." Microbial biotechnology 2.1 (2009): 31-39.
Frenzel et al., "Expression of recombinant antibodies." Frontiers in immunology 4 (2013): 217.
Geerets et al., "Optimizing the thermal read-out technique for MIP-based biomimetic sensors: Towards nanomolar detection limits." Sensors 13.7 (2013): 9148-9159.
Goiffon et al., "A rapid bioluminescence assay for measuring myeloperoxidase activity in human plasma." Nature communications 6.1 (2015): 6271.
Goodarzi et al.,"Evaluation of nicotine sensor based on copper nanoparticles and carbon nanotubes." Journal of Nanostructure in Chemistry 5.3 (2015): 237-242.
Grigorenko et al., "Recombinant horseradish peroxidase: Production and analytical applications." Biochemistry (Moscow) 80.4 (2015): 408-416.
Hammond et al., "A diffusion monitor to measure exposure to passive smoking." Environmental science & technology 21.5 (1987): 494-497.
Harrison et al., "Activity tracking: barriers, workarounds and customisation." Proceedings of the 2015 ACM International Joint Conference on Pervasive and Ubiquitous Computing. 2015.
Held "An introduction to reactive oxygen species." BioTek Instruments (2015): 1-21.
Hornsby et al., "A high through-put platform for recombinant antibodies to folded proteins." Molecular & Cellular Proteomics 14.10 (2015): 2833-2847.
Hosokowa et al., "Droplet-based microfluidics for high-throughput screening of a metagenomic library for isolation of microbial enzymes." Biosensors and Bioelectronics 67 (2015): 379-385.
Hosu et al., "Colorimetric multienzymatic smart sensors for hydrogen peroxide, glucose and catechol screening analysis." Taianta 204 (2019): 525-532.
Benowitz "Clinical pharmacology of inhaled drugs of abuse: implications in understanding nicotine dependence." NIDA Res Monogr99 (1990): 12-29.
Van Der Helm et al., "The evolving interface between synthetic biology and functional metagenomics." Nature chemical biology 14.8 (2018): 752-759.
Vigneshvar et al., "Recent advances in biosensor technology for potential applications—an overview." Frontiers in bioengineering and biotechnology 4 (2016): 11.
Wackers et al., "Array formatting of the heat-transfer method (HTM) for the detection of small organic molecules by molecularly imprinted polymers." Sensors 14.6 (2014): 11016-11030.
Wadgave et al., "Nicotine replacement therapy: an overview." International journal of health sciences 10.3 (2016): 425-435.
Wallen et al. Accuracy of heart rate watches: Implications for weight management. PLoS One, 2016. 11(5): p. e0154420.
Wang et al., "Accuracy of wrist-worn heart rate monitors." JAMA cardiology 2.1 (2017): 104-106.
Wang et al., "Low potential detection of nicotine at multiwalled carbon nanotube-alumina-coated silica nanocomposite". Electrochemistry Communications, 2009. 11(4): p. 733-735.
Woronoff et al., "Activity-Fed Translation (AFT) Assay: A New High-Throughput Screening Strategy for Enzymes in Droplets." Chembiochem 16.9 (2015): 1343-1349.
Wu et al., "A sensitive nicotine sensor based on molecularly imprinted electropolymer of o-aminophenol." Frontiers of Chemistry in China, 1.2 (2006): 183-187.
Xiao et al., "Electroanalysis of nicotine at an electroreduced carboxylated graphene modified glassy carbon electrode." Analytical methods 7.3 (2015): 1147-1153.
Xu et al., "Annual healthcare spending attributable to cigarette smoking: an update." American journal of preventive medicine 48.3 (2015): 326-333.

Xue et al., "A new strategy for smoking cessation: characterization of a bacterial enzyme for the degradation of nicotine." Journal of the American Chemical Society 137.32 (2015): 10136-10139.
Xue et al., "An enzymatic advance in nicotine cessation therapy." Chemical Communications 54.14 (2018): 1686-1689.
Yang et al., "Inhibition biosensor for determination of nicotine." Analytica chimica acta 509.2 (2004): 151-157.
Yu et al., "Complete genome sequence of the nicotine-degrading Pseudomonas putida strain S16." Journal of Bacteriology 193.19 (2011): 5541-5542.
Yu et al., "Molecular mechanism of nicotine degradation by a newly isolated strain, *Ochrobactrum* sp. strain SJY1." Applied and environmental microbiology 81.1 (2015): 272-281.
Zamojc et al., "Fluorescent probes used for detection of hydrogen peroxide under biological conditions." Critical Yeviews in analytical chemistry 46.3 (2016): 171-200.
World Health Organization "Who reporton the global tobacco epidemic 2017: Monitoring tobacco use and prevention policies." (2017): 1-135.
Balabanova et al., "Nicotine excretion by the apocrine and eccrine sweat in smokers and passive smokers." Der Hautarzt; Zeitschrift fur Dermatologie, Venerologie, und verwandte Gebiete 43.2 (1992): 73-76.
Jing et al., "Determination of nicotine in tobacco products based on mussel-inspired reduced graphene oxide-supported gold nanoparticles." Scientific reports 6.1 (2016): 29230.
Jing et al., "Electrodeposition of Au nanoparticles on poly (diallyldimethylammonium chloride) functionalized reduced graphene oxide sheets for voltammetric determination of nicotine in tobacco products and anti-smoking pharmaceuticals." RSC advances 6.31 (2016): 26247-26253.
Kamra et al., "Implementation of molecularly imprinted polymer beads for surface enhanced Raman detection." Analytical chemistry 87.10 (2015): 5056-5061.
Kintses et al., "Picoliter cell lysate assays in microfluidic droplet compartments for directed enzyme evolution." Chemistry & biology 19.8 (2012): 1001-1009.
Ko et al., "Consumer sleep technologies: a review of the landscape." Journal of clinical sleep medicine 11.12 (2015) 1455-1461.
Lam et al., "Directed evolution of APEX2 for electron microscopy and proximity labeling." Nature methods 12.1 (2015) 51-54.
Li et al., "Electrochemical sensing of nicotine using screen-printed carbon electrodes modified with nitrogen-doped graphene sheets." Journal of Electroanalytical Chemistry 784 (2017): 77-84.
Lin et al., "Functional expression of horseradish peroxidase in *E. coli* by directed evolution." Biotechnology progress 15.3 (1999): 467-471.
Lindell et al., "Transdermally administered nicotine accumulates in gastric juice." European journal of clinical pharmacology 51.3 (1996): 315-318.
Liu et al., "Detection of secondhand cigarette smoke via nicotine using conductive polymer films." nicotine & tobacco research 15.9 (2013): 1511-1518.
Liu et al., "Nicotine-degrading microorganisms and their potential applications." Applied microbiology and biotechnology 99.9 (2015): 3775-3785.
Lo et al., "The use of nano-carbon as an alternative to multi-walled carbon nanotubes in modified electrodes for adsorptive stripping voltammetry." Sensors and Actuators B: Chemical 162.1 (2012): 361-368.
Lutz et al., "Protein engineering: past, present, and future." Protein Engineering: Methods and Protocols (2018): 1-12.
Marrazza "Aptamer sensors." Biosensors (Basel) 7.1 (2017): 5.
Martell et al., "Engineered ascorbate peroxidase as a genetically encoded reporter for electron microscopy." Nature biotechnology 30.11 (2012): 1143-1148.
McGinnis et al., "Actual causes of death in the United States." JAMA 270.18 (1993): 2207-2212.
Meier et al., "Hydrogen peroxide sensors for biomedical applications." Chemosensors 7.4 (2019): 64.
Mihasan et al., "An NAD(P)H-nicotine blue oxidoreductase is part of the nicotine regulon and may protect Arthrobacter nicotinovorans

(56) References Cited

OTHER PUBLICATIONS from oxidative stress during nicotine catabolism." Applied and environmental microbiology 73.8 (2007): 2479-2485.

Mitsubayashi et al., "Bioelectronic sniffer for nicotine using enzyme inhibition." Analytica chimica acta 573 (2006): 69-74.

Moyer et al., "Simultaneous analysis of nicotine, nicotine metabolites, and tobacco alkaloids in serum or urine by tandem mass spectrometry, with clinically relevant metabolic profiles." Clinical chemistry 48.9 (2002): 1460-1471.

Turner "Biosensors: then and now." Trends in biotechnology 31.3 (2013): 119-120.

Olczuk et al., "A history of continuous glucose monitors (CGMs) in self-monitoring of diabetes mellitus." Diabetes & Metabolic Syndrome: Clinical Research & Reviews 12.2 (2018): 181-187.

Ortiz et al., ""Automating Functional Enzyme Screenings Characterization"" Poster—International Workshop on BioDesign Automation (IWBDA) conference in Berkeley, CA—Aug. 2018.

Peeters et al., "Heat-transfer-based detection of L-nicotine, histamine, and serotonin using molecularly imprinted polymers as biomimetic receptors." Analytical and bioanalytical chemistry 405.20 (2013): 6453-6460.

Popovic et al., "Activity screening of environmental metagenomic libraries reveals novel carboxylesterase families." Scientific reports 7.1 (2017): 44103.

Rezende et al., "Detection of hydrogen peroxide with fluorescent dyes." Antioxidants & redox signaling 29.6 (2018): 585-602.

Rice et al., "Nursing interventions for smoking cessation." Cochrane database of systematic reviews 12 (2017): CD001188.

Richter et al., "Characterization of functional states in nicotine-and cotinine-imprinted poly (4-vinylphenol) films by nanoindentation." Journal of applied polymer science 124.4 (2012): 2798-2806.

Roelofs et al., "Differential radial capillary action of ligand assay for high-throughput detection of protein-metabolite interactions." Proceedings of the National Academy of Sciences 108.37 (2011): 15528-15533.

Russell et al., "Relation of nicotine yield of cigarettes to blood nicotine concentrations in smokers." British Medical Journal 280. 6219 (1980): 972-976.

Sanders et al., "Devices for self-monitoring sedentary time or physical activity: A scoping review." Journal of Medical Internet Research 18.5 (2016): e90.

Shakleya et al., "Simultaneous and sensitive measurement of nicotine, cotinine, trans-3'-hydroxycotinine and norcotinine in human plasma by liquid chromatography-tandem mass spectrometry." Journal of Chromatography B 877.29 (2009): 3537-3542.

Shehata et al., "Nano-TiO2 modified carbon paste sensor for electrochemical nicotine detection using anionic surfactant." Biosensors and Bioelectronics 79 (2016): 589-592.

Shiwaku et al., "A printed organic circuit system for wearable amperometric electrochemical sensors." Scientific reports 8.1 (2018): 6368.

Sims et al., "Effects of thin-layer diffusion in the electrochemical detection of nicotine on basal plane pyrolytic graphite (BPPG) electrodes modified with layers of multi-walled carbon nanotubes (MWCNT-BPPG)." Sensors and Actuators B: Chemical, 2010. 144(1): 153-158.

Šmajs et al., "Construction of small genome BAC library for functional and genomic applications." Methods in Molecular Biology, vol. 255: Bacterial Artificial Chromosomes, vol. 1:Library Construction, Physical Mapping, and Sequencing. Humana Press, 2004: 47-56.

Steinberg et al., "A wireless potentiostat for mobile chemical sensing and biosensing." Taianta 143 (2015): 178-183.

Švorc et al., "Boron-doped diamond electrochemical sensor for sensitive determination of nicotine in tobacco products and anti-smoking pharmaceuticals." Diamond and Related Materials 42 (2014): 1-7.

Tabassum et al., "Simultaneous tuning of electric field intensity and structural properties of ZnO: graphene nanostructures for FOSPR based nicotine sensor." Biosensors and Bioelectronics 91 (2017): 762-769.

Tan et al., "A study of a new TSM bio-mimetic sensor using a molecularly imprinted polymer coating and its application for the determination of nicotine in human serum and urine." Bioelectrochemistry 53.2 (2001): 141-148.

Tang et al., "A novel gene, encoding 6-hydroxy-3-succinoylpyridine hydroxylase, involved in nicotine degradation by Pseudomonas putida strain S16."Applied and environmental microbiology 74.5 (2008): 1567-1574.

Tang et al., "Genomic analysis of Pseudomonas putida: Genes in a genome island are crucial for nicotine degradation." Scientific reports 2.1 (2012): 377.

Tang et al., "Novel nicotine oxidoreductase-encoding gene involved in nicotine degradation by Pseudomonas putida strain S16." Applied and environmental microbiology 75.3 (2009): 772-778.

Tang et al., "Systematic unraveling of the unsolved pathway of nicotine degradation in Pseudomonas." PLoS Genetics 9.10 (2013): e1003923.

Tao et al., "Epidemiological perspectives of diabetes." Cell biochemistry and biophysics 73.1 (2015): 181-185.

Tararina et al., "Crystallography coupled with kinetic analysis provides mechanistic underpinnings of a nicotinedegrading enzyme." Biochemistry 57.26 (2018): 3741-3751.

Tararina et al., "Structural Analysis Provides Mechanistic Insight into Nicotine Oxidoreductase from Pseudomonas putida." Biochemistry 2016, 55 (48), 6595-6598.

Teepoo et al., "Electrospun chitosan-gelatin biopolymer composite nanofibers for horseradish peroxidase immobilization in a hydrogen peroxide biosensor." Biosensors 7.4 (2017): 47.

Thisted et al., "Optimization of a nicotine degrading enzyme for potential use in treatment of nicotine addiction." BMC biotechnology 19.1 (2019): 56.

Uchiyama et al., "Substrate-induced gene-expression screening of environmental metagenome libraries for isolation of catabolic genes." Nature biotechnology 23.1 (2005): 88-93.

Catcott et al., "Identifying Unknown Enzyme-Substrate Pairs from the Cellular Milieu with Native Mass Spectrometry," Chembiochem., 18(7):613-617 (2017).

Liu et al., "How to achieve high-level expression of microbial enzymes," Bioengineered, vol. 4, Issue 4, pp. 212-223, Jul./Aug. 2013.

International Search Report and Written Opinion for International Application No. PCT/US21/16870 dated Dec. 10, 2021.

Martell et al., "Engineered ascorbate peroxidase as a genetically encoded reporter for electron microscopy," Nature Biotechnology 10(11):1143-1151 (2012).

Martell et al., Supplementary Information "Engineered ascorbate peroxidase as a genetically encoded reporter for electron microscopy," Nature Biotechnology (2012).

Lin et al., "Functional Expression of Horseradish Peroxidase in E.coli by Directed Evolution," Biotechnol. Prog., 15:467-471 (1999).

Lam et al., "Directed evolution of APEX2 for electron microscopy and proximity labeling," Nature Methods, 12(1):51-61 (2015).

Lam et al., "Supplementary Discussion: Mechanistic Investigation of APEX2," Nature Methods, (2015).

Egorov et al., "Horseradish Peroxidase Isozyme C," Annals New York Academy of Sciences, pp. 73-81 (1994).

Grigorenko et al., "Recombinant Horseradish Peroxidase: Production and Analytical Applications," Biochemistry, 80(4):408-416 (2015).

Choi et al., "Single-cell, real-time detection of oxidative stress induced in *Escherichia coli* by the antimicrobial peptide DM15," PNAS, E303-E310, Jan. 5, 2015.

* cited by examiner

Oxidase:

Electrochemical Detection (1st Generation)

Electrochemical Detection (2nd Generation)

Electrochemical Detection (3rd Generation)

Non-Electrochemical Detection

Electrochemical Detection (2nd Generation)

Electrochemical Detection (3rd Generation)

Non-Electrochemical Detection

Electrochemical Detection (2nd Generation)

Electrochemical Detection (3rd Generation)

Non-Electrochemical Detection

FIG. 7B
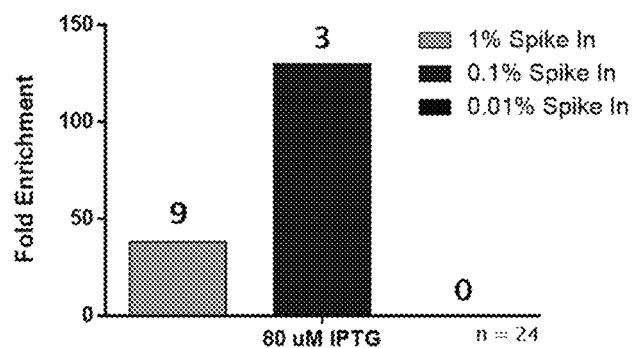
FIG. 7C
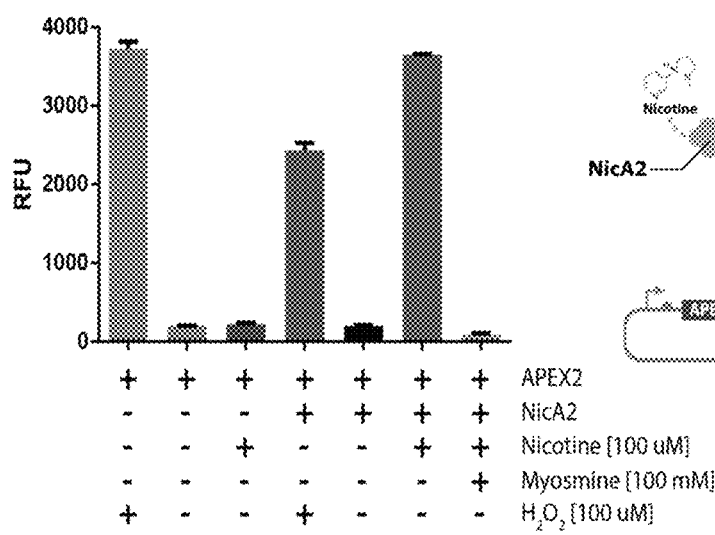
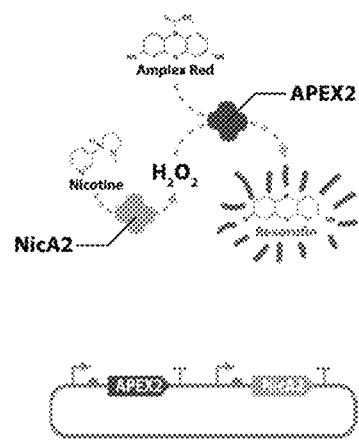

Cells expressing *apex2* and *nicA2* generate a nicotine-dependent fluorescent signal in the presence of AUR

Optimized PCR product fragmentation

NGS can be used to track enrichment

Old metagenomic library vector design

Old metagenomic library vector design

Old metagenomic library is functional

New metagenomic library is functional

FIG. 19
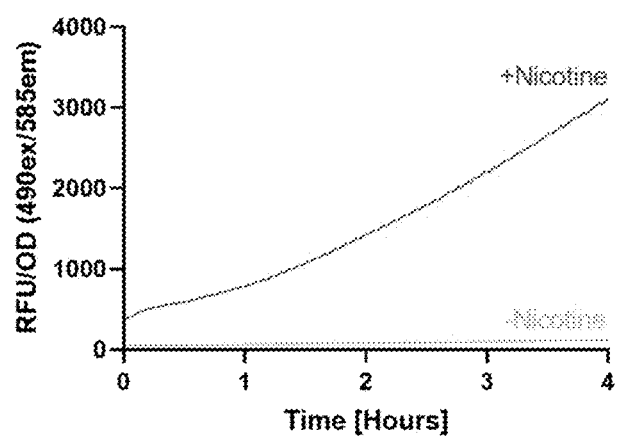
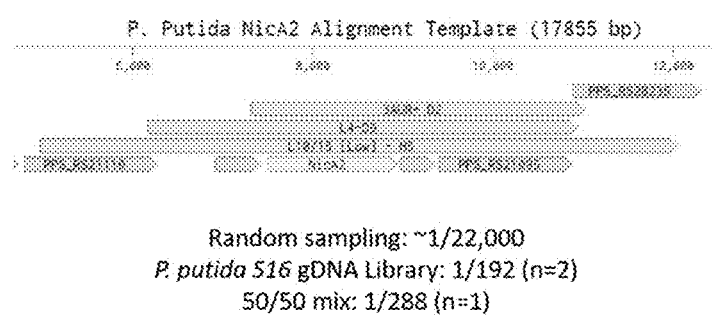
Random sampling: ~1/22,000
P. putida 516 gDNA Library: 1/192 (n=2)
50/50 mix: 1/288 (n=1)

Cell-Based Expression

Cell Free Protein Synthesis

FIG. 29A
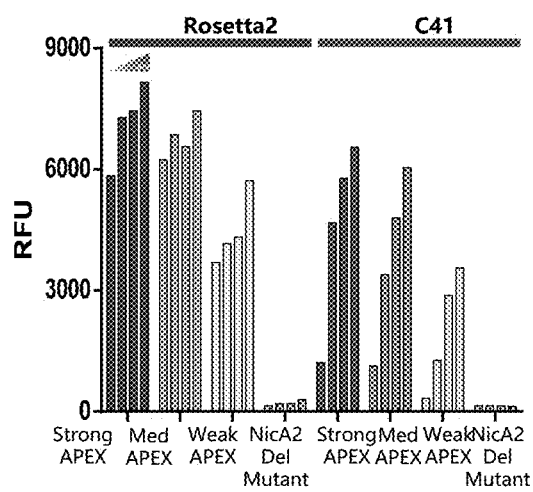
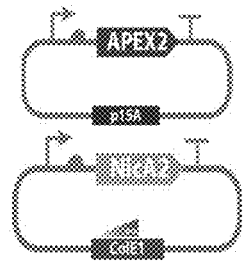
- Cells grown overnight:
    1. Uninduced
    2. 10 uM IPTG
    3. 20 uM IPTG
    4. 50 uM IPTG
- Resuspended in PBS + 50 uM Amplex Ultra Red + 1 mM Nicotine
- Incubated for 6 hours at 37°C
FIG. 29B
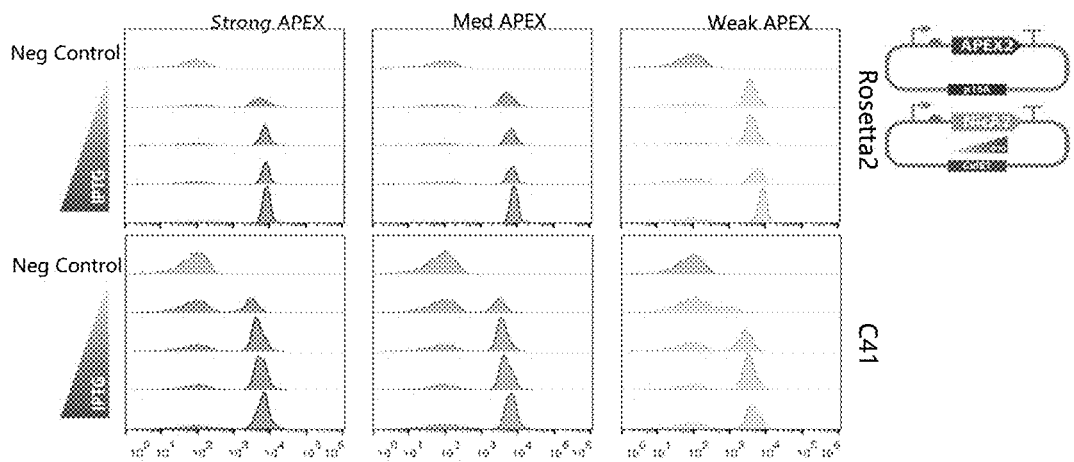

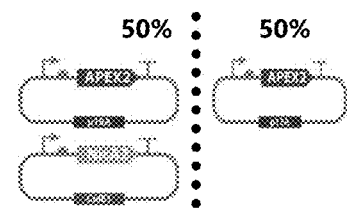
FIG. 30A
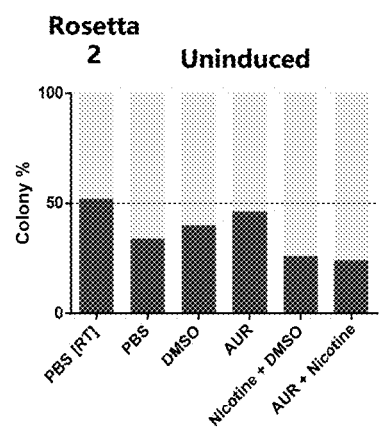
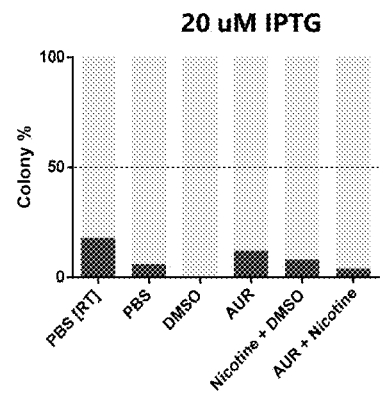
FIG. 30B
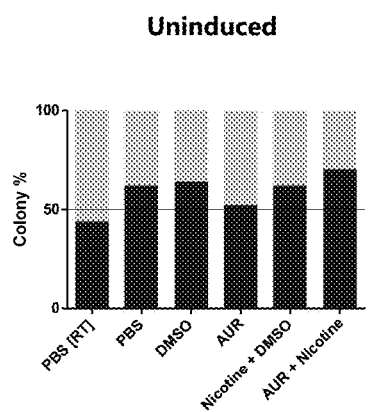
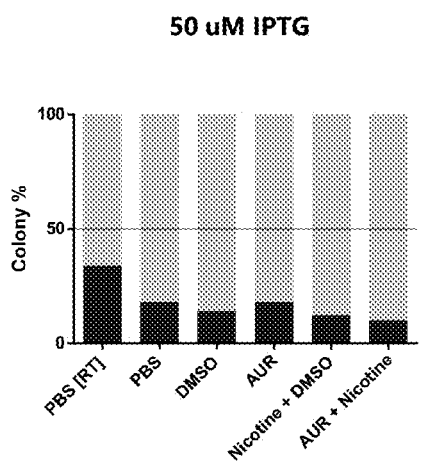

FIG. 33A  Fluorescent cells have decreased viability post-sort
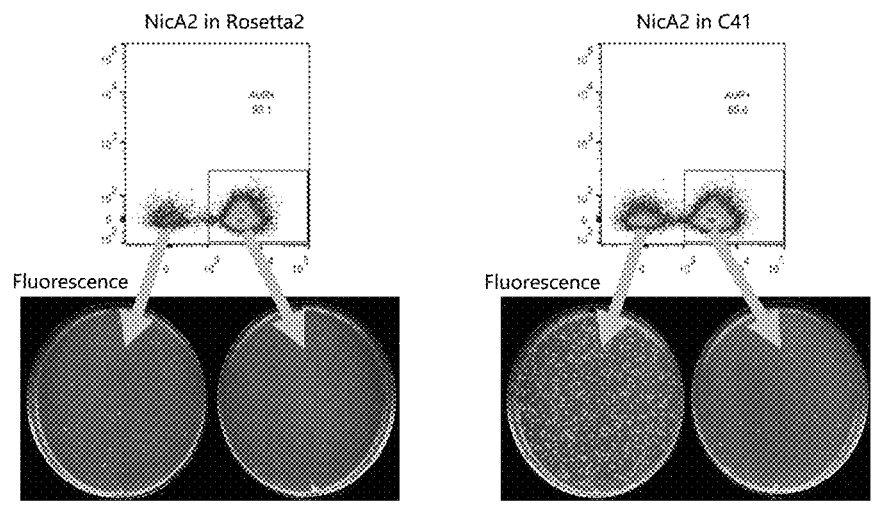
FIG. 33B
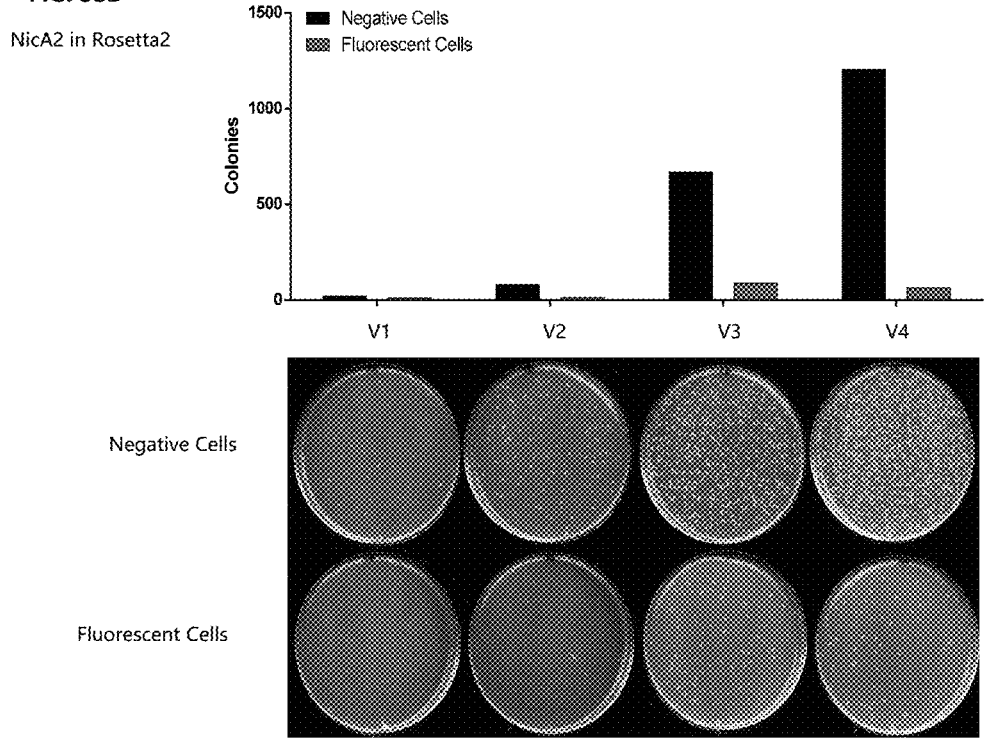

FIG. 35A

Fluorescent activity linked to reduced cell viability

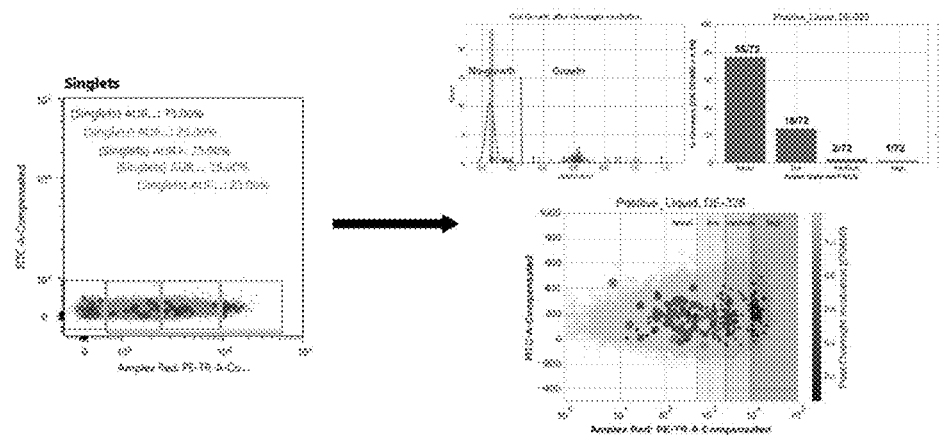

FIG. 35B

Investigating which FACS and assay variables impact cell viability

- Analyte toxicity
  - Direct exposure to nicotine, H2O2, resorufin
- Presence of antioxidants
- Treatment media
  - PBS vs. 2xYTP
- FACS sorting modes
  - Purity levels, criteria for indexing
- FACS chip nozzle width
  - 70, 100, or 130 µm
- Anaerobic vs. aerobic incubation
- Post-sort media
  - Liquid vs. Agar
- Post-sort media temperature
  - 4C, RT, 37C

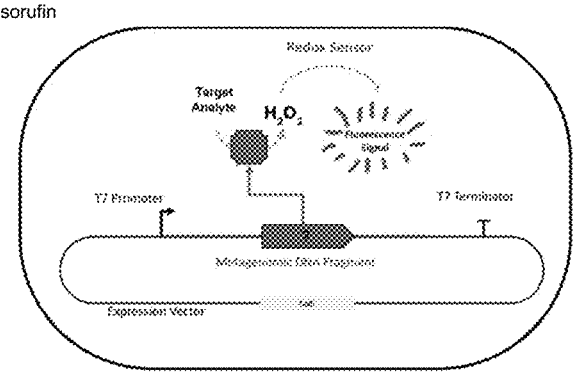

FIG. 37

Rosetta2 Cells
[1 mM Substrates + 5 uM AUR]

SEQUENCE LISTING

<160> NUMBER OF SEQ ID NOS: 1

<210> SEQ ID NO 1
<211> LENGTH: 305
<212> TYPE: PRT
<213> ORGANISM: Escherichia coli

<400> SEQUENCE: 1

```
Met Asn Ile Arg Asp Leu Glu Tyr Leu Val Ala Leu Ala Glu His Arg
1               5                   10                  15
His Phe Arg Arg Ala Ala Asp Ser Cys His Val Ser Gln Pro Thr Leu
                20                  25                  30
Ser Gly Gln Ile Arg Lys Leu Glu Asp Glu Leu Gly Val Met Leu Leu
            35                  40                  45
Glu Arg Thr Ser Arg Lys Val Leu Phe Thr Gln Ala Gly Met Leu Leu
        50                  55                  60
Val Asp Gln Ala Arg Thr Val Leu Arg Glu Val Lys Val Leu Lys Glu
65                  70                  75                  80
Met Ala Ser Gln Gln Gly Glu Thr Met Ser Gly Pro Leu His Ile Gly
                85                  90                  95
Leu Ile Pro Thr Val Gly Pro Tyr Leu Leu Pro His Ile Ile Pro Met
                100                 105                 110
Leu His Gln Thr Phe Pro Lys Leu Glu Met Tyr Leu His Glu Ala Gln
            115                 120                 125
Thr His Gln Leu Leu Ala Gln Leu Asp Ser Gly Lys Leu Asp Cys Val
    130                 135                 140
Ile Leu Ala Leu Val Lys Glu Ser Glu Ala Phe Ile Glu Val Pro Leu
145                 150                 155                 160
Phe Asp Glu Pro Met Leu Leu Ala Ile Tyr Glu Asp His Pro Trp Ala
                165                 170                 175
Asn Arg Glu Cys Val Pro Met Ala Asp Leu Ala Gly Glu Lys Leu Leu
                180                 185                 190
Met Leu Glu Asp Gly His Cys Leu Arg Asp Gln Ala Met Gly Phe Cys
            195                 200                 205
Phe Glu Ala Gly Ala Asp Glu Asp Thr His Phe Arg Ala Thr Ser Leu
        210                 215                 220
Glu Thr Leu Arg Asn Met Val Ala Ala Gly Ser Gly Ile Thr Leu Leu
225                 230                 235                 240
Pro Ala Leu Ala Val Pro Pro Glu Arg Lys Arg Asp Gly Val Val Tyr
                245                 250                 255
Leu Pro Cys Ile Lys Pro Glu Pro Arg Arg Thr Ile Gly Leu Val Tyr
                260                 265                 270
Arg Pro Gly Ser Pro Leu Arg Ser Arg Tyr Glu Gln Leu Ala Glu Ala
            275                 280                 285
Ile Arg Ala Arg Met Asp Gly His Phe Asp Lys Val Leu Lys Gln Ala
    290                 295                 300
Val
305
```

HIGH THROUGHPUT ASSAY FOR IDENTIFYING MICROBIAL REDOX ENZYMES

CROSS-REFERENCE TO RELATED APPLICATION

This application claims benefit under 35 U.S.C. § 119(e) of U.S. Provisional Application No. 62/970,997 filed Feb. 6, 2020, the contents of which is incorporated herein in its entirety by reference.

GOVERNMENT SUPPORT

This invention was made with Government Support under Contract No. W911NF-16-C-0044 awarded by the Army Research Office and Contract No. 1522074 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 25, 2021, is named 701586-094120USPT_SL.txt and is 2,987 bytes in size.

TECHNICAL FIELD

The technology described herein relates to compositions, systems, assays and methods for identification of microbial redox enzymes (MRE), including oxidases, oxidoreductases, dehydrogenases etc. which can be used as a redox enzyme biorecognition element in a biosensor for the detection of analytes and small molecules in solution and aerosolized in the air.

BACKGROUND

There is significant need to measure the presence and concentration of molecules (hormones, toxins, etc.) in complex samples, for example, blood, saliva, sweat, drinking water, etc. and in real-time.

Biosensors are a type of analytical device that use biological molecules to monitor biorecognition events and interactions. Coupled to the progress in nanotechnologies over recent years, the development of a nanobiosensor based on individual nanoelectrodes and nanoelectrode arrays or nanoelectrode ensembles offers unprecedented avenues for screening and detection at ultrahigh sensitivities. These capabilities provide the basis for a paradigmatic change in biomedical diagnostics and treatment. The ability to monitor biorecognition events and interactions on platforms offers pathways to the application of biological macromolecules as detectors. Coupled with the ability to produce conductive elements precisely on the nanoscale, biosensing offers unprecedented opportunities for screening and detection at increasing sensitivities. Recent progress in nanotechnology has enabled the development of highly sensitive nanobiosensors.

Label-free sensing of small molecules and analytes is of critical importance to biomedical research, point of care diagnostics, and environmental sensing, among other applications. Label-free sensors directly detect small molecules and analytes in samples without the need for additional sample preparation (i.e., sample purification or analyte labeling), enabling high-throughput measurements on native samples. Traditional methods and approaches to label-free biosensing utilize aptamers or antibodies as molecularly specific recognition elements. While the use of monoclonal antibodies is ubiquitous in many aspects of biomedical research and clinical treatment, it has significant drawbacks in the cost and effort required for development and production in a biosensor device, as well as challenges related to developing antibodies for small molecules. Aptamers refer to nucleic acid-based affinity probes that have been developed for protein targets and small molecules. While aptamers are considered to be more effective than antibodies at recognizing small molecule targets, the identification of aptamer sequences is significantly technically challenging for small molecule targets. Most critically, while both antibodies and aptamers provide a specific binding element, there is no inherent transduction mechanism, i.e., there is no change to the aptamer or antibody upon target binding that can be harnessed for signal output other than the binding itself.

Existing biosensor designs outside of electrochemical ones have noticeable limitations. The most common design utilizes a biorecognition element coupled to a physicochemical transduction mechanism (see e.g., Turner, A., Trends in Biotechnology 2013, 31 (3), 119-120; Mary et al., Measurement Science and Technology 2014, 25 (3), 032001; Evtugyn, G., Biosensors: Essentials. Springer: 2014; Vol. 84). The gold standard for clinical relevant analytes use antibodies as this biorecognition element. However, antibodies suffer from several important shortcomings: 1) Traditionally, antibody production requires animal immunization followed by monoclonal isolation and is expensive, highly variable, time consuming, and challenging with small molecule analytes (see e.g., Mary et al. 2014, supra). More recent recombinant techniques simplify this process and improve reproducibility, but the process remains expensive due to the use of mammalian cell lines or heterologous hosts (see e.g., Frenzel, et al. Frontiers in immunology 2013, 4, 217; Hornsbyet al. Molecular & cellular proteomics: MCP 2015, 14 (10), 2833-47). 2) Binding of the analyte to the antibody leads to only a small physicochemical change, requiring the use of a secondary assay to detect the binding event (see e.g., Mary et al. 2014, supra; az-Gonzale et al. Electroanalysis 2005, 17 (21)). Enzyme-linked immunosorbent assays (ELISAs) are the most common transduction approach and are multistep, labor-intensive, time-consuming, and not well-suited for integration into wearable technology (see e.g., az-Gonzale et al. 2005, supra). More recently, aptamers have been studied as an alternative to antibodies, but also lack an intrinsic transduction mechanism (see e.g., Mary et al. 2014, supra; Marrazza, G., Aptamer Sensors. Biosensors (Basel) 2017, 7 (1)). Due to these limitations, non-electrochemical biosensors often are suboptimal design choices for physiological monitoring.

Current commercial blood glucose tests rely on redox enzymes which convert biological signals, i.e., glucose concentration into electrical signals (i.e., electrons) that can be read by an electronic device in real-time. Specific glucose metabolizing redox enzymes in a biosensor device can be used to measure of blood glucose levels using, for example, a finger prick tests or skin patches, and are available at local pharmacies. Compared to traditional measurement techniques, biosensors have significant advantages, which include the reduced to the size of devices, the requirement of only small amounts of sample and reagents, high specificity and high sensitivity. Electrochemical biosensors have received much attention in the field of biosensing because they provide a simple, inexpensive and accurate platform for the measurement of the target analyte. Electrochemical biosensors determine the analyte level by detecting the changes in either potential, current, capacitance, conductance or impedance caused by a specific biorecognition reaction.

The advent of rapid, facile sensing is changing our daily lives and empowering clinical decision making. The Fitbit and Apple Watch for monitoring pH, hydration, temperature, heart rate, oxygen, etc., and the glucose sensor for managing type 2 diabetes are prime examples. Surprisingly, enzymatic electrochemical based sensors are few in number and limited in analyte scope (e.g., glucose, fructose, lactate, glutamate, lysine, ethanol), despite the fact that the glucose sensor was developed approximately 60 years ago. Given the interest in sensing varied analytes for applications in medicine, health/nutrition, agriculture, and environmental management, there are significant efforts ongoing to develop new sensor designs and diagnostic technologies both for single use detection and for continuous monitoring.

However, despite the commercial success of the blood glucose meter, there are limited other biosensors using redox enzymes to detect concentration of molecules in real-time, from multiple different sample sources, are reusable, and/or detect low level of an analyte that can be used for use in a point of care device.

Moreover, while methods to identify enzymes for biosensors are based on functional assays from metagenomic samples have been reported, the use of such methods are limited for numerous reasons, including the fact that the methods do not allow identification of a redox enzyme for any given target analyte, the requirement of plating techniques which require excessive amounts of time in order to sift through all possible gDNA fragments [1, 2]. Functional assays which are high-throughput often require the use of specialized or expensive equipment in order to run which limits their use [3, 4]. However, two high-throughput droplet based GFP-circuit screens for enzymes were reported with the first called AFT [5] and the other termed SIGEX [6]. A more general gene-circuit approach close to our current protocol has been reported [7]. A radiation based semi-high-throughput approach has also been reported [8]. Droplet-based high-throughput screening has also been reported [9-11]. Finally, a gene-circuit droplet based high-throughput assay, has been reported [12]. Due to such limitations, there needs a quick, reliable and efficient method to identify redox enzymes that catalyzes a specific target analyte that can be used in biosensor device.

Bacteria have evolved over 3 billion years to detect and respond to virtually all classes of stimuli relevant to our own biology. Thus, the evolution of bacterial enzymes, particularly redox enzymes for the recognition and metabolism of a multitude of physiologically relevant analytes has already been performed by nature. A high-throughput assay to identify naturally occurring microbial redox enzymes has not been described is therefore highly valuable in the development of robust electrochemical biosensors. Once useful redox enzymes are identified, if the enzymes are not selective, sensitive, fast, or stable as desired, directed evolution can be used to improve them (see e.g., Lutz, S.; Iamurri, S. M., Protein Engineering: Past, Present, and Future. In Protein Engineering, Springer: 2018; pp 1-12). However, while a cell-free assay to detect redox enzyme has been reported (Debon et al., Nat Catalysis, 2019; (2) 740-747), such an assay is not suitable for detection of redox enzymes from large metagenomic libaries or for cell-based systems. Accordingly, an efficient cell-based assay for identifying microbial redox enzymes (MREs) from environmental sources and microbiomes for use in real-time, quick sensitive and reliable analyte detection, has not yet been established.

Accordingly, there is a need in the art for high throughout methods for identifying redox enzymes, such as microbial redox enzymes, for use as biorecognition elements in biosensor devices which can be used in biosensors for detecting analytes and small molecules, including hormones.

SUMMARY

Physiologically relevant wearable sensors are in increasingly high demand, yet existing sensors are severely limited in the number and type of analyte they can detect. The lack of molecular sensing parts specifically is prohibiting the development of the next generation of biosensors. To overcome this challenge, the inventors have developed a system, method and assay to identify microbial redox enzymes (MRE's) that can be used as an enzymatic sensor part for use in a biosensor for a virtually unlimited number of analytes.

Accordingly, the technology described herein relates to assays, methods, and systems to identify a microbial redox enzyme, also referred to herein as "MRE", that can be used as an analyte-detecting enzyme in a biosensor for the accurate, reliable and sensitive measurement of an analyte of interest in an environmental, industrial, or clinical setting. Provided herein are methods of identifying microbial redox enzymes from environmental sources for detecting analytes, e.g., in fluids and in the environment. In particular, the technology described herein relates to assays, methods, and systems to identify oxidase MREs. In some embodiments, the assay can be modified by persons of ordinary skill in the art to identify MREs, where the MRE can be used in a redox reaction to produce $H_2O_2$, which can be detected using the assay disclosed herein.

Current physiological sensors on the market such as the Fitbit™ and Apple Watch™ are limited to the detection of pH, hydration, temperature, heart rate, UX index, oxygen, sleep health, and energy expenditure with limited accuracy and reproducibility. Presently, the single best example of a commercially successful enzymatic biosensor is the glucose biosensor which has existed for approximately 60 years and has in the past two decades evolved into the continuous glucose monitor (CGM; see e.g., Olczuk et al. Diabetes Metab Syndr 2018, 12 (2), 181-187). By 2004, the glucose biosensor was responsible for about 85% of the world market for biosensors, estimated to be $5 billion USD at the time. By 2015, the market for glucose biosensors was valued at $15.3 billion USD and is expected to surpass $31 billion USD by 2024 per Hexa Research. The glucose monitor's functionality is based on the isolation and use of a glucose oxidase ($GO_X$) enzyme from *Aspergillus niger*, a fungus. Specifically, the ability of $GO_X$ to produce $H_2O_2$ from β-D-glucose and oxygen has been used to engineer the first glucose biosensor in an electrochemical fashion. With a mediator and a three-electrode system, $H_2O_2$ generated from $G_X$ in response to β-D-glucose, along with a constant electrical potential, produces current which can be used as a readout for the amount of β-D-glucose present in solution.

Even with the immense commercial success of the glucose biosensor, comparable enzymatic biosensors have been limited. By 2007, commercially available enzyme based clinical tests could detect only glucose, lactate, choline, urea, uric acid, lysine, and oxygen. By 2008, amperometric based biosensors solely included those for glucose ($GO_X$), fructose (FDH), lactate ($LO_X$), glutamate ($LGO_X$), lysine (LDH), ethanol (ADH), and morphine (MDH) (see e.g., Dzyadevych et al. Irbm 2008, 29 (2-3), 171-180). The reason for the lack of a wide variety of biosensors is primarily due to two reasons. Of the seven biosensors listed, few have daily physiological relevance. The exception is the glucose biosensor due to diabetes affecting 382 million people and being the 8$^{th}$ leading cause of death worldwide by 2013 which naturally created a large market and need for such a sensor. The second reason is that the current largest scientific vendors, such as Sigma-Aldrich™, have a limited inventory of enzymes such as $GO_X$, $LO_X$, FDH, $LGO_X$, and ADH with little intention of investing resources to provide new electrochemically relevant ones.

In response to the lack of electrochemical biosensors, the inventors herein have developed a high-throughput screening assay to identify microbial redox-enzymes (MREs) from a variety of different environmental samples or sources. In particular, the inventors are able to use the assay to mine an unexplored reservoir of MREs in bacteria for use as biorecognition elements in biosensors. Bacteria have evolved over 3 billion years to detect and respond to virtually all classes of stimuli relevant to human physiology, and thus are ideal as a source to identify and isolate potential redox-enzymes that can be used as molecular sensing enzymes (also referred to as biorecognition elements) of an analyte of interest. The technology described herein relates to a functional microbial redox enzyme assay, referred to herein as the "MRE assay" which produces a detectable signal, e.g., fluorescence, (such as, e.g., AMPLEX™ UltraRed) in the presence of hydrogen peroxide, and have identified and isolated a number of biosensing oxidase enzymes. A wide number of hydrogen peroxide dependent probes are encompassed to be used in the MRE assay disclosed herein, where the $H_2O_2$-dependent probes produce a detectable signal that is proportional to the amount of target analyte catalyzed by the candidate MRE. $H_2O_2$-dependent probes can be enzyme dependent (e.g., dependent on a readout enzyme as disclosed herein), or enzyme-independent (e.g., boronate and non-boronate probes as disclosed herein. Additionally, while the MRE assay exemplified herein and in the Examples identifies oxidases, it can readily be adapted by an ordinary skilled artisan to identify a variety of different microbial redox-enzymes, including but not limited to dehydrogenases, NAD (P)-dehydrogenases, NAD(P)-independent dehydrogenases and the like, from environmental samples and/or bacterial cultures and where the identified MREs are specific for, and catalyze a physiologically relevant analyte. For example, one can modify the MRE assay disclosed herein so a dehydrogenase or other redox enzyme can catalyze a redox reaction to directly or indirectly produce hydrogen peroxide, and thus the $H_2O_2$-dependent probe or readout substrates (ReadS) disclosed herein can be used to identify such a dehydrogenase MRE etc. In the Examples herein, the MRE assay described herein has been characterized and optimized using NicA2, a microbial redox enzyme that catabolizes nicotine. Nic2A was previously reported to be responsible for nicotine degradation in *Pseudomonas putida* S16.

Herein, the inventors used RNA-Seq to identify proteins for biosensor development. As a proof of concept, the inventors performed RNA-Seq on *P. putida* S16 to identify and isolate nicA2. Accordingly, the inventors herein demonstrate use of RNA-Seq in order to identify proteins for the purpose of building biosensors. Similarly, in order to test and optimize the MRE assay disclosed herein, the inventor screened a genomic library from *P. putida* S16 to identify the oxidase nicA2 gene, demonstrating the functionality of the MRE assay to identify oxidases from gDNA libraries.

As shown in FIG. 1A-1C, the technology relates to a functional screening platform to identify microbial redox-enzymes (MREs) from environmental DNA (eDNA) sources, where in some embodiments, the screening can be cell-based or a cell-free system. For example, in some embodiments, environmental DNA libraries are screened for functional microbial redox enzymes which degrade an analyte of interest.

In particular, in some embodiments, the MRE assay comprises contacting the protein product of gDNA with an analyte of interest (e.g., target analyte), where a MRE catalyzes the target analyte and concurrently produces hydrogen peroxide which is then converted by a read-out enzyme (ReadE) and a read-out substrate (ReadS) to produce a detectable or read-out signal. As an illustrative example only, and as exemplified in the Examples herein and shown in FIG. 3E-3F, a MRE assay can be configured to identify an oxidase MRE in the presence of an analyte of interest due to the production of hydrogen peroxide ($H_2O_2$) and a peroxidase read-out enzyme, such as, e.g., APEX2, which in the presence of $H_2O_2$, catalyzes the reduced form of AUR (AURred) to the oxidized form (AURox) which is fluorescent. Thus, depending whether the gDNA is in bacterial cells (e.g., a cell-based system) or in droplets (in a cell-free system), the presence of a fluorescent signal identifies a cell or droplet containing an oxidase MRE that catalyzes the target analyte. As described herein, the MRE assay can be configured to use different redox mediators (Med), and/or different read-out enzymes (ReadE) or read-out probes to identify MREs selected from any of: oxidases, NAD(P)-dehydrogenases, and NAD(P)-independent dehydrogenases to a variety of different target analytes.

In some embodiments, the MRE assay is a cell-based system, where fragments of genomic DNA (gDNA) from an environmental source are used to generate a library and cloned into bacteria (see, e.g. FIG. 1C and FIG. 5A), and the bacteria express the gDNA to produce the microbial redox-enzymes. The bacterial library is then contacted with an analyte of interest (e.g., target analyte), at least one signal transducer (Med, ReadE/ReadS conjugate, or probe), and screened and selected for the bacteria that produce a signal in the presence of an analyte of interest.

In one embodiment, the technology relates to an optimized cell-based MRE assay. Importantly, the inventors discovered that the viability of cells expressing a MRE significantly decreases in the presence of that MRE's target analyte. Therefore, as described herein in the Examples, the inventors had to rigorously and carefully optimize the assay, including optimizing multiple different parameters to increase the viability of the cells being selected for. Stated differently, as the cell-based MRE assay selects for bacterial cells comprising an active redox-enzyme to a target analyte, the cell has an increased oxidative stress level and/or increased ROS, which can lead to decreased viability. In essence, before optimization, the assay selects for cells that are dying due to high ROS. In order to avoid this decrease this cell death and increase the viability of the cells to be selected, yet still be able to select for cells comprising an active MRE, the inventors optimized multiple parameters, including but not limited to, bacterial cell species, induction conditions, analyte exposure conditions, FACs sorting parameters, FACs chip nozzle width, sorting media, and sorting media temperatures. Therefore, the optimized cell-based MRE assay described herein enables selection of cells expressing a MRE to the target analyte without a decreased cell viability.

In alternative embodiments, cell-free systems can be used (e.g., see FIG. 1B) where fragments of gDNA from an environmental source is contacted with reagents for cell-free protein synthesis, enabling protein production in a cell-free environment, and droplets comprising the produced proteins (of which some will comprise a redox-enzymes) are contacted with at least one redox mediator (Med) and are screened and selected for those that produce a signal from the redox-mediator in the presence of an analyte of interest.

In some embodiments, in the presence of the analyte of interest, if the analyte of interest is degraded or catalyzed by an oxidase MRE specific to that analyte, $H_2O_2$ is produced which can be used as a substrate in the redox reaction of a peroxidase enzyme (e.g., HRP) or another read out enzyme (ReadE), to convert a readout substrate (ReadS) into a readout-product (ReadP), where the readout product (ReadP), is typically fluorescent and produces a detectable signal. As an exemplary MRE assay only and illustrated in FIG. 5B and FIG. 1B, if the analyte of interest is catalyzed by an oxidase MRE specific to that analyte, $H_2O_2$ is produced which can be used as a substrate for the redox reaction of APEX2 (which serves as a ReadE) to convert the readout substrate (ReadS) AMPLEX™ UltraRed (AUR) to produce resorufin (which is a readout product, ReadP), which is fluorescent and can be detected by fluorescence readings.

In some embodiments, the screening can be done via microfluidic devices designed and fabricated using software tools, such as DAFD & Fluigi. Accordingly, in such embodiments, the droplets (in a cell-free system) or bacterial colonies (in a cell-based system) can be identified as screening hits can be validated and characterized automatically on liquid handling robots. FIG. 1B shows an embodiment where the screening is in a cell-free system, where a microfluidic device is used to segregates members of the DNA library into individual droplets containing cell-free protein synthesis mix. In the cell-free method, redox-enzymes are expressed and redox-enzymes which degrade the molecule of interest (e.g., an analyte of interest, or the enzyme's substrate) will generate $H_2O_2$. In the presence of a HRP enzyme and a redox probe (e.g., Amplex™ UltraRed) that is responsive to $H_2O_2$, a fluorescent signal is produced. Droplets in the microfluidic device that produce fluorescence above a preset fluorescence threshold are sorted and sequenced. In some embodiments, putative ORFs are cloned into expression vectors automatically, and enzyme purification and characterization can be performed at high-throughput using liquid handling robots. FIG. 1C is a schematic of the metagenomic screening to identify redox-enzymes, showing obtaining gDNA from environmental sources, generating a gDNA library and cloning into recombinant bacteria that express the peroxidase enzyme APEX2 and screening the bacteria in the presence of AUR and a target analyte and selecting bacteria producing a detectable signal, and isolating the bacteria expressing the redox-enzyme.

Accordingly, the MRE assay described herein can be used to identify microbial redox enzymes for use in biosensors, in particular, the development of small, easy to use, and cheap electrochemical biosensors, where MREs identified from the assay can be obtained from environmental samples and/or bacterial cultures and catalyze physiologically relevant analytes. In some embodiments, the identified MREs can be used in biosensors that are typically composed of an electrode, e.g., a screen-printed electrode (SPE), electron mediator (e.g. Prussian Blue), and the MRE as the redox enzyme.

Accordingly, the technology described herein generally relates to assays, compositions, methods and processes to identify and isolate novel MREs that recognize a target analyte and thus the identified MREs can be used in a biosensor that can be used in a range of assays and devices. One aspect described herein is a method for identification of a microbial redox-enzyme (MRE) for use as a biosensor, which can be used for the detection of small molecules based on analyte-responsive redox enzymes for the quantification of a target analyte with high sensitivity.

Another aspect described herein is a high throughput microfluidic screening platform for the discovery and identification of microbial redox enzymes, as well as an automated characterization processes necessary for MRE validation via liquid handling robots.

Accordingly, one aspect of the technology described herein is an assay to identify microbial redox enzymes, the method requiring screening a library of genomic DNA (gDNA) samples with a target analyte, where the gDNA is obtained from an environmental source, and identifying one or more gDNA samples that encode a MRE that metabolizes a target analyte of interest, where the MRE is, for example, an oxidase or dehydrogenase enzyme, that oxidizes or degrades the target analyte. The oxidation or reduction of the target analyte by the MRE oxidase or dehydrogenase redox-enzyme results in an electro-chemical reaction that can be detected using a readout enzyme (ReadE) that converts a readout substrate (ReadS) into a readout product (ReadP) which produces a detectable signal. The detection or presence of a detectable signal is used to identify clones or gDNA samples that encode the redox-enzyme that oxidizes or reduces the target analyte.

In some embodiments, the method of screening the library of genomic DNA is performed as a high-throughput screen, for example, using a microfluidic device, as disclosed herein. In some embodiments, the high-throughput assay can be configured to be automated, for example, using liquid handling robots and automated characterization for high-throughput identification of a microbial biosensor, as described herein.

Aspects of the assay describe herein rely on catalyzing an electrochemical reaction (redox) of the MRE in the presence of a target analyte (i.e., substrate). In use, an analyte specific to the MRE is catalyzed, changing electron flow. In one non-limiting embodiment, the MRE (or a functional portion thereof) catalyzes a redox event in the presence of a target analyte (i.e., where the analyte is a substrate of the MRE). In some embodiments, the MRE is, without limitation, an oxidase, NAD(P)-dehydrogenase, and NAD(P)-independent dehydrogenase and the like. The redox event can be coupled to a redox-mediator (referred to herein as a "Med") which acts as a conductor of electrons to permit detection of the redox event between the target analyte and the MRE, thereby detecting the presence of the MRE. In some embodiments, the redox event between the target analyte and MRE can be coupled to a readout enzyme (ReadE), that acts as a conductor of electrons between the first redox event (between the target analyte and the MRE) and the redox-mediator (Med) to permit detection of the activity of the MRE reacting with the target analyte. In some embodiments, the redox-mediator can be linked to an electrode, nano-electrode or nanobioneedle, which all act as conductors of electrons to permit detection of any signal changes in the MRE.

In some embodiments, the screening is screening a gDNA library which is cloned into bacterial cells. In some embodiments, the bacterial cells can also express components of the assay, for example, the readout enzyme (ReadE), e.g., APEX2 or another peroxidase enzyme as disclosed herein. In some embodiments, the bacterial cells are selected from Rosetta 2 (DE3), Origami 2, SHuffle, Rosetta-Gami, BL-21 (DE3), Arctic Express, and Tuner. In some embodiments, the bacterial cells are selected from expression strains with a high tolerance to oxidative stress as compared to Solu-BL21, BL-21 pLys, or C41.

In alternative embodiments, the screening of the gDNA library is a cell-free system, for example, where the gDNA library is processed as single droplets, where the droplets comprise protein synthesis regents for expression of the genes, e.g., the redox-enzymes, encoded by the gDNA in the droplet.

In some embodiments, the gDNA library is a metagenomic gDNA library, and is processed through a microfluidic device to produce individual droplets, where each droplet comprises or encapsulates one or more single gDNA sample, and where the droplet comprises cell-free cell synthesis reagents to express the microbial redox-enzyme protein encoded by the gDNA in the droplet.

In some embodiments, the MRE assay or method to identify the microbial redox-enzyme can be a high-throughput system. In some embodiments, the assay can be performed on a microfluidic platform. For example, by way of an illustrative example only, a high throughput microfluidic screening platform for the discovery of microbial redox-enzyme described herein, the inventors have utilized microfluidic devices designed and fabricated in polycarbonate via a CNC micromill, using software developed by the inventors. The devices encapsulate single members of a metagenomic DNA library into individual droplets containing cell-free protein synthesis reagents to express putative enzymes from library DNA. Enzyme activity is then monitored using an Amplex™ UltraRed assay, and droplets containing enzymes which degrade the molecule of interest are sorted by fluorescence intensity. DNA within sorted droplets are then sequenced and Open Reading Frames (ORFs) are validated automatically using cell-free protein synthesis, and liquid handling robots (e.g. see, FIGS. 1A and 1B).

One aspect of the technology disclosed herein relates to a method or assay to identify a microbial redox-enzyme for detection of an analyte, the method comprising: (a) contacting a sample comprising at least one microbial redox-enzyme with (i) a redox mediator (Med), i.e. hydrogen peroxide, wherein in some instances, the redox mediator can be reduced from an oxidative form ($Med_{ox}$) to a reduced form ($Med_{red}$) only in the presence of an analyte, and wherein the $Med_{red}$ either directly or indirectly produces a detectable signal, and (ii) optionally, contacting the sample with a readout enzyme (ReadE), wherein the readout enzyme catalyzes a readout substrate (ReadS) to a detectable readout product (ReadP) only in the presence of hydrogen peroxide or other readout substrates (ReadS), (b) contacting the sample with a target analyte, wherein the target analyte is catalyzed by at least one MRE and transfers at least one electron to $Med_{ox}$ resulting in its reduction to $Med_{red}$ (c) measuring the presence of the detectable signal produced by the $Med_{red}$ or the readout product (ReadP) (d) isolating and identifying the MRE by sequencing the gDNA in the sample. In some embodiments, the sample is a gDNA library present in bacterial cells.

In all embodiments, the sample comprising at least one microbial redox-enzyme is a sample obtained from protein synthesis of a genomic DNA (gDNA) library encoding a plurality of microbial redox-enzymes, where protein synthesis occurs in a cell-free manner. In all embodiments, the sample comprising at least one microbial redox-enzyme is present in a bacterial population comprising a genomic DNA (gDNA) encoding a plurality of microbial redox-enzymes. In some embodiments herein, the method and assays described herein can be used to identify a microbial redox-enzyme selected from any of: an oxidase enzyme, a NAD (P)-dehydrogenase, NAD(P)-independent dehydrogenase enzyme.

In some embodiments herein, the assay or method is used to identify a microbial redox-enzyme which is an oxidase. In some embodiments herein, the assay or method is uses a readout enzyme (ReadE), also referred to as an Intermediate Redox Enzyme (IRE), for example, a peroxidase enzyme, such as, for example, APEX2 or homologue or variant thereof. In some embodiments, the assay or method for identifying a MRE as disclosed herein uses APEX2 or a functional variant thereof as the readout enzyme, which converts the readout substrate (ReadS) Amplex™ UltraRed (AUR) into a readout product (ReadP) resorufin, in the presence of a hydrogen peroxide.

In some embodiments herein, the assay or method is uses a readout substrate (ReadS), for example, a peroxidase responsive probe (PRP), wherein the reduced form of the PRP ($PRP_{red}$) is converted to the oxidized form of the PRP ($PRP_{ox}$) to produce a detectable signal. In some embodiments herein, the readout product (ReadP) produces a signal selected from any of: bioillumescence, optical signal, electrochemical signal, for example, when the ReadP produces an electrochemical signal, the electrochemical signal is detected by current (amperometry). In some embodiments herein, the assay or method produces a detectable signal which is a fluorescent signal, for example, where the fluorescence can be measured by FACS or other fluorescence detection system.

In some embodiments herein, the assay or method is uses a readout substrate (ReadS) or peroxidase responsive probe (PRP), for example, any readout substrate or PRP selected from any of: Amplex™ UltraRed (AUR), PY1, PO1, Hamovanillic Acid (HVA), Luminol, OPD, DCFH, ABTS, K iodine, or ABTS. In some embodiments, the assay or method for identifying a MRE as disclosed herein uses a readout substrate which is Amplex™ UltraRed (AUR).

In some embodiments, the assay or method for identifying a MRE as disclosed herein is used to screen a sample which comprises a genomic DNA (gDNA) library, for example, a gDNA library which comprises genomic DNA fragments from any environmental source. Exemplary environmental sources include, but are not limited to any one or more of: water, soil, microbiome, feces, urine, plant sources, fungal cells, fossil energy source, Artic and/or Antarctic ice samples, water and/or permafrost sources, materials of volcanic origin, materials from soil or plant sources in tropical areas, oil samples, wastewater samples, or any environmental source comprising DNA. In some embodiments, the water source is any of: deep water, contaminated water, waste water.

In some embodiments, the assay or method for identifying a MRE as disclosed herein requires contacting the sample with the target analyte, where a droplet comprising a fragment of gDNA from a gDNA library is contacted by droplet merging, with an analyte of interest, a readout enzyme (ReadE) e.g., a peroxidase enzyme (PE) and a readout substrate (ReadS), and where the droplet also comprises reagents for cell-free protein synthesis. In some embodiments, the assay or method for identifying a MRE as disclosed herein can be performed in a high-throughput manner. In some embodiments, the assay or method for identifying a MRE as disclosed herein can be performed using a microfluidic device.

Another aspect of the technology described herein relates to manner a method of identifying a MRE in a cell-free manner, comprising (a) providing a library of nucleic acid sequences comprising genomic DNA (gDNA) obtained from at least one environmental source with one or more reagents for cell-free protein synthesis, (b) generating nano-volume droplets of the library and contacting the droplets with a target analyte, a readout enzyme and a readout substrate, wherein the readout substrate is converted to a readout product (ReadP) which produces a detectable signal in the presence of a MRE that is specific to the target analyte, and (c) measuring the presence of a detectable signal produced from the readout product, (d) isolating the gDNA and cloning into a vector, wherein the gDNA encodes a MRE that is specific to the target analyte.

Another aspect of the technology described herein relates to a library of expression vectors, each comprising at least one promoter, at least one nucleic acid sequence encoding a MRE, a nucleic acid encoding a readout enzyme, wherein the at least one nucleic acid sequence encoding a MRE and nucleic acid encoding a readout enzyme are operatively linked to a promoter. In some embodiments, the bacterial cell can comprise two plasmids, a first plasmid comprising least one first promoter operatively connected to at least one nucleic acid sequence encoding a MRE, and a second plasmid comprising at least one second promoter operatively linked to a nucleic acid encoding a readout enzyme. In some embodiments, the first and second promoters are the same promoters, and in some embodiments, the first and second promoters are different. In some embodiments, both apex2 and nicA2 are present on the same plasmid expressed by the same promoter. In some embodiments, the first and/or second promoters are inducible promoters commonly known to persons of ordinary skill in the art.

In some embodiments, the readout enzyme is APEX2. In some embodiments, the at least one nucleic acid sequence encoding a MRE is obtained from genomic DNA (gDNA) obtained from an environmental source, as described herein. In other embodiments, the ORF containing the MRE and the readout enzyme (ReadE) are on the same plasmid and expressed by the same promoter.

Another aspect of the technology described herein relates to a plurality of cells comprising the library of expression vectors as disclosed herein.

Another aspect of the technology described herein relates to a method of screening, comprising (a) contacting a library of expression vectors described herein with a target analyte and a redox mediator (Med), and optionally a readout enzyme, wherein the redox mediator directly or indirectly via a readout enzyme transfers electrons from the Med to readout substrate (ReadS) to generate a readout product (ReadP) produces a detectable signal in the presence of a MRE that is specific to the target analyte, and (b) measuring the presence of a detectable signal produced from the redox mediator or readout product (ReadP), and (c) isolating the expression vector encoding the MRE that is specific to the target analyte. In some embodiments, the readout substrate is AUR, and wherein AUR is converted to resorufin (readout product) which produces a florescence signal if a MRE is present that catalyzes the target of interest. In some embodiments, measuring the fluorescence signal is using FACS. In some embodiments, the method is performed in a high-throughput manner. In some embodiments, the method is performed on a microfluidic device.

Another aspect of the technology described herein relates a microfluidic device for performing the methods and assays to identify a MRE to a target analyte as disclosed herein.

In some embodiments, the assay or method for identifying a MRE as disclosed herein can be used to identify a MRE that catalyzes (or degrades or oxidizes) a target analyte selected from any of a small molecule, toxin, neurotransmitter, steroid, immunomodulator, metabolite, hormone, e.g., a hormone selected from any of the group of: progesterone, estradiol, estrone, estriol, progesterone, testosterone, aldosterone, prednisolone, androstadienone, cortisol, cholesterol.

In some embodiments, the assay or method for identifying a MRE as disclosed herein can produce a detectable signal, for example fluorescence from a fluorescent molecule or a quantum dot (QD). In some embodiments, a fluorescent molecule comprises a FRET acceptor and a second fluorescent reporter comprises a FRET donor. In some embodiments, the fluorescent molecule is selected from the group consisting of a quantum dot, a fluorescent dye, a fluorescent protein, and combinations thereof.

In one aspect, described herein is a method for determining the presence or absence of a MRE catalyzing an analyte of interest; and wherein in the presence of a MRE capable of detecting an analyte of interest, the analyte will be catalyzed (in some embodiments degraded) to generate a product, and also can produce the redox mediator (Med), such as hydrogen peroxide, where the $H_2O_2$ can be detected directly (e.g., with a $H_2O_2$-responsive transcription factor as disclosed herein), or where the $H_2O_2$ can be used in a subsequent redox reaction to reduce a readout substrate (ReadS) to a readout product (ReadP) resulting in the emission of a fluorescent signal, and wherein in the absence of the MRE capable of detecting the analyte of interest, no signal will be generated, whereas when a signal is detected, and selecting an MRE that generates a signal.

In one aspect, described herein is a method for detecting a MRE catalyzing an analyte of interest in a sample; contacting the sample comprising a MRE capable of detecting an analyte of interest and one or more fluorescent probes; whereby when the analyte is degraded or catalyzed by the MRE, $H_2O_2$ will be generated, where the presence of $H_2O_2$ can be detected or used in a subsequent redox reaction (e.g., conversion of a readout substrate to a readout product) to generate a detectable signal, e.g., a fluorescent signal; wherein in the absence of a MRE specific to the analyte of interest, the analyte will not be catalyzed or degraded and will not generate $H_2O_2$ resulting in no emission of a fluorescent signal.

In one aspect, described herein is a kit for determining the presence or absence of a MRE, the kit comprising any one or more of: reagents to obtain gDNA from an environmental source, reagents to generate a metagenomic library, a cell-free protein synthesis kit, a redox mediator (Med), and optionally a readout enzyme and readout substrate. In some embodiments, the kit comprises any one or more of: reagents to obtain gDNA from an environmental source, reagents to generate a metagenomic library, a cell-free protein synthesis kit, AUR as the readout substrate, HRP or APEX2 as the readout enzyme.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 1A. Environmental DNA libraries are screened for functional redox enzymes which degrade a molecule (e.g., analyte) of interest, via microfluidic devices designed and fabricated using our software tools DAFD & Fluigi. Screening hits are validated and characterized automatically on liquid handling robots. FIG. 1B. The screening microfluidic segregates members of the DNA library into individual droplets containing cell-free protein synthesis mix. Expressed enzymes which degrade the molecule of interest (enzyme substrate) and generate $H_2O_2$ that produces a fluorescent signal using the chemical probe Amplex™ UltraRed. Droplets above a preset fluorescence threshold are sorted and sequenced. Automated DNA assembly can be done on the world wide web at mocloassembly.com. Putative ORFs are cloned into expression vectors automatically, and enzyme purification and characterization are performed at high-throughput using liquid handling robots. FIG. 1C is a schematic of the metagenomic screening to identify redox-enzymes, showing obtaining gDNA from environmental sources, generating a gDNA library and cloning into recombinant bacteria that express the peroxidase enzyme APEX2 and screening the bacteria in the presence of AUR and a target analyte and selecting bacteria producing a detectable signal, and isolating the bacteria expressing the redox-enzyme.

FIG. 2A shows the results from two redox enzymes, APEX2 and NicA2, which were expressed in cell-free and tested for functionality using Amplex™ UltraRed. Arrows indicate time of addition of enzyme substrates (APEX2—$H_2O_2$, NicA2—Nicotine). FIG. 2B shows microdroplets on a microfluidic device, where the droplets contain a cell-free protein expression mix & X-Gal. Droplets contain either no DNA, or plasmid DNA driving LacZ (β-galactosidase) expression. Only droplets expressing LacZ are able to produce a blue color change, demonstrating functional protein can be expressed within droplets.

FIG. 3A shows a reaction scheme for detection of an oxidase MRE. FIG. 3B illustrates an exemplary a multi-enzyme coupled system for detection of an oxidase MRE, where a peroxidase is used as a readout enzyme to generate a signal in the presence of hydrogen peroxide produced by the oxidase MRE. FIG. 3C shows an exemplary a multi-enzyme coupled system for detection of an oxidase MRE, where APEX2 peroxidase is used as a readout enzyme (also referred to as an intermediate redox enzyme, or IRE, and a signal from the catalysis of Amplex™ UltraRed (readout substrate) to resorufin (readout product), which produces a detectable fluorescent signal occurs in the presence of hydrogen peroxide produced by the oxidase MRE. FIG. 3D shows an exemplary reaction scheme for non-electrochemical detection of an oxidase MRE, using a hydrogen peroxide responsive probe. The hydrogen peroxide responsive probe produces a detectable signal in the presence of hydrogen peroxide. FIG. 3E and FIG. 3F show multi-enzyme couple reactions (e.g., oxidase-peroxidase coupling). FIG. 3E shows an exemplary reaction scheme for non-electrochemical detection of an oxidase MRE, using a peroxidase and a hydrogen peroxide responsive probe. FIG. 3F shows an exemplary reaction scheme for non-electrochemical detection of an oxidase MRE, using APEX2 and a hydrogen peroxide responsive probe.

FIG. 4A-4C show reaction schemes for detection of a NAD(P)-independent dehydrogenase redox-enzyme. FIG. 4A shows a reaction scheme for detection of a NAD(P)-independent dehydrogenase redox-enzyme, using second generation electrochemical detection. FIG. 4B shows a reaction scheme for detection of a NAD(P)-independent dehydrogenase redox-enzyme, using third generation electrochemical detection. FIG. 4C shows a reaction scheme for detection of a NAD(P)-independent dehydrogenase redox-enzyme, using non-electrochemical detection and a NAD(P)-independent responsive probe (NIP). FIG. 4D-4F show reaction schemes for detection of a $NAD(P)^+$-dehydrogenase dehydrogenase redox-enzyme. FIG. 4D shows a reaction scheme for detection of a $NAD(P)^+$-dehydrogenase redox-enzyme, using second generation electrochemical detection. FIG. 4E shows a reaction scheme for detection of a $NAD(P)^+$-dehydrogenase redox-enzyme, using third generation electrochemical detection. FIG. 4F shows a reaction scheme for detection of a $NAD(P)^+$-dehydrogenase redox-enzyme, using non-electrochemical detection and a NAD(P) or a NAD(P)H-dependent responsive probe (NAD(P)-DP).

FIG. 5A shows a schematic of the generation of the gDNA library and expression in engineered bacteria expressing APEX2. FIG. 5B shows exemplary schematics of electron flow from the candidate MRE in the presence of a target analyte, which results in the conversion of Amplex™ UltraRed (readout substrate) by APEX2 peroxidase enzyme (readout enzyme) to resorufin (readout product), which produces a detectable signal. A peroxide enzyme, such as HRP and corresponding readout substrate (ReadS) can be used in place of APEX2 and Amplex™ UltraRed, however, as discussed herein, functional expression of HRP in vivo is challenging, and thus APEX2 or a similar readout enzyme is preferred. FIG. 5C shows exemplary target analytes, selected from tyramine, octopamine, dopamine, norepinephrine, histamine, tryptamine, benzylamine, serotonin, nicotine can be detected with the MAO oxidase from C. ammoniagenes.

FIGS. 7A-7D show results of enrichment of cells with spiking with either MAO or NicA2 MRE proteins. FIG. 7A shows fold enrichment for cells in the presence of 40 µM or 80 µM IPTG, when the cells were either spiked with 10% or 1% mao plasmid (left panel) or nicA2 plasmid (right panel). FIG. 7B shows fold enrichment for cells in the presence of 80 µM IPTG, when the cells were either spiked with 0.01%, 0.1% or 1% nicA2 containing plasmids, demonstrating that the assay was capable of detecting low levels of NicA2 expression. FIG. 7C shows fluorescence expression of cells expressing APEX2 when the cells are spiked with NicA2, and contacted with nicotine or myosmine, or $H_2O_2$ (control), showing robust fluorescence of cells expressing APEX2 and NicA2, when they are contacted with nicotine, but not myosmine. FIG. 7D shows that over time, cells expressing NicA2 produce nicotine-dependent fluorescent signal using AUR and APEX2.

FIG. 8A shows a construct with a 5' promoter (e.g., T7) and a 3' stop codon (T), and the nucleic acid comprising a gDNA fragment encoding a potential candidate MRE in a forward orientation with respect to the promoter. FIG. 8B shows a construct with a 5' promoter (e.g., T7) and a 3' stop codon (T), and the nucleic acid comprising a gDNA fragment encoding a potential candidate in a same orientation with respect to the promoter and at the final ORF. FIG. 8C shows a plasmid construct similar to FIG. 8B, except that the ORF encoding a potential candidate MRE can be present at a different location within the gene fragment. FIG. 8D shows a construct similar to FIG. 8B except that the gDNA fragment, and thus, the ORF encoding the MRE can be in a reverse orientation with respect to the promoter.

FIG. 9A shows a control construct with an exemplary redox-enzyme, nicA2, operatively linked to a constitutive T7 promoter, a ribosome binding site, and a stop codon downstream of the nicA2 gene. FIG. 9B shows construct A with an exemplary MRE, nicA2, in its native form with no ribosome binding site operatively linked to a constitutive T7 promoter, and a stop codon 3' of the native nicA2 gene. FIG. 9C shows construct B with an exemplary MRE, nicA2, operatively linked to a constitutive T7 promoter and also additional nucleic acid sequences (2.6 kb) encoding other ORFs operatively linked to the promoter. FIG. 9D shows construct C with an exemplary MRE, nicA2, operatively linked to a constitutive T7 promoter and also additional nucleic acid sequences (5.7 kb) encoding other ORFs operatively linked to the promoter.

FIG. 10A shows levels of fluorescence detected with increasing expression (by increasing IPTG concentration) from a control plasmid (comprising nicA2; see e.g., FIG. 9A). FIG. 10B shows levels of fluorescence detected with increasing expression (by increasing IPTG concentration) from construct A (see e.g., FIG. 9B). FIG. 10C shows levels of fluorescence detected with increasing expression (by increasing IPTG concentration) from construct B (see e.g., FIG. 9C). FIG. 10D shows levels of fluorescence detected with increasing expression (by increasing IPTG concentration) from construct C (see e.g., FIG. 9D).

FIG. 11A shows FACS results and shows that with increasing IPTG concentration and increasing time periods (0 h, 1 h, 2 h, 3 h, 4 h, 5 h), increasing numbers of florescent cells are detected and can be sorted. FIG. 11B is a table of the FACS results of FIG. 11A depicting increase of fluorescent cells with increasing amounts of IPTG. Furthermore, the more IPTG added, the quicker cells are converted to fluorescence.

FIG. 12A show FACS results using nicotine (100 µM), or octopamine (100 µM), or hydrogen peroxide (positive control) showing presence of a detectable fluorescent signal as detected by FACS. FIG. 12B is a schematic showing the collection of 10,000 fluorescent cells for next generation sequencing (NGS) analysis.

FIG. 13A shows placement of primers (bent lines) at the 5' and 3' positions between the region encoding a redox enzyme. These primers are used to amplify the sequences resulting from cells sorted during FACS exposed to either nicotine, targeting nicA2, or octopamine, targeting the mao and also the positive and negative controls. The experimental design involved a 50% mixture of nicA2 containing plasmids and 50% mao containing plasmids which were FAC sorted with different analytes and analyzed. FIG. 13B shows the minimum amount of events (cells) needed to be sorted into a PCR mix in order to amplify the plasmids depicted in FIG. 13A. At minimum, 100 cells needed to be sorted into the PCR mixture in order to amplify any plasmids present.

FIG. 14A shows the optimized fragmentation of PCR products from FAC sorted cells using different analytes (nicotine or octopamine) as compared to a negative control or $H_2O_2$ positive control. FIG. 14B shows use of next generation sequencing (NGS) to track enrichment of cells in the presence of analytes nicotine or octopamine, as compared to in the presence of a negative control or positive control ($H_2O_2$). With both the positive and negative controls both redox enzymes, NicA2 and MAO, were expressed. The analyte-specific redox enzyme was enriched in the presence of the corresponding analyte.

FIG. 15A depicts the first vector architecture used. Metagenomic fragments were cloned by seamless cloning into a vector between a toxin gene, ccdB, and an upstream promoter (e.g., T7) and downstream stop codon. FIG. 15B shows a schematic of the location of where the gDNA fragments can be introduced, inside of the ccdB gene. The introduction of NGS adapters onto gDNA fragments allowed for unbiased amplification and introduction into the same vector backbone for the improved metagenomic library construction design. Metagenomic fragments were introduced recombination sites and cloned into a vector containing a toxin gene, ccdB, between the recombination sites. This metagenomic library construction design improved cloning efficiency.

FIG. 16A shows an exemplary library vector construct comprising a toxin gene (ccdB), operatively linked to constitutive promoter (pConst) and a downstream STOP codon, flanked between recombinase sites and a promoter (e.g., T7) and 5 stop codon. The presence of recombination sites allow for the use of recombinational cloning, which improves cloning efficiency dramatically. FIG. 16B shows a schematic for cloning a gDNA fragment into the vector of FIG. 16A through homologous recombination.

FIG. 17A shows fluorescent signal produced with increasing IPTG concentrations with and without nicotine with the construct produced as shown in FIG. 15B. FIG. 17B shows the step-wise increase in a fluorescent signal produced with increasing IPTG concentrations with the construct produced as shown in FIG. 16B to compare fluorescence using the same gene, nicA2, but comparing the old and new gDNA library construction designs.

FIG. 19 shows fragments isolated from the screening technology described herein after sorting Rosetta2 (DE3) cells containing a plasmid expressing apex2 and a *Pseudomonas putida* S16 gDNA library in the presence of nicotine. nicA2 was successfully enriched for and identified from $1/192$ colonies validated (see e.g., upper panel). The theoretical identification rate for random sampling of a *Pseudomonas putida* S16 gDNA library would be ~$1/22000$. When repeated with a 50/50 mixture of a *Pseudomonas putida* S16 gDNA library and a cells without the library identified nicA2 at $1/288$ (see e.g., lower panel).

FIG. 21A is a schematic showing the Amplex™ UltraRed mechanism. Nicotine is oxidized into n-methyl-myosmine and $H_2O_2$ with presence of NicA2 and $O_2$. Horseradish peroxidase (HRP) then reduces Amplex™ UltraRed in the presence of $H_2O_2$ into resorufin, which is fluorescent. FIG. 21B shows that the signal is analyte dependent when keeping NicA2 concentrations constant. FIG. 21C shows that the signal is not enzyme limited when varying NicA2 concentrations; however, the catalytic rate is concentration dependent. FIG. 21D compares resorufin fluorescence from nicotine to fluorescence from $H_2O_2$, which directly confirms a 1:1 production of $H_2O_2$ from nicotine by NicA2. RFU: relative fluorescent units.

FIG. 22A shows a dose response to various concentrations of nicotine. FIG. 22B shows a calibration curve. The raw data of a chronoamperometric experiment with 200 µM nicotine is shown in the inset. FIG. 22C shows a specificity study. A mixture of common interferents were prepared in PBS (see e.g., Table 4). Addition of 30 µL 200 µM nicotine solution to 30 µL mixture was performed at a predefined time point, and current was recorded over time. Similar experiments were performed to evaluate the selectivity of the sensor to cotinine. FIG. 22D shows NicA2 dependence of the biosensor. Myosmine, an inhibitor of NicA2, was added in the middle of a chronoamperometric experiment. Minimal response from myosmine alone (red bar) or nicotine addition after NicA2 was inhibited by myosmine (purple bar).

FIG. 26A shows cells expressing APEX2 can detect levels of $H_2O_2$ within the range of 10 µM-1 mM intracellularly. FIG. 26B is a histogram that shows detection of $H_2O_2$ as low as 10 µM in DE-131 cells.

FIG. 27A is a schematic to demonstrate an exemplary cell-based MRE assay, where a bacterial cell expresses apex2 or another peroxidase, which can detect the presence of $H_2O_2$ produced by the candidate MRE in the presence of the target analyte (represented by a "?"); the produced $H_2O_2$ converts Amplex™ UltraRed (AUR) into a detectable fluorescent signal. FIG. 27B is a schematic of an exemplary cell-free MRE assay, where cell-free protein production of a candidate MRE occurs in droplets, combined with APEX2 or another peroxidase (e.g., HRP). The target analyte (represented by a "?") leads to the production of $H_2O_2$ by the candidate MRE, and in the presence of $H_2O_2$ APEX2 (or another peroxidase) converts Amplex™ UltraRed into a detectable fluorescent signal.

FIG. 28A shows AUR fluorescence in Rosetta2 (DE3) cells expressing MAO in response to analytes tyramine, octopamine, dopamine, norepinephrine, histamine, tryptamine, benzylamine, serotonin, or nicotine; tyramine, octopamine, tryptamine, and benzylamine produce fluorescent signal and do not decrease cell viability. Cell viability is substantially decreased in the presence of nicotine. FIG. 28B is similar to FIG. 28A and shows AUR fluorescence of C41 cells expressing MAO treated with analytes tyramine, octopamine, dopamine, norepinephrine, histamine, tryptamine, benzylamine, serotonin, or nicotine; it shows that C41 AUR fluorescing cells have decreased viability as compared to Rosetta2 (DE3) cells in the presence of tyramine, octopamine, and tryptamine.

FIG. 29A-29B show increased protein expression of APEX2 and NicA2 increases fluorescence. FIG. 29A shows dose dependence of fluorescence due to strong, medium and weak apex2 expression, and dose-dependent increase of induced expression of nicA2 from two plasmids in Rosetta2 (DE3) and C41 cells. Rosetta2 (DE3) show less dose-dependent fluorescence than C41 cells, demonstrating different bacterial cells are more resistant to either increased ROS and/or increased fluorescence. FIG. 29B shows fluorescence in Rosetta2 or C41 cells after dose-dependent increase in nicA2 expression (by IPTG induction) where apex2 is under the control of a strong, medium or weak promoter.

FIG. 30A-30B shows a decrease in viability of cells in both Rosetta2 (DE3) and C41 cell strains expressing apex2 and nicA2, as compared to apex2 alone. A 50/50% mixture of cells with apex2 and nicA2 containing cells was made and exposed to various substrates. The cell mixture was either uninduced with IPTG or induced with 20 μM IPTG and plated onto agar plates. The percentage of colonies containing either both apex2 and nicA2 or apex2 alone was compared. FIG. 30A shows decreased viability of Rosetta2 (DE3) with expression of both apex2 and nicA2, especially in the presence of AUR and nicotine. FIG. 30B shows decreased viability of C41 with expression of both apex2 and nicA2, especially in the presence of AUR and nicotine.

FIG. 31A shows a schematic of the experimental setup. FIG. 31B shows % of Rosetta2 (DE3) cells with nicA2 and apex2 before FACS (All[Pre]), in all the fluorescent gates post FACS (All[Post]), and then in the three fluorescent gates demarked by the dashed lines above (low, medium, and high). The greater the fluorescence the less Rosetta2 (DE3) cells are viable post FACS. FIG. 31C shows % of C41 cells with nicA2 and apex2 before FACS (All[Pre]), in all the fluorescent gates post FACS (All[Post]), and then in the three fluorescent gates demarked by the dashed lines above (low, medium, and high). The greater the fluorescence the less C41 cells are viable post FACS.

FIG. 33A-33C show both Rosetta2 (DE3) and C41 cells expressing nicA2 have decreased viability post sort. FIG. 33A shows fluorescent FACs sorted Rosetta2 (DE3) and C41 cells do not grow and are not viable, whereas FACs sorted non-fluorescent cells are still viable. C41 exhibits greater post-sort viability from the basal (non-fluorescent) level. FIG. 33B shows the number of colonies post-sort of Rosetta2 (DE3) cells from either the non-fluorescent or fluorescent FACs gates can be improved by changing pre-sort growth conditions. V1 corresponds to cells grown overnight under induction in a sealed plate. V2 corresponds to cells grown overnight under induction in an aerated culture tube. V3 corresponds to mid-log under induction. V4 corresponds to cells grown to mid-log then induced for 2 hours at room temperature. V4 produced the best viability results, although fluorescent cells are non-viable in all conditions. FIG. 33C shows the number of colonies post-sort of Rosetta2 (DE3) cells from either the non-fluorescent or fluorescent FACs gates can be improved by changing pre-sort growth conditions. V1-4 are the same conditions as in FIG. 33B. C41 cells are more viable in both the non-fluorescent and fluorescent gates than Rosetta2 (DE3). V3 and V4 produced the most viable C41 cells in both fluorescence FACS gates.

FIG. 35A-35B shows fluorescence activity is linked to reduced cell viability. FIG. 35A shows a FACs sorting schematic and the viability of cells from basal, low, medium, and high fluorescence FACs gating channels. FIG. 35B shows possible causes of the reduced viability of fluorescent nicA2 and apex2 expressing cells, showing each parameter that were assessed and optimized to achieve increased viability of fluorescence nicA2 and apex2 expressing cells in the presence of nicotine and the readout substrate, AUR. The optimized parameters include, but are not limited to: presence of nicotine, $H_2O_2$, resorufin, presence of antioxidants, treatment media (PBS vs. 2×YTP), FACs sorting modes (purity levels, criteria for indexing), FACs chip nozzle width (70 μm, 100 μM, 130 μM), anaerobic vs. aerobic incubation, post-sort media (liquid vs. agar), or post-sort media temperature (4° C., room temperature, 37° C.).

FIG. 36A shows different bacterial strains are more resistant to fluorescent cell death or have increased viability in the presence of 1 μM nicotine and 20 μM AUR. FIG. 36B shows viability of fluorescent vs. non-fluorescent C41 cells kept at room temperature or chilled, which shows that chilling of C41 cells pre- and post-sort does not rescue viability. FIG. 36C shows viability of fluorescent vs. non-fluorescent C41 cells cultured with glutathione post-sort, showing that glutathione does not rescue viability. FIG. 36D shows viability of fluorescence vs. non-fluorescence C41 cells post-sort cultured in anaerobic or aerobic conditions pre-sort, showing that growing cells aerobically pre-sort significantly increased post-sort viability. However, fluorescence is greatly reduced under aerobic induction.

Figure 37:
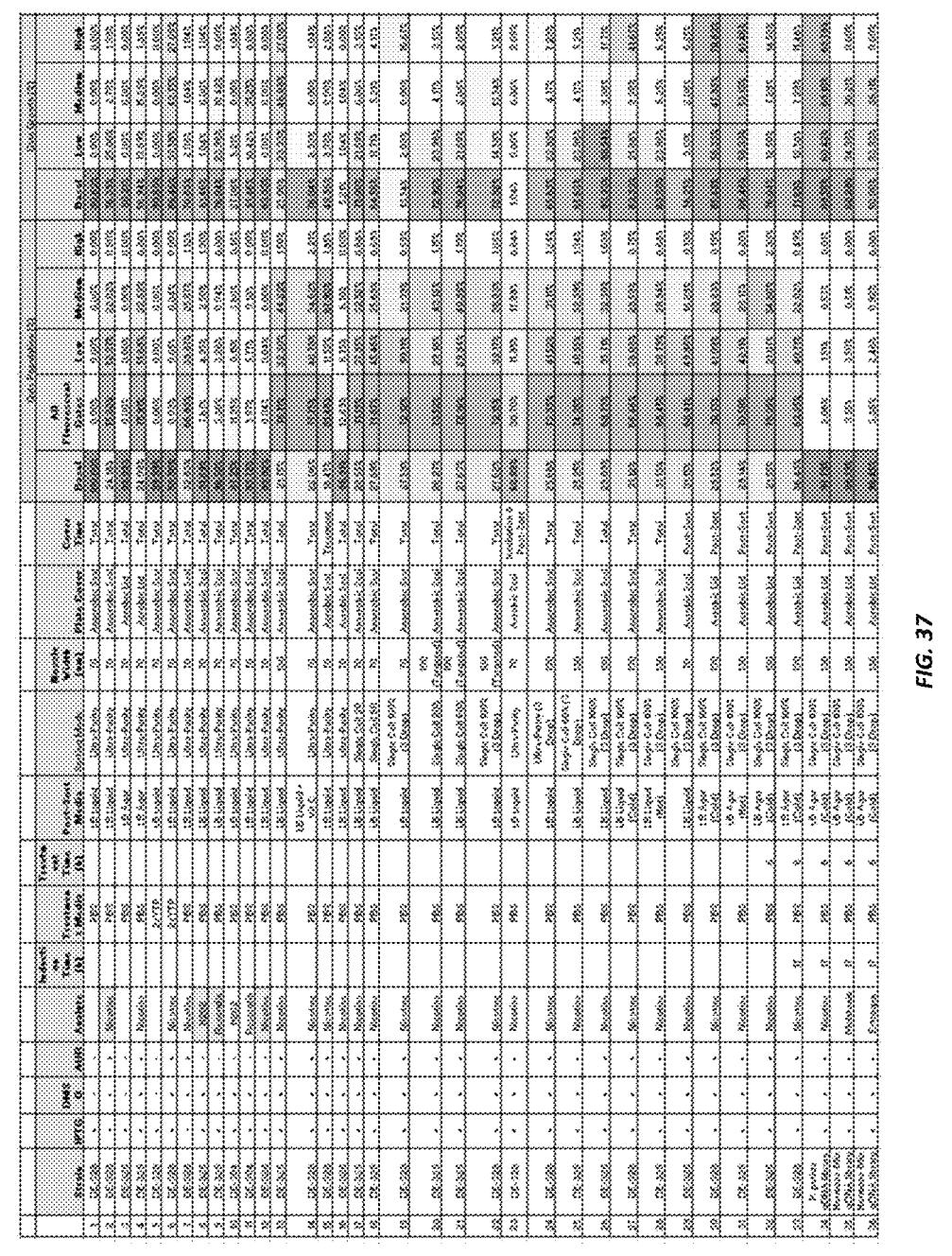

FIG. 37 is a Table showing results of the optimization of the cell-based MRE assay.

FIG. 40A shows two clones (clones A and B) that comprise a gDNA fragment encoding a candidate MRE that is responsive to lidocane. FIG. 40B shows two clones (clones C and D) that comprise a gDNA fragment encoding a candidate MRE that is responsive to cortisol.

FIG. 41A shows a clone that comprises a gDNA fragment encoding a candidate MRE that is responsive to hydrocortisone. FIG. 41B shows increased fluorescence in the presence of hydrocortisone over time as compared to no hydrocortisone. FIG. 41C shows expression of orf1 from the gDNA fragment contained in the clone in FIG. 41A did not express a candidate MRE specific to hydrocortisone. FIG. 41D shows expression of orf2 from the gDNA fragment contained in the clone in FIG. 41A expresses the candidate MRE specific to hydrocortisone. FIG. 41E shows cells containing and expressing orf2 produce a MRE that is specific to hydrocortisone, and does not catalyze other analytes. FIG. 41F shows the MRE produced from orf2 alone is specific to hydrocortisone, and does not catalyze other analytes.

FIG. 43A shows conversion of PO1, PY1 and PF2 (or PF33 or PE1) into fluorescent products in the presence of $H_2O_2$. FIG. 44P shows the $H_2O_2$-mediated release of coumarin. Other examples of $H_2O_2$ probes exist in Zamojc et al., Crit Rev. in Analytical Chemistry, 2016; 46 (3); 171-200.

DETAILED DESCRIPTION

Figure 1A:
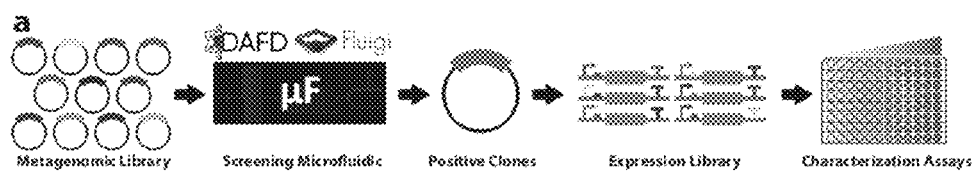
FIGS. 1A-1C show a schematic of an exemplary functional screening platform to identify redox-enzymes from environmental DNA (eDNA) sources.

The technology described herein relates to assays, methods, systems, compositions and assays to identify redox enzymes, in particular, microbial redox enzymes (MREs) to a target analyte. In some embodiments, the method encompasses screening a genomic DNA (gDNA) library in a cell-free or cell-based system to identify a MRE that catalyzes a target analyte.

Briefly, the methods described herein relate to assays and systems for identification of a redox-enzyme, e.g., a microbial redox enzyme for the detection of small molecules based on analyte-responsive redox enzymes, which can be used as the biorecognition element/analyte-sensing component in biosensors for quantification of a target analyte with high sensitivity. Described herein are compositions, methods and processes to identify and isolate MREs that recognize a target analyte which can be used in a wide range of biosensor devices Accordingly, also described herein is an ultra-high throughput microfluidic screening platform for the discovery of MRE, as well as an automated characterization processes necessary for MRE validation via liquid handling robots. The platform requires two inputs from the user: a nucleic acid probe (e.g. a genomic DNA (gDNA) library) from which to screen for MREs, and an analyte of interest. Given these two inputs, the platform detects oxidases or other MRE responsive to the analyte of interest and separates out the DNA which contains the novel MRE which can be sequenced downstream and used to in a biosensor device.

I. Biosensors in General

The label-free sensing of small molecule analytes is of critical importance to biomedical research, point of care diagnostics, and environmental sensing, among other applications. Connected devices that monitor human biology in real-time represent the next frontier in biosensors. Monitoring hormones is of significant interest as hormones play critical roles in multiple physiological processes including stress adaptation, blood pressure control, reproductive rhythms, and body odor. However, the real-time monitoring of hormones is challenging from a biology, chemistry, and engineering perspective, glucose detection being the one notable success. Using natural sensing elements from microbial species e.g. native biomolecules that have evolved sensor and modulator capabilities provides the opportunity to utilize a detection platform that is distinct from the typical antibody- or aptamer-based strategies. Described herein is a screening platform for the discovery of biosensors for the detection of small molecules and analytes based on functional redox enzymes.

A biosensor is a device comprising a biological sensor element (also referred to as a biorecognition element or biological component) that typically produces electronic signals that are proportional to the concentration of a particular substance to be determined.

The use of enzymes as bioactive interfaces is well known in the art, and such interfaces are used in analytical methods of detecting electronic transduction of enzyme-substrate reactions. Direct electrical activation of enzymes such as redox enzymes permits stimulation of bioelectrocatalyzed oxidation or reduction of enzyme substrates. Rapid transfer of electrons between an electrode and a given redox enzyme results in current generation corresponding to the rate of turnover of the electron exchange between the substrate and biocatalyst. In other words, the transduced current of the system correlates with enzyme substrate concentration. Electrical contacting of redox proteins in a biosensor and the electrode support contained therein may be mediated by direct electron transfer with electrode surfaces. Redox enzymes lacking direct electrical communication with electrodes may achieve electrical contact by mediated electron transfer via redox mediators that serve as active charge carriers.

Biosensors, e.g., nanobiosensors are a type of analytical device that use biological molecules to monitor biorecognition events and interactions. Generally, a nanobiosensor comprises a biological component, a linker or redox-mediator (Med) alongside nanoelectrodes; the various components can be equated with the electronic elements of a sensor because the components transduce the signal generated at the source (bioelement) to the detector (electrode). In general, a biological component of a nanobiosensor can be a protein (e.g., enzyme or antibody), nucleic acid (DNA or RNA) or even entire cells.

Herein, the technology relates to identifying biological components, specifically microbial redox-enzymes for use in a biosensor device. The redox-enzyme is responsible for the binding and recognition of a target analyte, whether a small molecule or a large protein partner. The binding of the redox-enzyme to the target analyte is the basis for signal generation and a physical element, such a detectable signal is generated, and can an electrode, captures the signal as the output. Thus, coupling the redox-enzyme with a mediator, translates information from the binding of the target analyte and redox-enzyme into a chemical or physical output with a defined sensitivity. The information that is detected can be chemical, energetic, such as detection of light, and/or signal detection and transduction.

A "redox enzyme" or "oxidoreductases" are used interchangeably herein and refer to an enzyme that catalyzes a reaction with one or more enzyme substrate(s), resulting in generation or utilization of electrons. Redox enzymes are proteins that catalyze electron transfer by reduction or oxidation of substrates within the redox network. The oxidoreductases (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection reduced coenzyme nicotinamide adenine dinucleotide (NAD(P)H) or hydrogen peroxide has been used galvanometer biosensor.

A redox reaction is a chemical reaction in which the oxidation states of atoms are changed. Any such reaction involves both a reduction process and a complementary oxidation process, two key concepts involved with electron transfer processes. Redox reactions include all chemical reactions in which atoms have their oxidation state changed; in general, redox reactions involve the transfer of electrons between chemical species.

II. Methods to Identify Novel Microbial Redox Enzyme (MREs)

The technology described herein relates to the detection of redox-enzymes, e.g., microbial redox-enzymes (MREs) that can be used as a biosensor, and for use in a device for the accurate, reliable and sensitive measurement of an analyte of interest in the environmental, industrial, or clinical setting. In one embodiment, described herein is an assay or system for the detection of an analyte-responsive MRE for the quantification of a target analyte with high sensitivity.

Accordingly, described herein are assays, compositions, methods and processes to identify and isolate a MRE that recognizes a target analyte, such that these MREs can be used as the biorecognition element in biosensor devices that can be used in a range of assays and devices.

Aspects of the assay describe herein rely on catalyzing an electrochemical reaction (redox) of the MRE in the presence of a target analyte (i.e., substrate). In use, an analyte specific to the MRE is catalyzed, changing electron flow through the MRE to generate a product and a redox mediator. In one non-limiting embodiment, the MRE (or a functional portion thereof) catalyzes a redox event in the presence of a target analyte (i.e., where the analyte is a substrate of the redox enzyme). In some embodiments, the MRE is, without limitation, a peroxidase, an oxidase, a NAD(P)-dehydrogenase, NAD(P)-independent dehydrogenase enzyme and the like. The redox event can be coupled to a redox-mediator (referred to herein as a "Med") which acts as a conductor of electrons to permit detection of the redox event between the target analyte and the MRE, thereby detecting the presence of the MRE. In some embodiments, the redox event between the target analyte and MRE can be coupled to a readout enzyme (ReadE) (also referred to as an intermediate redox enzyme (IRE)), that acts as a conductor of electrons between the first redox event (between the target analyte and the MRE) and the redox-mediator (Med) to permit detection of the activity of the MRE reacting with the target analyte.

In some embodiments, the redox-mediator directly generates a signal detectable by optical methods, such as, without limitation, fluorescence, surface plasmon resonance, or piezoelectric methods. In some embodiments, the redox-mediator indirectly generates a signal by conducting electrons to a readout substrate (ReadS) to generate a readout product (ReadP) which is catalyzed by a readout enzyme, where the ReadP produces a detectable signal, detectable by optical methods, such as, without limitation, fluorescence, colorometric detection, surface plasmon resonance, or piezoelectric methods.

In one embodiment, the MRE being assayed for is any one or: an oxidase enzyme, peroxidase, a NAD(P)-dehydrogenase, NAD(P)-independent dehydrogenase enzyme, carboxylases, and the like. In some embodiments, the MRE assay exemplified in the Examples is used to identify a MRE oxidase. In some embodiments, the MRE assay exemplified in the Examples to identify an oxidase can be modified by one of ordinary skill in the art to identify a NAD(P)-dehydrogenase or NAD(P)-independent dehydrogenase enzyme, where the catalysis of a target analyte by a candidate NAD(P)-dehydrogenase or NAD(P)-independent dehydrogenase enzyme results in the direct, or indirect production of hydrogen peroxide, which can be detected using the readout substrate (ReadS) that detect presence of $H_2O_2$ herein.

III. Assay Systems for Detecting Oxidase Redox-Enzymes

In some embodiments, the readout enzyme (ReadE) converts a readout substrate (ReadS) to a readout product (ReadP), which generates a signal detectable by optical methods, such as, without limitation, chemiluminescence, fluorescence, colorimetric detection, and in some embodiments, the redox-meditator produces an electrical readout as detected by electrochemical techniques such as potentiometric, amperometric, or piezoelectric methods. Finally, surface plasmon resonance can also be used.

In some embodiments, an electrochemical variation of the assay is used to identify an oxidase MRE. In such an embodiment, the assay to detect an oxidase MRE, a reaction can proceed in four steps as shown in the reaction scheme 1 below:

MRE(ox)+Analyte(red)→Product(ox)+MRE(red)
MRE(red)+$O_2$→MRE(ox)+$H_2O_2$
$H_2O_2$+Med(red)→2$H_2O$+Med(ox)
Med(red)+2e→Med(ox) [signal]

where: MRE(ox) is oxidized form of the oxidase MRE, MRE(red)—reduced form of the oxidase MRE, Med(ox)—oxidized from of redox mediator, Med(red)—reduced form of redox mediator.

In step 1, the oxidase MRE oxidizes the target analyte to produce a product and the MRE itself is reduced. In step 2, the reduced form of the MRE reacts with oxygen in order to produce hydrogen peroxide. In step 3, hydrogen peroxide is reduced into water while the reduced form of the redox mediator Med(red) is oxidized to Med(ox). In step 4, in the presence of an electric potential, the Med(ox) is reduced to regenerate Med(red) and a measurable detectable signal is produced in the form of current (electron flow). In some embodiments, the electrons are a detectable signal which can be measured as current (amperometrically).

A general reaction scheme 1 for identification of an oxidase MRE through electrochemical methods ($2^{nd}$ generation) can also be represented as shown in reaction scheme 2 as follows:

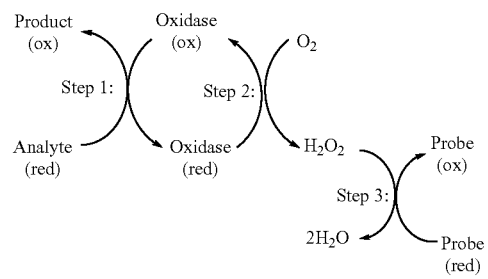

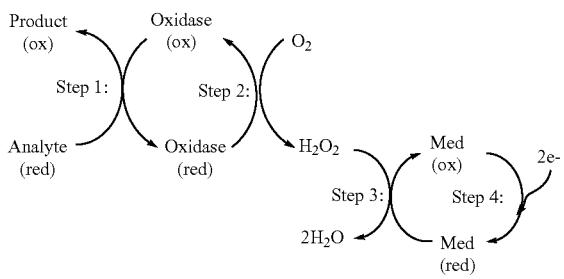

In some embodiments, the MRE can be identified through electrochemical methods ($1^{st}$ generation) as shown in reaction scheme 3 as follows:

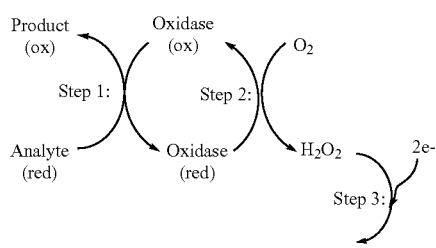

In some embodiments, the MRE can be identified through electrochemical methods ($3^{rd}$ generation) as shown in reaction scheme 3 as follows:

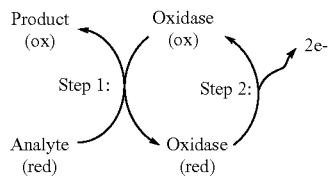

In some embodiments, the Med(red) can catalyze a redox reaction with a readout enzyme (ReadE) to convert a readout substrate (ReadS) into a readout product (ReadP), where the ReadP produces a detectable signal which can be measured optically, e.g., by fluorescence or other luminescence methods as shown in reaction scheme 4 as follows:

A) Redox-Mediators (Med)

In some embodiments, the redox-enzyme is not capable of measuring analyte directly. That is, a detectable signal is not produced when the candidate MRE interacts with the target analyte. Accordingly, while the analyte is detected and catalyzed by the MRE protein that is capable of interacting directly with the analyte molecule to produce a product, the MRE cannot transfer electrons, but rather it produces a redox mediator co-product. One such redox mediator is hydrogen peroxide ($H_2O_2$). Accordingly, some redox-enzymes, including MREs cannot exchange electrons directly with an electrode because their redox active sites are buried deep within the enzyme protein structure. Therefore, in order to transfer electrons between the redox active site of the enzyme and produce a detectable signal, a redox mediator (Med) also known as an "electron transfer agent" is used. In some embodiments, the analyte-specific enzyme is cross-linked to the electron transfer agent.

In some embodiments, redox mediators are electroreducible and electrooxidizable ions or molecules having redox potentials (voltages) that are a few hundred millivolts above or below the redox potential (voltage) of the standard calomel electrode (SCE). In some embodiments, the redox mediators are not more reducing than about −150 mV and not more oxidizing than about +400 mV versus SCE. Examples of suitable redox mediators are disclosed, for example, in Mao et al. (U.S. Pat. No. 6,605,200) the entire content of which is herein incorporated by reference.

Accordingly, the assay system disclosed herein comprises redox mediators (Med) that serve as electron carriers, or electron signal mediators. That is, they are multi-electron transfer mediators that function as electrochemically detectable signal mediators to produce a detectable signal when transfer of electrons occurs. Preferably a redox-mediator as disclosed herein is linearly to exponentially amplified by magnifying electrochemical signal output via recycling the enzyme substrates.

A redox-mediator can be any of the natural or synthetic mediators commonly used in biosensors known to date, and is preferably selected from the group consisting of cytochromes, quinones, aminophenols, electron-acceptor aromatic compounds (e.g., TTF=tetratiafulvalene and NMP=N-methylphenazine), electron-donor aromatic compounds (e.g., TCNQ=tetrakyano-p-quinodimethane), organic conductive salts (e.g., TTF.TCNQ=tetratiafulvalene-7,7,8,8-tetrakyano-p-quinodimethane and NMP.TCNQ=N-methylphenylene-7,7,8,8-tetracyano-p-quinodimethane), organic dyes, metallocenes, organometallic complexes of osmium, ruthenium and duct, inorganic iron complexes. In some embodiments, redox mediators are ferricyanide ferrocene, 1,1-dimethyl-ferrocene, hexacyanoferrate or hexacyanoferrate.

In some embodiments, the redox mediator is AUR as disclosed herein. Natural and artificial mediators are shown in table 1.

TABLE 1

| Natural mediators | Artificial mediators |
| --- | --- |
| Cytochrome a3 | Ferricyanide (hexacyanoferrate III) |
| Cytochrome c3 | 2,6-dichlorophenol |
| Cytochrome b | Indophenol |
| Ubiquitone | Ferrocene |
| Vitamin K2 | Phenazine |
| Rubredoxin | Methosulphate |
| Flavoproteins | Methylene blue |
| FAD-FADH$_2$ | Phtalocyannine |
| FMN-FNH$_2$ | Phenosafranine |
| NAD+-NADH | Benzyl violet |
| NADP+-NADPH | Methyl violet |
| PQQ-PQQH$_2$ | Ferredoxin |
|  | Prussian Blue |
|  | Nile blue |
|  | Meldola's Blue |
|  | NQSA |
|  | Potassium hexacyanoferrate |
|  | Potassium ferricyanide |
|  | Potassium ferrocyanide |
|  | PMS |
|  | Dichlorophenolindophenol |
|  | p-benzoquinone |
|  | o-phenylenediamine |
|  | 3,4-dihydroxybenzaldehyde |
|  | Potassium hexacyanoferrate (II) |
|  | Tetracyanoquinodimethane |
|  | Cobalt (II) phtalocyanine |

In some embodiments, the redox-mediator is catalyzed to directly produce a detectable signal that is fluorescence, bioluminescence, luminescence or produce an optical readout or detectable signal. In some embodiments, the redox mediator transfers electrons to a readout substrate (ReadS) in the presence of a readout enzyme to generate a readout product, where the readout product produces a detectable signal that is fluorescence, bioluminescence, luminescence or colorimetric.

B) Coupled Multi-Enzyme System Using Readout Enzymes

In some embodiments, the reaction between the candidate MRE and the target analyte is coupled to one or more additional enzymes, herein referred to as readout enzymes (ReadE) or also referred to as an intermediate redox enzyme (e.g., IRE) to form a multi-enzyme system for detection of the redox reaction between the target analyte and candidate MRE. For example, where the redox mediator (Med) is hydrogen peroxide, the presence of a peroxidase enzyme as a ReadE can rapidly transfer electrons from $H_2O_2$ to a readout substrate (ReadS) to produce a readout product (ReadP) which produces a detectable signal, thereby avoiding issues of auto-oxidation of the Med(ox) and increasing the accuracy of measurement of analyte concentration.

Accordingly, in some embodiments, the Med(ox) can catalyze a redox reaction with a readout enzyme (ReadE) to convert a readout substrate (ReadS) into a readout product (ReadP), where the ReadP produces a detectable signal which can be measured optically, e.g., by fluorescence or other luminescence methods.

In some embodiments, an MRE assay disclosed herein to detect an oxidase MRE also uses a readout enzyme (ReadE), also referred to herein as an intermediate redox-enzyme (IRE). For example, in the presence of hydrogen peroxide and a peroxidase enzyme as a ReadE, electrons are transferred from a readout substrate (ReadS) to $H_2O_2$ to produce a readout product (ReadP) which is a detectable signal.

In some embodiments, the assay to detect a MRE that is an oxidase, can comprise use of readout enzyme (ReadE), also referred to herein as an intermediate redox-enzyme (IRE), for example, a peroxidase enzyme, were the basic chemical transformation are shown with reference to an oxidase redox enzyme system in the following reaction scheme 3 below:

1) Analyte(red)+MRE(ox)→Product(ox)+MRE(red)
2) MRE(red)+$O_2$→MRE(ox)+$H_2O_2$ (Catalyzed by the MRE)
3) $H_2O_2$+ReadS(red)→2$H_2O$+ReadP(ox) (Catalyzed by the ReadE)

In step 1, the oxidase MRE oxidizes the target analyte to produce a product and the MRE itself becomes reduced. In step 2, the reduced form of the MRE reacts with oxygen to produce hydrogen peroxide and the oxidized form of the MRE. In step 3, the hydrogen peroxide, in the presence of the readout enzyme (ReadE), oxidizes the readout substrate (ReadS) to form the readout product (ReadP) which is itself a readable signal. In some embodiments, the ReadP is a signal which can be measured optically or by luminescence techniques such as by fluorescence or chemiluminescence, and the measurement can be correlated to the concentration of the analyte.

A general reaction scheme for identification of an oxidase MRE using a readout enzyme (ReadE), such as a peroxidase can also be represented as shown in reaction scheme 4 as follows:

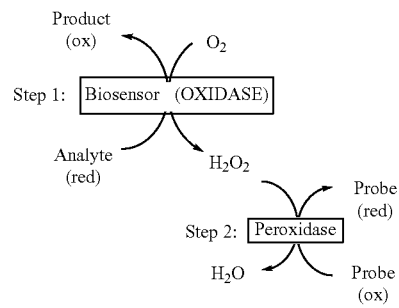

In some embodiments, the readout enzyme (ReadE) (also referred to as "intermediate redox-enzyme (IRE)") is a peroxidase enzyme, for example, but not limited to, APEX2 which, in the presence of hydrogen peroxidase, catalyzes the conversion of the readout substrate (ReadS) Amplex™ UltraRed (AUR) to the readout product (ReadP) resorufin, which produces a detectable signal. An exemplary reaction scheme for identification of an oxidase MRE using APEX2 as a peroxidase as a readout enzyme can be represented as shown in reaction scheme 5 as follows:

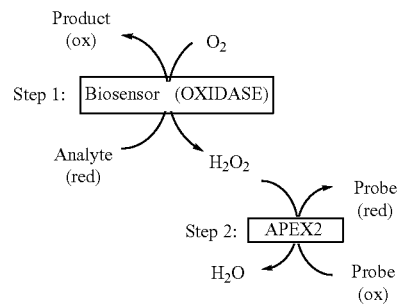

While the assay is exemplified using components and electrochemical reactions schemes to detect oxidase microbial redox-enzymes, the assay can be readily adapted for detection of dehydrogenase microbial redox-enzymes as disclosed herein.

One aspect of the technology described herein relates to a method to a method for identifying a microbial redox enzyme to a target analyte or an analyte of interest, comprising contacting a library of genomic DNA (gDNA) encoding one or more MREs with (i) a target analyte, and (ii) a redox mediator (Med), and optionally a readout enzyme and readout substrate (ReadS), wherein the target analyte is catalyzed in the presence of the MRE, converting the Med and where the readout enzyme (ReadE) transfers electrons from (Med) to a readout substrate (ReadS) to produce a readout product (ReadP), which produces a detectable signal, e.g., a fluorescent signal. By way of an illustrative example only, in some embodiments, the readout enzyme (ReadE) is a peroxidase enzyme, such as, but not limited to, ascorbate peroxidase (APEX2), and the readout substrate (ReadS) is, but not limited to, Amplex™ UltraRed (AUR), which produces a readout product (ReadP) resorufin, which is fluorescent, only in the presence of hydrogen peroxide ($H_2O_2$) and APEX2. In this illustrative example, cells containing a gDNA fragment encoding a MRE, such as an oxidase enzyme which degrades the analyte of interest will become fluorescent, because the oxidase will produce $H_2O_2$, a (Med) example, which is used as a substrate, along with AUR, for the peroxidase enzyme, APEX2 to produce the fluorescent readout product resorufin. Fluorescent droplets (in a cell-free assay), or fluorescent cells are then identified and sorted by a fluorescence-activated cell sorting (FACS) machine, and the gDNA can be sequenced to identify the gene responsible for encoding the MRE, e.g., the oxidase MRE that catalyzes the analyte of interest.

By way of an illustrative example only, in some embodiments, the readout enzyme is a peroxidase enzyme, such as, but not limited to, ascorbate peroxidase (APEX2), and the redox-mediator (Med) such as hydrogen peroxidase ($H_2O_2$), and the readout substrate (ReadS) is, but is not limited to, Amplex™ UltraRed (AUR), which produces a resorufin (readout product) which is a fluorescent product only in the presence of hydrogen peroxide ($H_2O_2$). In this illustrative example, cells containing a gDNA fragment encoding a MRE, such as an oxidase enzyme which degrades the analyte of interest will become fluorescent, because the oxidase MRE will produce $H_2O_2$, which is used as a substrate, along with AUR, for the readout enzyme (e.g., peroxidase enzyme) APEX2 to produce resorufin, which is a fluorescent product. Fluorescent droplets (in a cell-free assay), or fluorescent cells are then identified and sorted by a fluorescence-activated cell sorting (FACS) machine, and the gDNA encoding the redox-enzyme can be sequenced to identify the gene responsible for producing the redox-enzyme, e.g., the oxidase enzyme responsive to the analyte of interest.

APEX2 is an engineered ascorbate peroxidase enzyme that functions both as an electron microscopy tag and as a promiscuous labeling enzyme for live-cell proteomics. In some embodiments, APEX2 can be used as a readout enzyme to catalyze the generation of a fluorescent product from Amplex™ UltraRed (AUR) only in the presence of hydrogen peroxide ($H_2O_2$). Using AUR to measure intracellular $H_2O_2$ in *E. coli* requires the expression of functional horseradish peroxidase (HRP) in the cell, a task which has proven difficult in the reducing environment of the *E. coli* cytoplasm because HRP requires several disulfide bonds for activity (Grigorenko et al., 2015; Biochem (Mosc.) 80; 408-416; Lin et al., 1999; Biotech Prog. 15; 467-71). This exogenous expression of HRP in cells often results in the formation of intracellular inclusion bodies and requires laborious purification and downstream refolding steps to yield functional HRP enzyme (Egorov et al., 1994; Anny N Y Acc. Sci., 721; 73-81). The ascorbate peroxidase, APEX2, was engineered and does not require disulfide bonds, expresses efficiently in *E. coli*, and also oxidizes AUR in the presence of $H_2O_2$ (Lam et al., 2015; Nat Methods., 15; 51-4; Martell et al., 2012; Nat Biotechnol, 30; 1143-8). Accordingly, in some embodiments, APEX2 can be used, or another peroxidase which is active intracellularly and does not form inclusion bodies is encompassed in the MRE assay as disclosed herein.

In some embodiments, the assay, methods and composition as disclosed herein can also use modified version of the APEX2 enzyme, e.g., a modified APEX2 enzyme with improved enzyme kinetics or catalyzes a different HRP derivative (e.g., catalyzes a different substrate to AUR).

In some embodiments, the technology encompasses alternative or modified readout enzymes, for example, such as modifying the APEX2 enzyme to have improved enzyme kinetics or to use alternative peroxidase enzymes, or HRP derivatives as readout enzymes and readout substrates, respectively.

Accordingly, in some embodiments, the assay uses the readout substrate Amplex™ Red (AR) or Amplex™ UltraRed (AUR) that is converted to the readout product resorufin, which has fluorescence at 563-587 nm, in the presence of peroxidases horseradish peroxidase (HRP) or Apurinic/Apyrimidinic Endodeoxyribonuclease 2 (APEX2). In aternative embodiments, AUR as the readout substrate can be substituted for other readout substrates, for example, 3,3',5,5'-tetramethylbenzidine (TMB), HP Green, Tyramide labeled with tetramethyl rhodamine (TMR)+BSA, homovanilloic acid, dihydroethudium (DHE) (see, e.g., Żamojé, Krzysztof, et al. "Fluorescent probes used for detection of hydrogen peroxide under biological conditions." Critical reviews in analytical chemistry 46.3 (2016): 171-200); Rezende, Flávia, Ralf P. Brandes, and Katrin Schröder. "Detection of hydrogen peroxide with fluorescent dyes." Antioxidants & redox signaling 29.6 (2018): 585-602. Held, Paul. "An introduction to reactive oxygen species." Tech Resources-App Guides 802 (2012): 5-9)

Additionally, in some embodiments, the readout substrate (ReadS), such as AUR, can be replaced with other $H_2O_2$ responsive probes known in the art, for example, but not limited to PY1, PO1, Amplex™ UltraRed, Hemovanillic acid (HVA), Luminol, OPD, DCFH, ABTS, K iodide, or ABTS.

In some embodiments, other redox enzymes can be used as readout enzymes, for example, one of ordinary skill in the art can readily substitute APEX2 for another enzyme, or peroxidase enzyme which is sensitive to other enzyme products. In some embodiments, the technology encompasses alternative or modified readout enzymes, for example, such as modifying the APEX2 enzyme to have improved enzyme kinetics or to use alternative peroxidase enzymes, or HRP derivatives.

In some embodiments, the readout substrate (ReadS), such as AUR, can be replaced with other $H_2O_2$ responsive probes known in the art, for example, but not limited to PY1, PO1, Amplex™ UltraRed, Hemovanillic acid (HVA), Luminol, OPD, DCFH, ABTS, K iodide, or ABTS. In some embodiments, other accessory enzymes can be used, for example, the readout enzyme APEX2 can be substituted for another enzyme, or a peroxidase enzyme which is sensitive to other readout substrates (ReadS). As an illustrate example, if the candidate MRE were to be changed from an oxidase to a dehydrogenase, the product of interest would change to NAD, NADH, NADP, NADPH, PQQ, or $PQQH_2$. In such an example, possible enzyme products include NAD+, NADH, NADP+, NADPH, PQQ, $PQQH_2$, $O_2$, and $H_2O$. In some embodiments, the readout substrate (ReadS) is catalyzed to a readout product (ReadP) that produces a detectable signal that is fluorescence, bioluminescence, luminescence or produces an optical readout or detectable signal.

Other readout enzymes are encompassed for use in this assay system can be selected from a nicotinamide adenine dinucleotide (NAD(P))-dependent dehydrogenase, a flavin adenine dinucleotide (FAD)-dependent oxidase, or a flavin mononucleotide (FMN)-dependent oxidase. For example, in some embodiments, the IRE of this system is selected from 11β-hydroxysteroid dehydrogenase type 2 (11β-HSD-2), glucose oxidase, NAD-glucose dehydrogenase, FAD-glucose dehydrogenase, lactate oxidase, NAD(P)-lactate dehydrogenase, NAD(P)-alcohol dehydrogenase, pyruvate oxidase, NAD(P)-glutamate dehydrogenase, and xanthine oxidase.

Non-limiting examples of readout enzymes that can be coupled to the redox-reaction of the candidate MRE and the target analyte, can be selected from any of non-limiting examples of redox enzymes including, but are not limited to, glucose oxidase, lactate dehydrogenase and malic enzyme (malate dehydrogenase), fructose dehydrogenase, alcohol dehydrogenase, choline oxidase including but not limited to glutathione peroxidases, glutathione reductases, peroxiredoxins, thioredoxin reductases, glucose 6-phosphate dehydrogenase, catalase.

C) Alternatives to Using a Readout Enzyme to Detect $H_2O_2$

In some embodiments, the production of $H_2O_2$ can be assessed directly using other $H_2O_2$ probes, also referred to herein as "Hydrogen peroxide responsive probes". Other $H_2O_2$ probes include boronate-based probes, including but not limited to, 1a and 1b, PG1, PF1, RPF1, PC1, PY1-ME, PCL-1, F1-B, which are disclosed in Zamajc et al., Crit Rev. in analytical chemistry, 2016; 46 (3); 171-200, which is incorporated herein in its entity by reference. Such boronate-based probes do not need a catalyzing enzyme such as HRP or APEX2, rather they simply fluoresce in the presence of $H_2O_2$. Therefore, in a cell-based MRE screen, incubating cells expressing the MRE in the presence of an analyte and a boronate-based probe, if the cell comprises a MRE responsive to the target analyte, it will fluoresce and can be selected. Similarly, in a cell-free MRE system, droplets contacted with the target analyte and a boronate-based probe, droplets that fluoresce indicate that the droplet comprises a gDNA fragment comprising a candidate oxidase MRE. Exemplary boronate-based $H_2O_2$ responsive probes that can be used as readout substrates are shown in FIGS. 40A-40B and FIGS. 41A-41P.

In some embodiments, the $H_2O_2$ responsive probes which can be used as readout substrates (ReadS) are absorbance based probes, for example, such $H_2O_2$ probes can be selected from, for example, (i) reduced o-dianisidine, which is converted to oxidized o-dianiside in the presence of $H_2O_2$, which has absorbance of 440 nm, or (ii) 4-Aminoantipyrine (AA)+Phenol, which is converted to red quinoneimine chromagen in the presence of $H_2O_2$, which has an absorbance of 505 nm.

In some embodiments, the chemilumescent peroxidase-independent probes can be used as $H_2O_2$ probes or as ReadS in the methods and assays described herein, e.g., ROS-Glo $H_2O_2$ probes (commercially available from Promega), L-012 (Goiffon, Reece J., Sara C. Martinez, and David Piwnica-Worms. "A rapid bioluminescence assay for measuring myeloperoxidase activity in human plasma." Nature communications 6.1 (2015): 1-9).

In some embodiments, fluorescent peroxidase-independent probes can be used as $H_2O_2$ probes or as ReadS in the methods and assays described herein, can be selected from any of the following: CBA which is converted to COH (blue fluorescence) in the presence of $H_2O_2$, xylenol orange, fluorescein boronate (FL-B), Peroxyfluor-1 (PF1), Poly(9,9-bis(60-N,N,N-trimethylammonium-hexyl) fluorine phenylene) (PFP-NMe3+), PF1-Polyfluorene (PF-FB), Peroxyxanthone-1 (PX1), Peroxyresorufin-1 (PR1), Peroxy green 1 (PG1), Peroxy crimson 1 (PC1), NAP-tag (06-alkylguanine-DNA alkyltransferase (AGT)+organelle-targeting protein (OTP))+SNAP-Tag substrate, Peroxy orange 1 (P01), Peroxy yellow 1 (PY1), Peroxy yellow 1-methyl-ester (PY1-ME), Peroxy emerald 1 (PE1), Peroxyfluor-2 (PF2), Peroxyfluor-3 (PF3), Peroxyfluor-6 (PF6), Peroxyfluor-6 acetoxymethyl ester (PF6-AM), Mitochondria peroxy yellow (MitoPY1), Nuclear peroxy emerald 1 (NucPE1), Ratio-peroxyfluor-1 (RPF1), 7-amino-4-methyl-coumarin, dimethylaminocinnamaldehyde-linked arylboronate, Naphtho-peroxyfluor-1 (NPF1), Naphthofluorescein disulfonate (NFDS1), Naphthofluorescein disulfonate (NFDS1), Peroxy naphthalene 1 (PN1), SHP-Mito, 1,8-naphthalimide fluorophores, 4-hydroxy-1,8-naphthalimide+ hydrophilic 2-(2-hydroxyethoxy)ethyl group at imide moiety, Peroxy lucifer 1 (PL1), HP green, Ratiometric fluorescent $H_2O_2$ probes, Selenium-contained aggregation-induced "turn-on" fluorescent probe (D-HMSe), D-BBO, 2-(2'-Hydroxyphenyl)benzoxazole (HBO), Quinoline-based fluorescent probe (DQHP), Reversible fluorescent probe, 7-Hydroxy-2-oxo-N-(2-(diphenylphosphino)ethyl)-2H-chromene-3-carboxamide (DPPEA-HC), NBzF, Pentafluorobenzenesulfonyl fluoresceins, $Eu^3C$-tetracycline complex [Eu(tc)], Terpyridene europium(III) complex, Iron-based complexes, named MBFh1, MBFh2, and MBFh3, PPESO3, Diketopyrrolpyrrole-tellurophene conjugate probes, Zinpyr-1 (ZP1), DA-Cy, Two fluorescein disulfonate compounds (FS-1 and FS-2), 2',7'-Dichlorodihydrofluorescein (DCFH), DCFH-DA, & CM-DCFHDA, Cyanine fluorochrome, FP—$H_2O_2$—NO, N,N,$N^1$,$N^1$-[2,6-(3'-aminomethyl-1'-pyrazolyl)-4-(3",4"-diaminophenoxy)methylene-pyridine]tetrakis(acetate)-$Tb^{3+}$(BMTA-Tb3") (see, e.g., Żamojć, Krzysztof, et al. "Fluorescent probes used for detection of hydrogen peroxide under biological conditions." Critical reviews in analytical chemistry 46.3 (2016): 171-200 which is incorporated herein in its entirety by reference).

In some embodiments, the $H_2O_2$ responsive probes which can be used as readout substrates (ReadS) are chemilumesence based probes, for example, such $H_2O_2$ probes can be selected from any of: Peroxy caged luciferin-1 (PCL-1), terbium peroxy reporters (TRP1 and TRP2), however, these probes require peroxidase readout enzymes for the catalysis.

Protein $H_2O_2$ responsive probes: In some embodiments, $H_2O_2$ produced by a candidate MRE can be detected by a transcription factor (TFs) as an alternative to boronate-based $H_2O_2$ probe or as an alternative to a readout enzyme, where the transcription factor responds to the produced $H_2O_2$.

In some embodiments, transcription factors (TFs) can be used to respond to the produced $H_2O_2$. In some embodiments, OxyR, a TF responsive to $H_2O_2$, can be used to regulate and induce GFP expression downstream of an OxyR binding site. In some embodiments, the transcription factor coupled to detect the interaction of the target analyte and the MRE is OxyR, which is a transcription factor responsive to $H_2O_2$, and in some embodiments, be used to regulate and induce gene expression, such as GFP expression, downstream of an OxyR binding site. In some embodiments, OxyR can be expressed in a cell of the cell-based MRE assay, similar to how the cell was modified to express APEX2. In another embodiment, the other variation to the technology described herein is use transcription factors (TFs) responsive to $H_2O_2$. In one embodiment, OxyR, a TF responsive to $H_2O_2$ can be used to regulate GFP expression downstream of its binding site.

OxyR

In one embodiment, OxyR, a TF responsive to $H_2O_2$ can be used to regulate GFP expression downstream of its binding site. OxyR encodes a transcription factor that senses $H_2O_2$ and is activated through the formation of an intramolecular disulfide bond. OxyR activates the expression of a regulon of hydrogen peroxide-inducible genes including but not limited to katG, gor, ahpC, ahpF, oxyS, dps, fur and grxA. OxyR expression is negatively autoregulated by binding to a 43 bp region upstream of its own coding sequence. OxyR is inactivated by reduction of its essential disulfide bond by the product of GrxA, itself positively regulated by OxyR. The following sequence of OxyR is provided: OxyR amino acid-encoding polynucleotide sequence, e.g.

```
P0ACQ4-1 (SEQ ID NO: 1):
MNIRDLEYLVALAEHRHFRRAADSCHVSQPTLSGQIRKLEDELGVMLLER

TSRKVLFTQAGMLLVDQARTVLREVKVLKEMASQQGETMSGPLHIGLIPT

VGPYLLPHIIPMLHQTFPKLEMYLHEAQTHQLLAQLDSGKLDCVILALVK

ESEAFIEVPLFDEPMLLAIYEDHPWANRECVPMADLAGEKLLMLEDGHCL

RDQAMGFCFEAGADEDTHFRATSLETLRNMVAAGSGITLLPALAVPPERK

RDGVVYLPCIKPEPRRTIGLVYRPGSPLRSRYEQLAEAIRARMDGHFDKV

LKQAV
```

Other genetically-encoded hydrogen peroxide probes can be used, which include, without limitation, Hyper1, Hyper2, Hyper3, HyPer-Red, roGFP-Orpl, roGFP-Tsa2. Exemplary genetically-encoded hydrogen peroxide probes are disclosed in Rezende et al., Detection of Hydrogen Peroxide with fluorescent dye, Antioxidants and Redox signaling;2018; 29(6), 585-602. Accordingly, in some embodiments, these genetically-encoded hydrogen peroxide probes can be expressed in a cell of the cell-based MRE assay, similar to how the cell was modified to express APEX2.

IV. Assay Systems for Detecting Dehydrogenase Redox-Enzymes

While assay systems used to identify oxidase microbial redox-enzymes are exemplified herein, it is envisioned that the MRE assays can be used for identification and detection of other redox-enzymes. That is, while the examples exemplify using components and electro-chemical reactions schemes to detect an oxidase MREs, the assay can be readily adapted by one of ordinary skill in the art for detection of a NAD(P)-dehydrogenase or NAD(P)-independent dehydrogenase enzyme MREs as disclosed herein.

Electronic coupling of the dehydrogenase as the redox enzyme can be accomplished through the involvement of a quinone, which shuttles electrons between the dehydrogenase enzyme and electrode or redox-mediator. In some embodiments, a redox-mediator, ubiquinone-6 (coenzyme Q-6), is used as a means to couple FDH to the electrode electronically. In addition to ubiquinone, other mediators based on quinones, such as menaquinone, are suitable for use in the present invention. Other chemistries based on well-known redox dyes such as dichlorophenol indophenol and phenazine methosulfate are also suitable for use.

As an illustrate example, if the candidate redox-enzyme being assessed using the assay system as disclosed herein is changed from an oxidase to a dehydrogenase, the product of interest would change to NAD(P) or NAD(P)H. In such an example, possible enzyme products include NAD+, NADH, NADP+, NADPH, $O_2$, and $H_2O$. In some embodiments, transcription factors (TFs) can be used to respond to the produced $H_2O_2$. In some embodiments, OxyR, a TF responsive to $H_2O_2$, can be used to regulate and induce GFP expression downstream of an OxyR binding site.

Figure 4A:
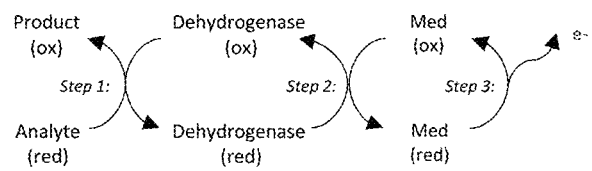
FIGS. 4A-4F shows exemplary redox reaction schemes for detection of dehydrogenase MREs.
Figure 4B:
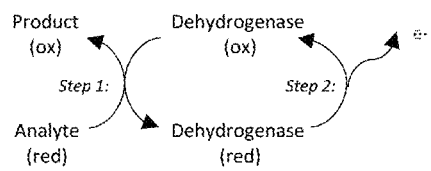
Figure 4C:
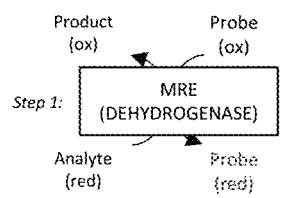

A general reaction scheme for identification of a dehydrogenase redox-enzyme that can be used as biosensor is shown in FIG. 4A, can be represented as shown in reaction scheme 6 as follows:

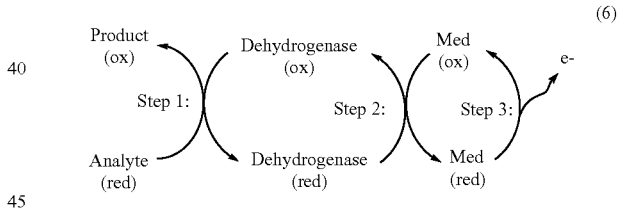

(6)

In some embodiments, the Med(red) is used to directly produce a detectable signal.

Figure 4D:
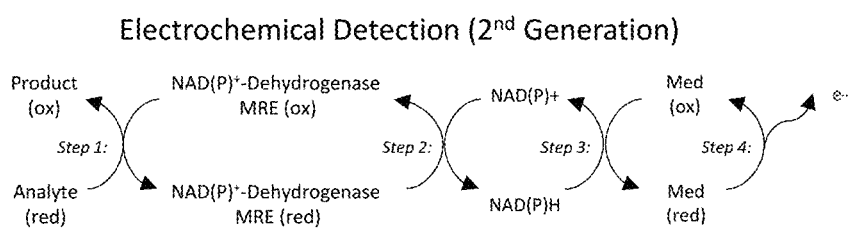
Figure 4E:
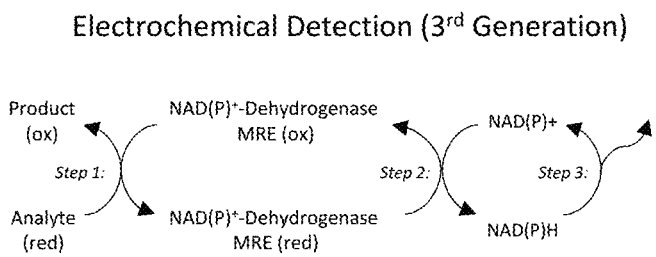
Figure 4F:
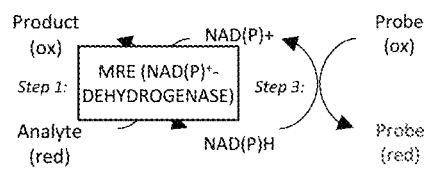
Figure 5A:
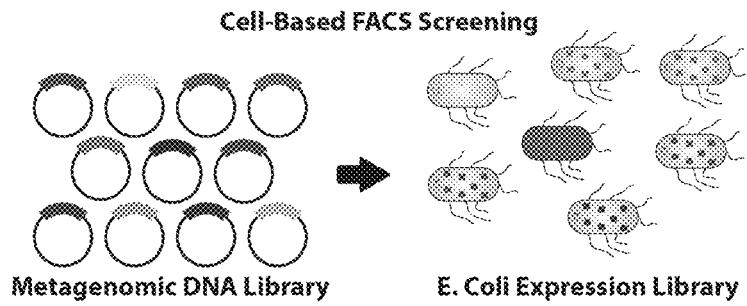
FIGS. 5A-5C show schematics of an exemplary assay to detect a MRE.
Figure 5B:
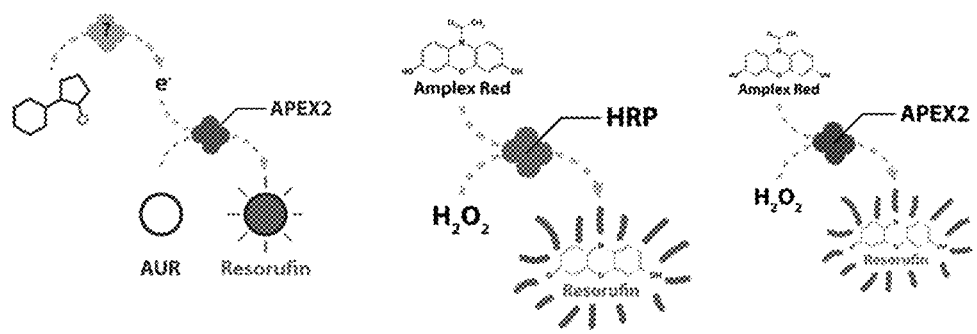
Figure 5C:
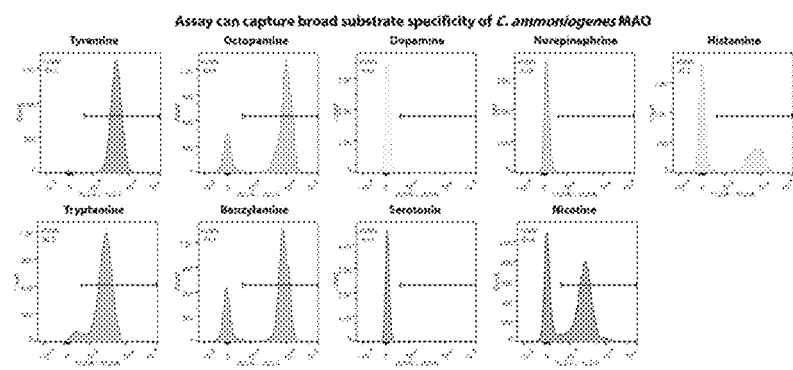
Figure 6:
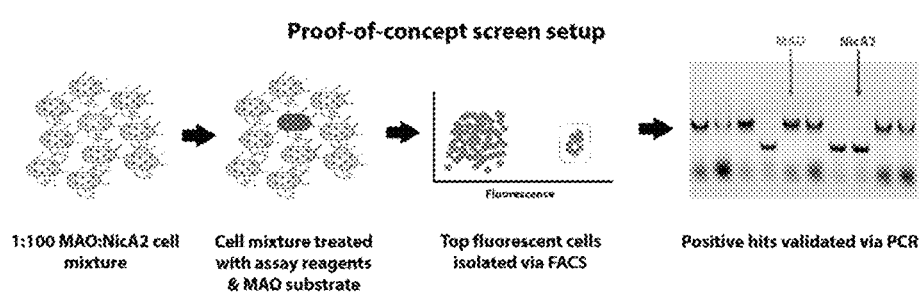
FIG. 6 is a schematic of the MRE assay disclosed herein and shows exemplary results of PCR results of the expression of MAO and NicA2 in isolated fluorescent cell populations isolated from the assay, demonstrating the assay is functional and can be used to identify cells that express each of the exemplary MRE, NicA2 and MAO.
Figure 7A:
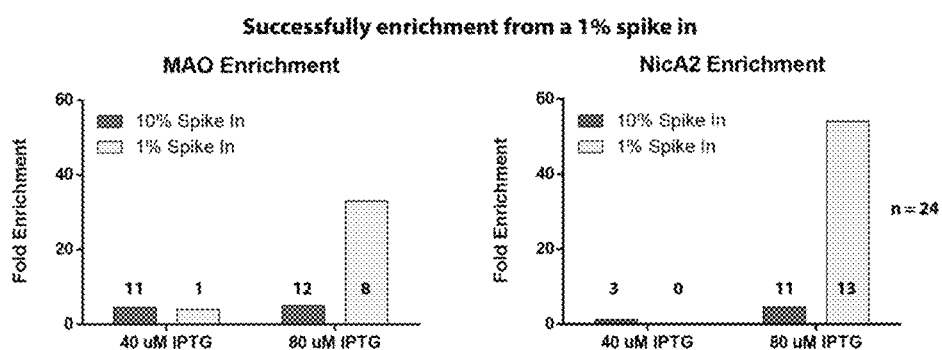
Figure 7D:
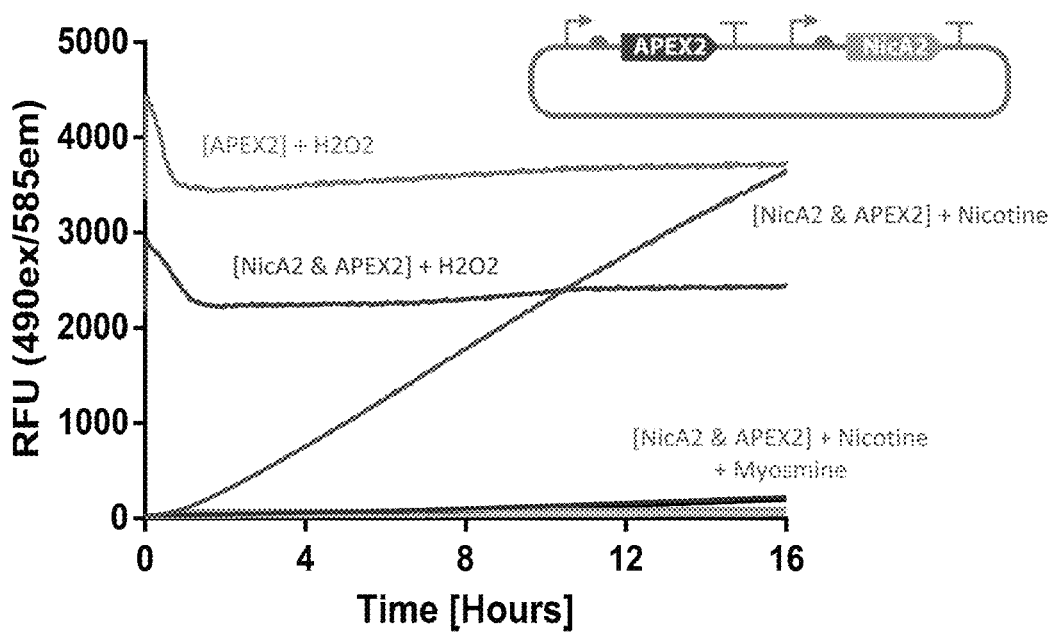
Figure 8A:
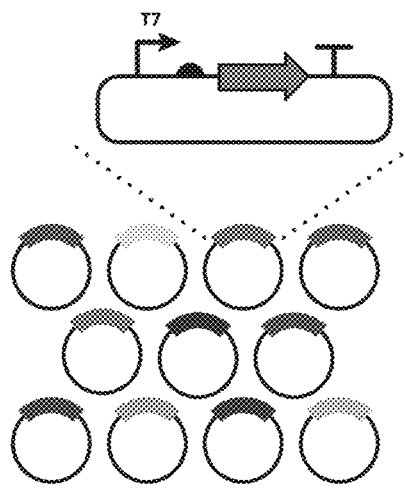
FIGS. 8A-8D show exemplary constructs for expression of MREs from the library.
Figure 8B:
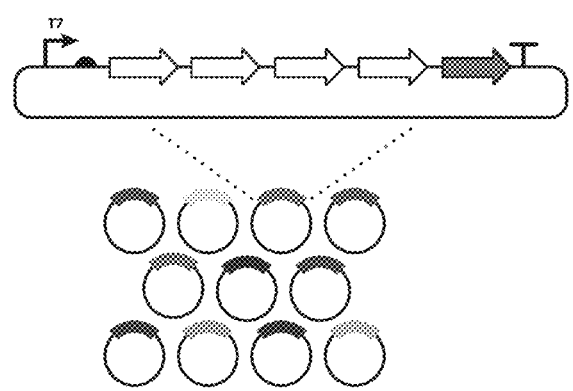
Figure 8C:
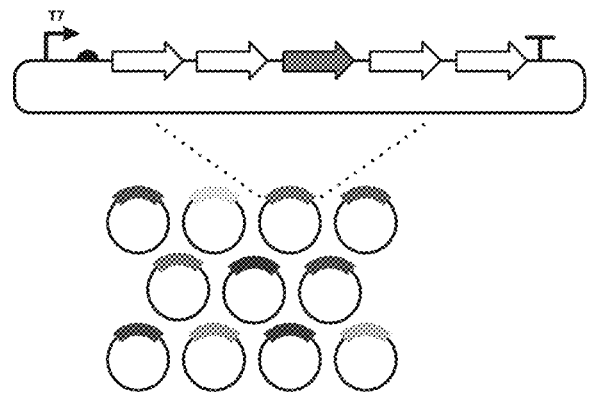
Figure 8D:
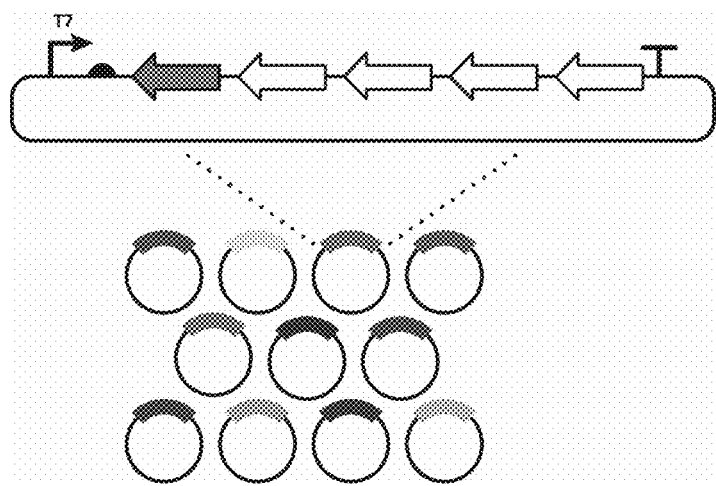
Figure 9A:
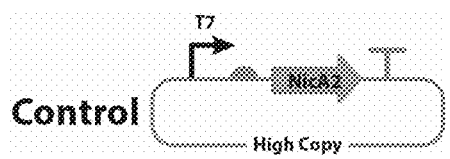
FIGS. 9A-9D show exemplary constructs with a high copy number vector backbone and gene fragments either comprising a MRE or gDNA fragments encoding a potential candidate MRE.
Figure 9B:
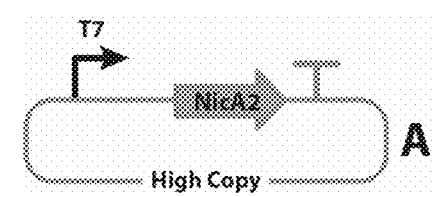
Figure 9C:
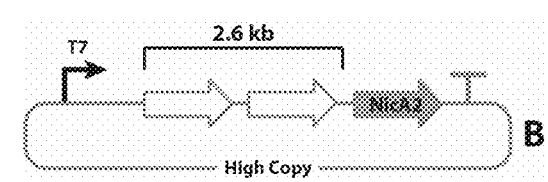
Figure 9D:
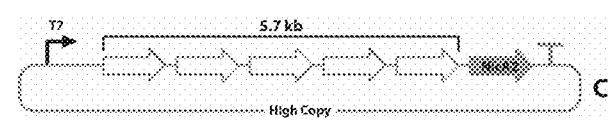
Figure 10A:
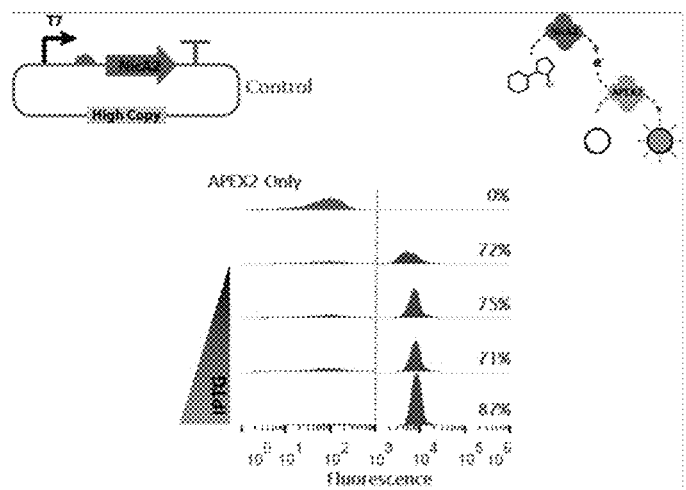
FIGS. 10A-10D show results of FAC sorting of constructs from FIGS. 9A-9D.
Figure 10B:
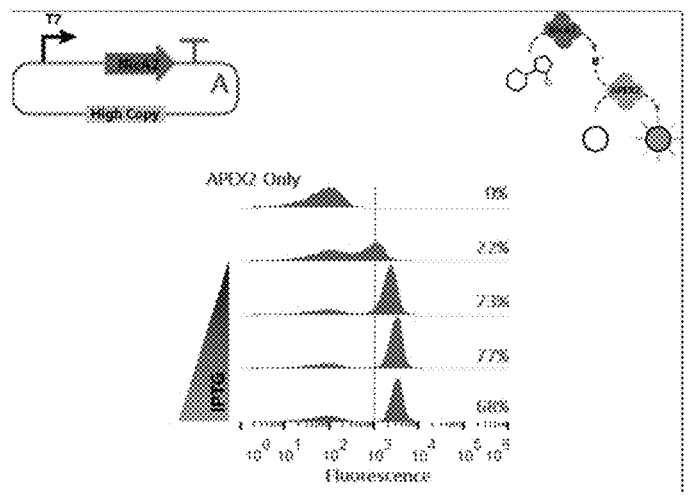
Figure 10C:
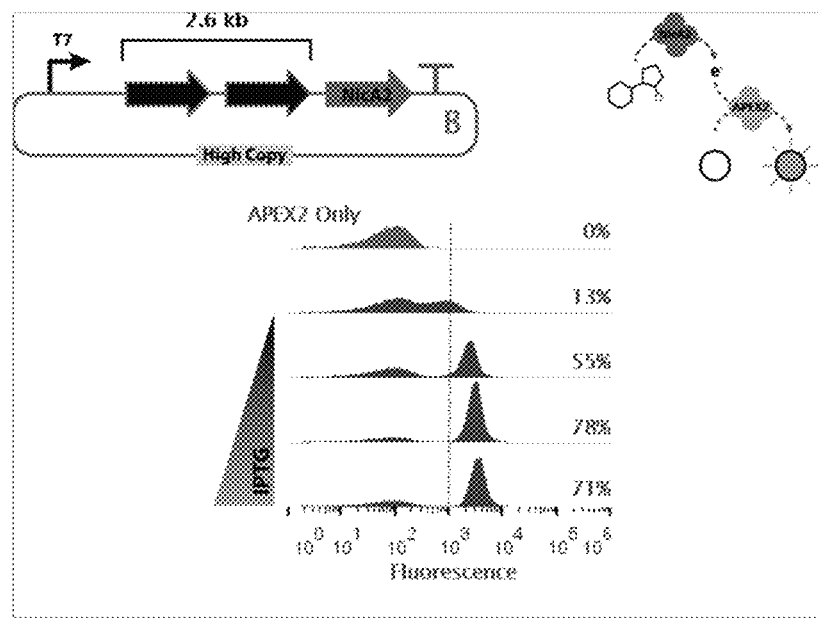
Figure 10D:
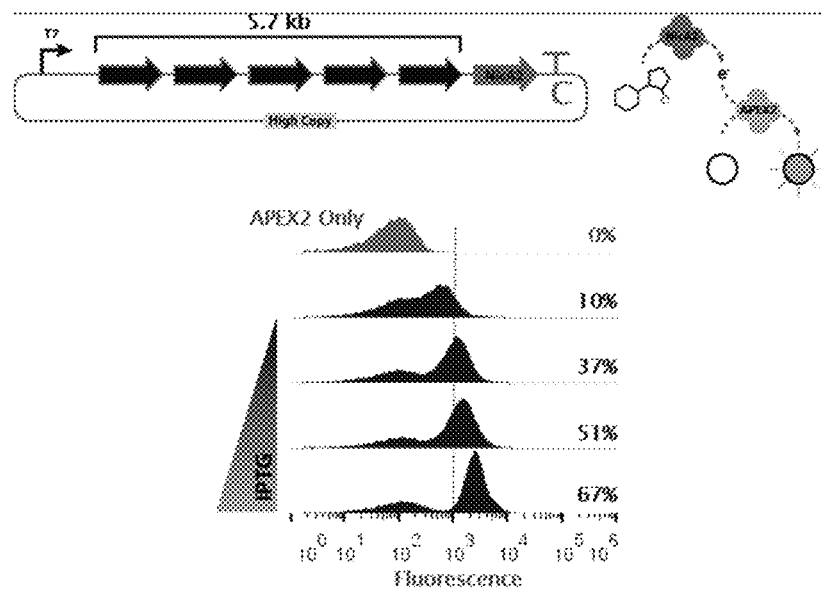
Figure 11A:
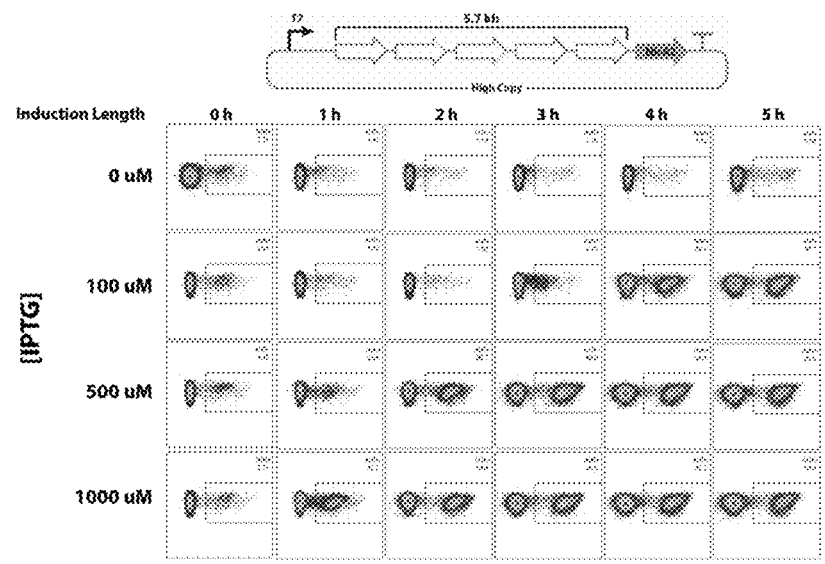
FIGS. 11A-11B show results of FAC sorting of construct from FIG. 9D and FIG. 10D.
Figure 11B:
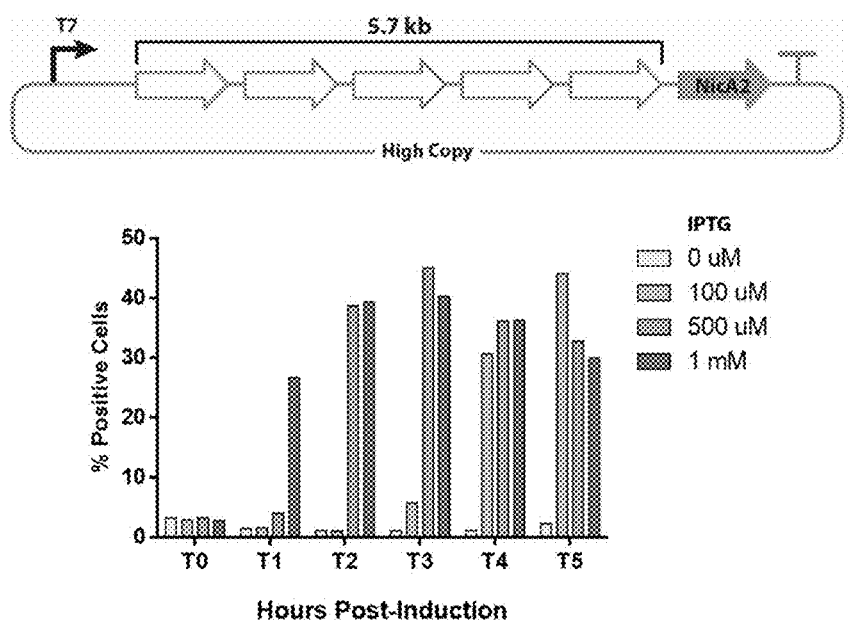
Figure 12A:
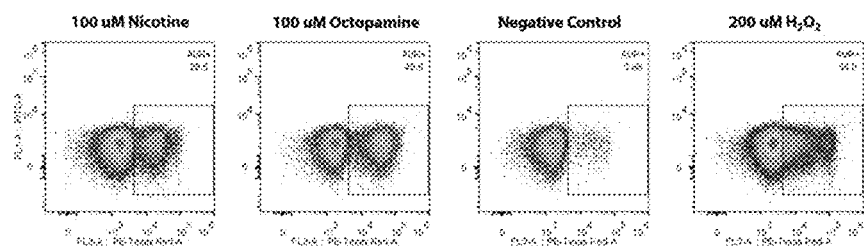
FIGS. 12A-12B show FACS results using different analytes.
Figure 12B:
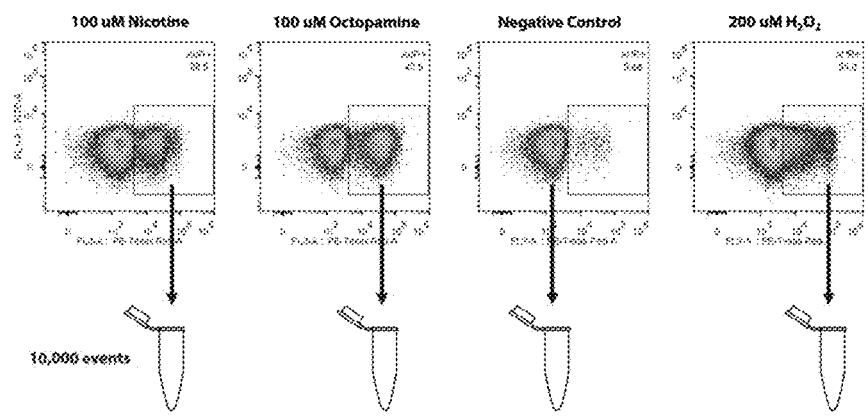
Figure 13A:
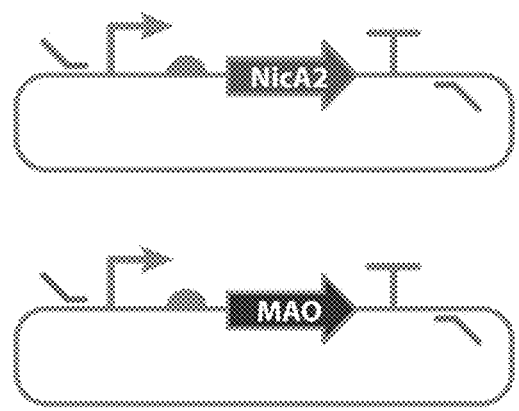
FIG. 13A-13B shows the FACS screening platform experimental setup that can be verified by next generation sequencing (NGS).
Figure 13B:
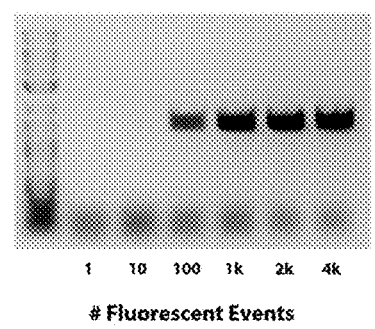
Figure 14A:
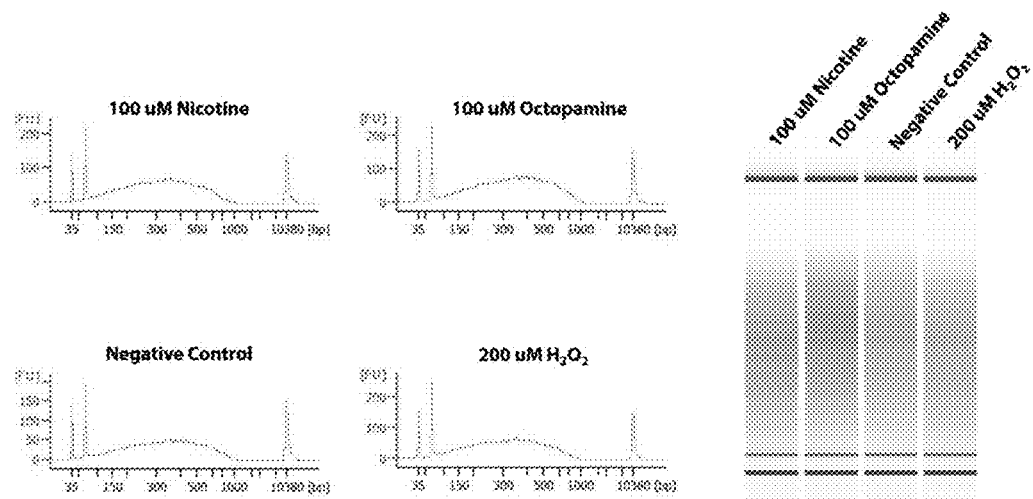
FIGS. 14A-14B show optimized PCR product fragmentation, and next generation sequencing (NGS) reads aligning to their corresponding redox enzyme and the level of enrichment.
Figure 14B:
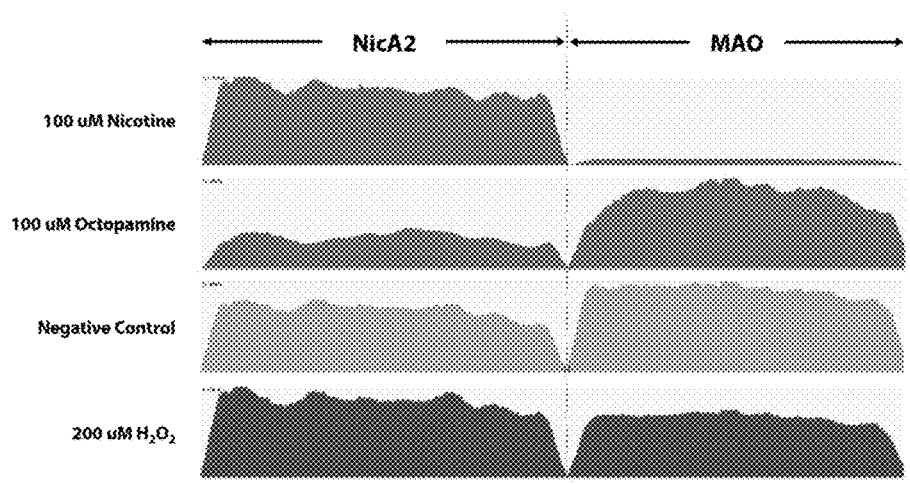
Figure 15A:
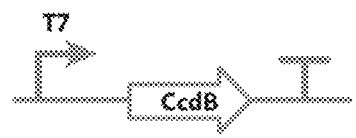
FIG. 15A-15B depicts an exemplary first iteration of metagenomic (gDNA) library construction design.
Figure 15B:
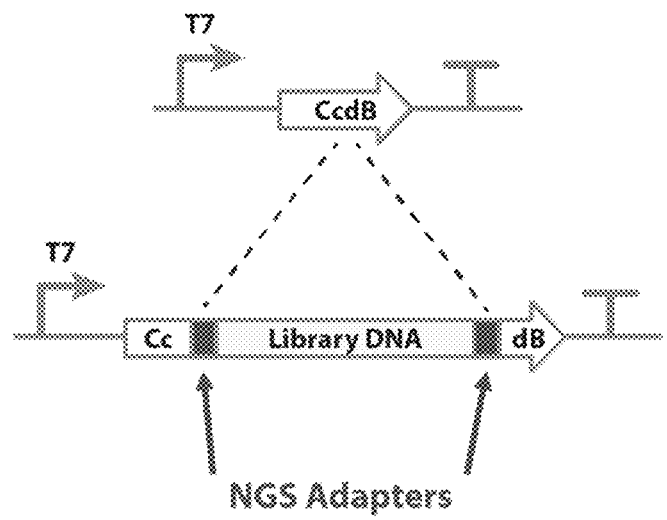
Figure 16A:
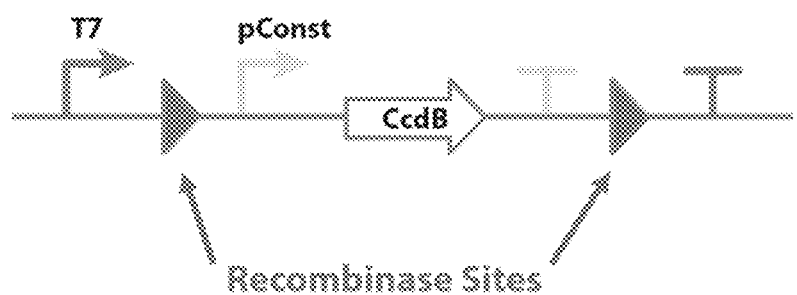
FIG. 16A-16B shows an improved gDNA library construction design.
Figure 16B:
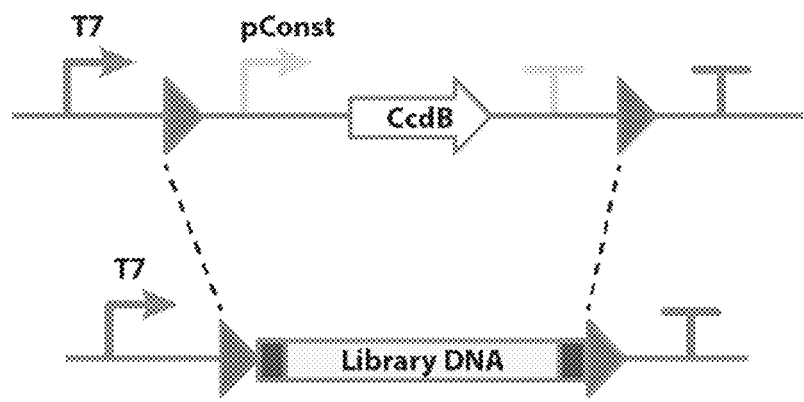
Figure 17A:
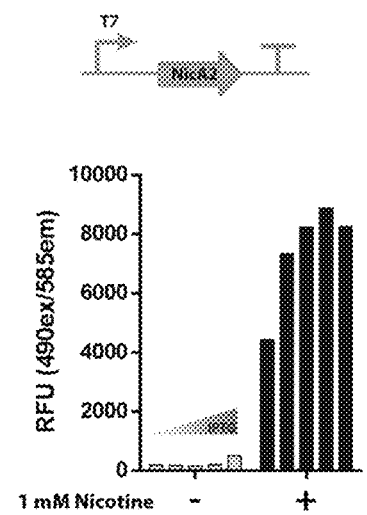
FIGS. 17A-17B show results of expression from the vector constructs shown in FIG. 15B and FIG. 16B.
Figure 17B:
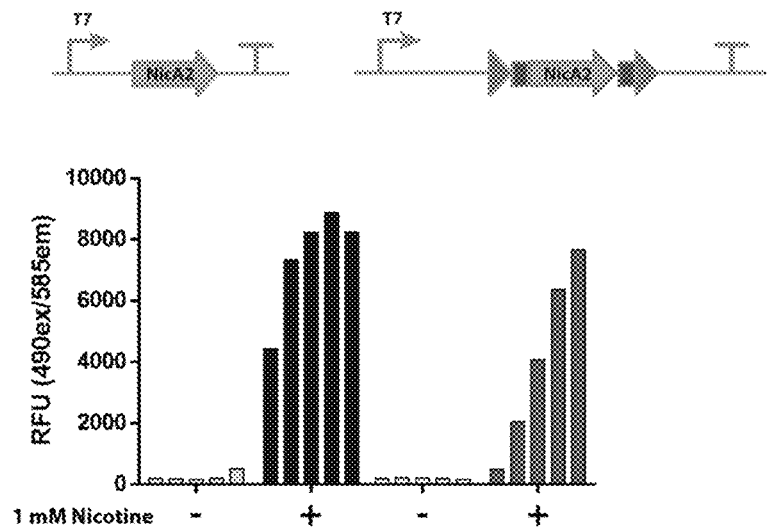

A general reaction scheme for identification of a NAD(P)-dehydrogenase redox-enzyme that can be used as biosensor is shown in FIG. 4D, can be represented as shown in reaction scheme 7 as follows:

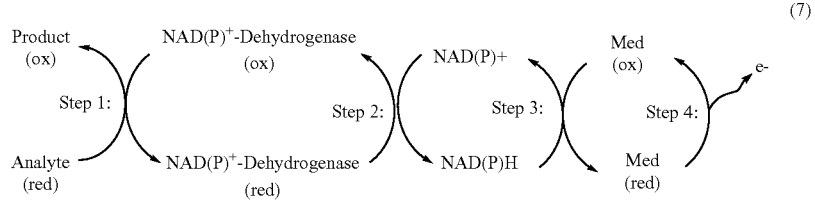

(7)

Non-limiting examples of enzyme products include but are not limited to enzyme products include NAD+, NADH, NADP+, NADPH, $O_2$, and $H_2O$.

An oxidase is an enzyme that catalyzes an oxidation-reduction reaction, especially one involving oxygen ($O_2$) as the electron acceptor. In reactions involving donation of an electron, oxygen is reduced to hydrogen peroxide ($H_2O_2$).

Accordingly, in another aspect of the technology described herein relates to a method or assay for identifying a MRE from an environmental source, wherein the redox enzyme is a NAD(P)-dehydrogenase, NAD(P)-independent dehydrogenase enzyme. the method or assay comprising: (a) contacting the protein products of the genomic DNA (gDNA) library with an analyte of interest, wherein the protein products are generated from the genomic DNA library obtained from a biological or an environmental source and (b) contacting with at least one of: (i) a peroxidase enzyme and a peroxidase responsive probe (PRP), wherein the peroxidase responsive probe can be oxidized from a reduced form (PRPred) to an oxidized form (PRPox) in the presence of the peroxidase enzyme and hydrogen peroxide, wherein the PRPox produces a detectable signal, (ii) NAD(P)-dependent probes (NAD(P)-DP), wherein the NAD(P)-dependent probe can be oxidized from a reduced form (NAD(P)-DPred) to an oxidized (NAD(P)-DPox) form in the presence of a NAD(P)-dehydrogenase enzyme to produce a detectable signal; (iii) a NAD(P)-independent responsive probe (NIP), wherein the NAD(P)-independent probe can be reduced from oxidized form (NIPox) to a reduced form (NIPred) to produce a detectable signal; and (b) measuring the presence of a signal produced from any one of RPRox, NAD(P)-DPred or NIPred, wherein: (i) RPRox is produced when the analyte is catalyzed by an oxidase redox-enzyme, (ii) NAD(P)-DPred is produced when an analyte is catalyzed by a dehydrogenase enzyme, (iii) NIPred is produced when an analyte is catalyzed by a NAD(P)-independent dehydrogenase enzyme, (c) isolating the gDNA from which a signal from of RPRox, NAD(P)-DPred or NIPred was produced, (d) sequencing the gDNA to identify the redox-enzyme that catalyzes the analyte of interest, wherein the redox-enzyme is an oxidase enzyme, a dehydrogenase enzyme or a NAD(P)-independent dehydrogenase enzyme.

V. High-Throughput Screening to Identify Redox-Enzymes

In some embodiments, the technology described herein relates to a high throughput assay (HTA), and in some embodiments, an ultra-high throughput microfluidic screening platform for the discovery of MREs, as well as an automated characterization processes necessary for enzyme validation via liquid handling robots. The platform requires two inputs from the user: a nucleic acid probe (e.g. a genomic DNA (gDNA) library) from which to screen for novel MREs, and an analyte of interest. Given these two inputs, the platform detects candidate MREs responsive to the analyte of interest and separates out the DNA which contains the candidate redox-enzyme which can be sequenced downstream and used to as redox-enzyme.

A) Cell-Based MRE Assays

In some embodiments, the screening is screening a gDNA library which is cloned into bacterial cells, e.g., *E. coli* cells. In some embodiments, the bacterial cells can also express components of the assay, for example, the readout enzyme, e.g., peroxidase enzyme as disclosed herein. In some embodiments, the cells comprise two plasmids, one expressing the readout enzyme, and one comprising a fragment of gDNA from environmental source, operatively linked to a promoter.

B) Optimization of Cell-Based MRE Assays

As disclosed herein, the inventors discovered that because the cell-based assay MRE selects for cells with increased oxidative stress as a result of the active MRE catalyzing a target analyte and thus producing hydrogen peroxide, there is significantly reduce viability of the cells being positively selected for. Accordingly, as shown in FIGS. 33-36, the inventors optimized multiple parameters of the cell based MRE assay to enable functional identification of MREs in a cell-based system.

In one embodiment, the technology relates to an optimized the cell-based MRE assay. Importantly, the inventors discovered that the viability of cells expressing a MRE significantly decreases in the presence of that MRE's target analyte. Therefore, as described herein in the Examples, the inventors had to rigorously and carefully optimize the assay, including optimizing multiple different parameters to increase the viability of the cells being selected for. Stated differently, as the cell-based MRE assay selects for bacterial cells comprising an active redox-enzyme to a target analyte, the cell has an increased oxidative stress level and/or increased ROS, which can lead to decreased viability. In essence, before optimization, the assay selects for cells that are dying or have reduced viability due to high ROS. In order to avoid this decrease this cell death and increase the viability of the cells to be selected thus enabling for selection of cells comprising an active MRE, the inventors optimized multiple parameters, including but not limited to, bacterial cell species, FACs parameters, others. As shown in FIG. 35B, the inventors assessed analyte toxicity, presence of antioxidants, treatment media, FAC sorting modes and FACS chip nozzle width, anaerobic vs. aerobic incubation, post-sort media and post-sort temperature in order to optimize the MRE assay to increase viability of cells expressing a MRE specific to a target analyte. Therefore, the optimized cell-based MRE assay described herein enables selection of cells expressing a MRE to the target analyte without a decreased cell viability.

Accordingly, in some embodiments, the cell-based MRE assay is optimized where FACs sorting uses a nozzle width having a range of 100 μm-130 μm in diameter. In some embodiments, the cell-based MRE assay is optimized where the cells are incubated pre- and/or post-sorting, in anaerobic conditions. In some embodiments, the cell-based MRE assay is optimized where there is a larger drop-sort volume. In some embodiments, the cell-based MRE assay is optimized so that the gDNA fragment encoding a MRE protein is under the control of an inducible promoter, e.g., a promoter responsive to IPTG, where the IPTG concentration is 10 μM. In some embodiments, the cell-based MRE assay is optimized where the AUR concentration is 5 μM. In some embodiments, the cell-based MRE assay is optimized where the cells are contacted with IPTG for 17 h and AUR for 6 h.

As disclosed herein, the isolated plasmids containing a gDNA or eDNA (see, e.g. FIG. 1A) is transformed into a strain of *E. coli*. In some embodiments, the *E. coli* strain is Rosetta2 (DE3). In some embodiments, the plasmids are transformed into C41 *E. coli* strain. Alternative bacterial *E. coli* strains encompassed for use include, but are not limited to, Origami2, Shuffle, Rosetta-Gami, BL-21 (DE3), Artic Express, Tuner (see, e.g., FIG. 36A). In some embodiments, the *E. coli* strain used has been modified to constitutively express an engineered ascorbate peroxidase, APEX2. Ascorbate peroxidase (or APX) is a member of the family of heme-containing peroxidases. Heme peroxidases catalyze the $H_2O_2$-dependent oxidation of a wide range of different, usually organic, substrates in biology.

Bacterial cells containing a gDNA fragment encoding an oxidase MRE which degrades the analyte of interest become fluorescent due to the production of $H_2O_2$ by the oxidase MRE. This is because $H_2O_2$ becomes a substrate, along with the readout substrate AUR for APEX2 to produce resorufin, which is a fluorescent readout product. In some embodiments, the APEX2 is under the control of a medium strength promoter.

As described herein, fluorescent cells are then identified and sorted by a fluorescence-activated cell sorting (FACS) machine. In some embodiments, the selected cells will then be grown in 2xYTP media and plated on carbenicillin agar plates overnight. The colonies can then be inoculated into fresh LB media with carbenicillin and their plasmids isolated (e.g. Qiagen #27104). Isolated plasmids will be sequenced to identify the gene responsible for producing the oxidase enzyme responsive to the analyte of interest.

In one embodiment, the gDNA library can be grown in 2xYTP media to mid-log phase and then encapsulating individual bacterial cells in nL sized droplets of fresh media using an in-house fabricated microfluidic droplet generator device. Cells within droplets would then be incubated at 37° C. to allow for cell growth for 2 hours, followed by addition of 100 µM AUR with the analyte of interest to be screened at 1 mM via picoliter injection or droplet merging. Merged droplets will be incubated for 3 hours within the microfluidic device to allow for enzyme-mediated degradation of the molecule of interest which will result in a fluorescent signal accumulation within the cell due to AUR reduction by APEX2. Droplets can then be sorted based of fluorescence intensity, pooled into a collection tube, and DNA extracted using a commercially available kit (e.g. Qiagen #27104). Purified DNA will be re-transformed into *E. coli* TOP10 (Thermo Fisher Scientific #C404010) via electroporation, and individual colonies will be grown in liquid culture overnight at 37° C. Plasmid DNA from these cultures will be purified and sequenced for identification of oxidase enzymes.

Bacteria have evolved over 3 billion years to detect and respond to virtually all classes of stimuli relevant to our own biology, including steroid hormones. Steroid utilizing bacteria have been isolated from diverse sources including activated sludge from wastewater, soil, composts, aquifers, sea waters, and the human microbiome. One mechanism by which bacteria sense stimuli is via oxidase enzymes.

C) Cell-Free MRE Assays and Systems

Figure 2A:
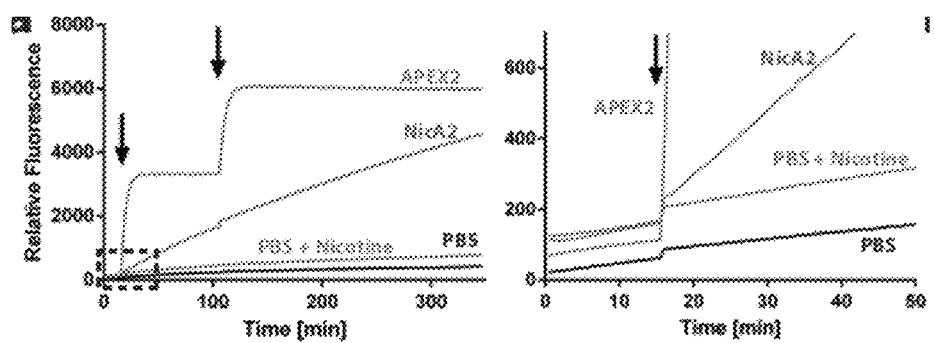
FIGS. 2A-2B shows two identified redox enzymes.
Figure 2B:
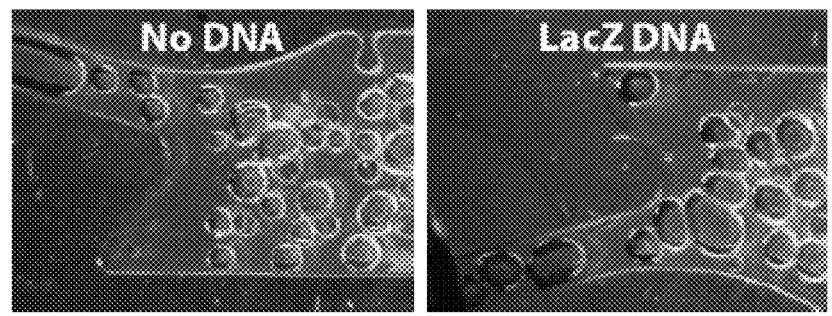
Figure 3A:
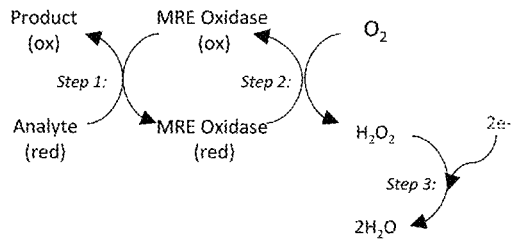
FIGS. 3A-3F shows exemplary redox reaction schemes for the MRE assay to detect oxidase MREs.
Figure 3B:
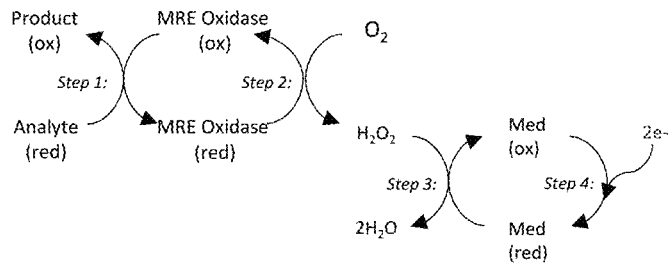
Figure 3C:
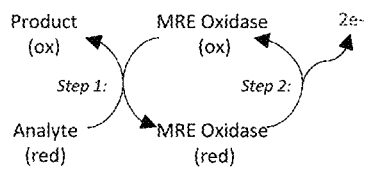
Figure 3D:
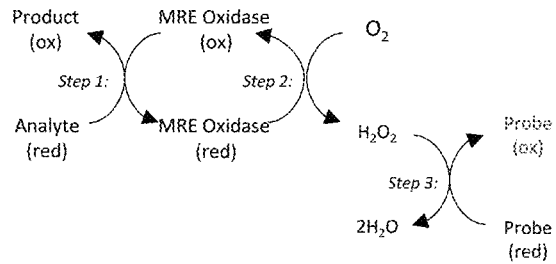
Figure 3E:
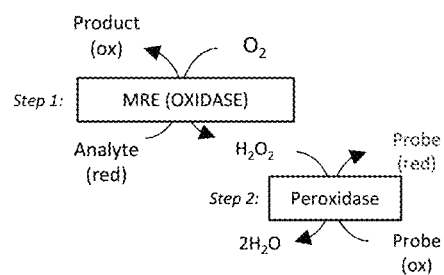
Figure 3F:
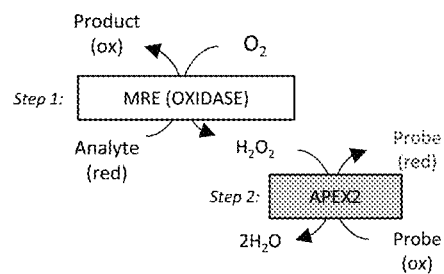

In one embodiment, the MRE assay is in a cell-free system, where a microfluidic device will segregate members of the eDNA or gDNA library into individual droplets containing a cell-free protein synthesis mix to express proteins encoded by the eDNA or gDNA fragments. If the gDNA or eDNA fragments comprises a candidate MRE, if the expressed MREs can degrade an analyte of interest it will generate redox mediator (Med) product (e.g. $H_2O_2$) that is used in the subsequent redox reaction which is catalyzed by a readout enzyme of a readout substrate (ReadS) which is converted to a readout product (ReadP) resulting in the emission of a fluorescent signal (see, e.g. FIG. 2A and FIG. 2B).

Some enzymes do not need additional components to show full activity. Others require non-protein molecules called cofactors to be bound for activity. Cofactors can be either inorganic including but not limited to metal ions and iron-sulfur clusters or organic compounds including but not limited to flavin and heme. These cofactors serve many purposes; for instance, metal ions can help in stabilizing nucleophilic species within the active site. Organic cofactors can be either coenzymes, which are released from the enzyme's active site during the reaction, or prosthetic groups, which are tightly bound to an enzyme. Organic prosthetic groups can be covalently bound including but not limited to biotin in enzymes such as pyruvate carboxylase). A non-limiting example of an enzyme that contains a cofactor is carbonic anhydrase, which is shown in the ribbon diagram above with a zinc cofactor bound as part of its active site. These tightly bound ions or molecules are usually found in the active site and are involved in catalysis. For example, flavin and heme cofactors are often involved in redox reactions.

In some embodiments, the screening of the gDNA library is a cell-free system, for example, where the gDNA library is processed as single droplets, where the droplets comprise protein synthesis regents for expression of the genes, e.g., the redox-enzymes, encoded by the gDNA in the droplet.

In some embodiments, the gDNA library is a metagenomic gDNA library, and is processed through a microfluidic device to produce individual droplets, where each droplet comprises or encapsulates one or more single gDNA sample, and where the droplet comprises cell-free cell synthesis reagents to express the microbial redox-enzyme protein encoded by the gDNA in the droplet.

In some embodiments, the assay or method to identify the MRE can be a high-throughput system. In some embodiments, the assay can be performed on a microfluidic platform. For example, by way of an illustrative example only, a high throughput microfluidic screening platform for the discovery of microbial redox-enzymes is described herein, the inventors have utilized microfluidic devices designed and fabricated in polycarbonate via a CNC micromill, using software developed by the inventors. The devices encapsulate single members of a metagenomic DNA library into individual droplets containing cell-free protein synthesis reagents to express putative enzymes from library DNA. Enzyme activity is then monitored using an Amplex™ UltraRed assay, and droplets containing enzymes which degrade the molecule of interest are sorted by fluorescence intensity. DNA within sorted droplets are then sequenced and Open Reading Frames (ORFs) are validated automatically using cell-free protein synthesis, and liquid handling robots (e.g. see, FIGS. 1A and 1B).

VI. Methods to Generate a Metagenomic Library Using Environmental or Genomic DNA As disclosed herein, the first part of the platform comprises contacting a genomic DNA (gDNA) library with an analyte. In one embodiment, genomic DNA libraries will be generated. In one embodiment, genomic DNA libraries will be screened for functional redox enzymes which degrade a molecule of interest, via microfluidic devices.

In one embodiment, the gDNA library comprises environmental gDNA and is an environmental gDNA library. In one embodiment, environmental DNA libraries will be generated. In one embodiment, environmental gDNA libraries will be screened for functional redox enzymes which degrade a molecule of interest, via microfluidic devices.

Environmental DNA (eDNA) is genomic DNA that is collected from a variety of environmental samples such as soil, seawater, snow or even air rather than directly sampled from an individual organism. As various organisms interact with the environment, DNA is expelled and accumulates in their surroundings. Example sources of eDNA include, but are not limited to, feces, mucus, gametes, shed skin, carcasses and hair.

Environmental DNA offers a rich resource for novel enzymes that can be utilized in a variety of applications, from biosensing to biomanufacturing. However, the high-throughput functional screens necessary for discovery have relied heavily on flow-cytometry or PDMS-based microfluidic devices, both of which require considerable resources, training, and infrastructure. Likewise, characterization of putative hits is often laborious and would benefit from automation.

Generation of gDNA or eDNA Libraries of Metagenomic Samples

Figure 1B:
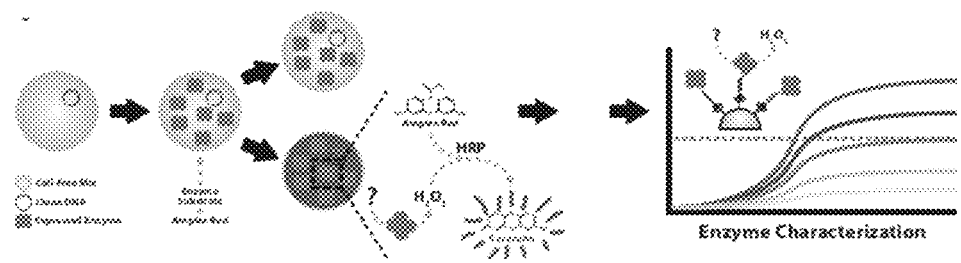
Figure 1C:
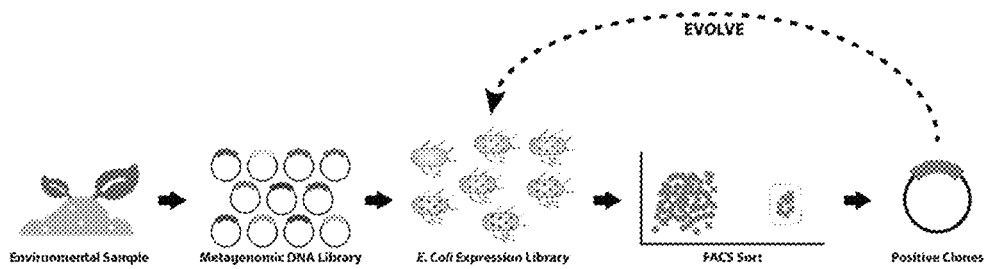

As disclosed herein, a gDNA or an eDNA library of metagenomic samples will be prepared in one of two ways (see, e.g. FIG. 1A). Isolation of gDNA is well within the abilities of one skilled in the art and can be achieved using kits including but not limited to e.g. the CopyControl Fosmid Library Production Kit or an in-house developed protocol. If using the in-house protocol, the main steps involve isolating the gDNA using e.g. the GenElute Bacterial Genomic DNA kit. The gDNA will be fragmented using e.g. a g-TUBE followed by end-repairing the fragments with the Quick Blunting Kit (e.g. NEB #E1201S).

As disclosed herein, a gDNA or an eDNA library can be subcloned into a vector backbone, comprising a T7 promoter, a T7 terminator and a ribosome binding site (RBS). For example, a fragmented gDNA can comprise a PmlI restriction enzyme site between a T7 promoter, a ribosome binding site (RBS), and a T7 terminator. This single blunt-end restriction enzyme site allows for the blunt-end ligation of vector to gDNA fragments. For example, in order to prepare the vector it is digested with the restriction enzyme PmlI and then dephosphorylated with e.g. the Quick Dephosphorylation Kit (NEB #M0508S) to prevent self-ligation. As disclosed herein, the vector and fragmented gDNA are then ligated and transformed by electroporation e.g. into *E. coli* TOP10 (e.g. Thermo Fisher Scientific #C404010) and incubated overnight on carbenicillin agar plates. A sufficient number of plates are necessary to generate a library of sufficient diversity. Once the colonies have grown sufficiently, plates will be scraped and pooled into fresh LB media with carbenicillin, which will serve as the initial gDNA library. Plasmid DNA containing gDNA fragments from this library culture are purified (e.g. using the Qiagen #27104 kit) so that the DNA library can be moved into a new strain of *E. Coli* for screening assays. Methods described herein, are well within the abilities of one skilled in the art and can be achieved using the kits listed.

VII. Target Analytes

In some embodiments, described herein is an assay and method for identification of redox-enzymes that are specific to a target analyte (also referred to as "analyte of interest"). An analyte of interest can be selected from any of: small molecule, hormone, toxin and the like, as discussed herein. That is, the microbial redox-enzyme specifically binds to, or has high affinity, to a target small molecule, hormone, toxin and the like.

Non-limiting examples of target analytes detected by a redox-enzyme as described herein can be selected from any of non-limiting examples of analytes, for example, but are not limited to, nicotine, Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Somatostatin, Amylin, Atrial-natriuretic peptide (ANP), Gastrin, Secretin, Cholecystokinin (CCK), Fibroblast Growth Factor 19 (FGF19), Incretins, Somatostatin, Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, Irisin. Non-limiting examples of steroid hormones that can be detected by the current invention include progesterone, aldosterone, testosterone, estradiol, estrone, melatonin, hydrocortisone and cortisol. In particular embodiments, the analyte is progesterone. In some embodiments, the progesterone is human progesterone.

In some embodiments, the MRE assay can be used to screen for MREs that are selective to an analyte selected from any of: caffeine, levetiracetam, gabapentin, procainamide, creatinine, phenytoin, carbamazepine, oxcarbazemine, primidone, lidocaine, cortisol, hydrocortisone, aldosterone, melatonin, estradiol, progesterone.

In some embodiments the analyte is a drug or drug metabolite, for example, opioid drug (including natural alkaloids, and synthetic and semi-synthetic opioids) or opioid metabolite (e.g., oxymorphone, noroxycodone, morphine, hydrocodone, norcodeine, oxymorphone, 6-hydroxy-oxymorphone, hydromorphine, norhydrocodone, dihydrocodeine, hydromorphol, codeine-6-glucuronide and norcodeine, morphine-6-glucuronide (M6G)), cocaine, cocaine metabolites, cannabis or cannabinoid-based drug or metabolite, marijuana, benzodiazepine, barbiturate, amphetamine, methtamphetamine, alcohol. In some embodiments, the analyte is selected from an of: cannabidiol (terahydro-cannabinol) and other marijuana metabolite: a metabolite of cocaine, opiates metabolites, phencyclidine (the PCP, angel dust), amphetamines, barbiturates, benzene, dinitrogen classes, methaqualone, and propoxyphene. Such biosensors that detect such analytes are useful for caregivers and enforcement officials (e.g., police officers, sports testing, prison officers etc.) as well as clinical practitioners for drug screening purposes and/or to assess if a subject has taken a drug or other regulated substance, and also to quantify the drug dose.

In some embodiments, the analyte is of mammalian origin, e.g., human origin and in some embodiments, the analyte is non-mammalian origin. Additional examples of small molecules and hormones that can be measured according to the current invention are well known to a person of ordinary skill in the art and such embodiments are within the purview of the current invention.

In all aspects herein, the sample can be a biological sample obtained from the subject. Exemplary samples include, but are not limited to serum, plasma, cell lysate, milk, saliva, vitreous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers or adults. In some embodiments, the sample may be from a subject who has been treated with a drug, or may be from an untreated or drug naive subject. In some embodiments, the biological sample may be from an animal, including economically useful animals such as goats, cows, sheep, chicken. In some embodiments, the biological samples may be from milk-producing animals. Moreover, the sample can be in various forms including but not limited to a liquid, frozen, chilled, lyophilized sample. The sample may be subjected to additional purification or treatment steps prior to and/or following the biosensor measurement described herein. In some embodiments, the sample is a non-biological fluid, such as a number of ecological environments such as river or lake water, ocean, drinking water supply or lab solution.

In some embodiments, the analyte is a cytokine biomarkers including but not limited to IL-1β, IL-6, IL-8, IL-12, IL-17, IL-18, TNF-α, IL-10, IL-11 and IL-13.

In another embodiment, the analyte is a toxic chemical such as neurotoxins, fentanyl, novichok or anthrax.

In another embodiment, the analyte is a hydrocarbons or a chemical stressors released by plants including but not limited to coral reefs.

In another embodiment, the analyte is a fertilizer. Non-limiting examples of fertilizer detected by a redox-enzyme as described herein include but are not limited to nitrogen fertilizers, phosphate fertilizers, potassium fertilizers, compound fertilizers and organic fertilizers.

In another embodiment, the analyte is a pesticide. Non-limiting examples of a pesticide detected by a redox-enzyme as described herein include but are not limited to herbicides, insecticides, nematicide, molluscicides, piscicides, avicides, rodenticides, bactericides, insect repellents, animal repellents, antimicrobials, fungicides and disinfectants.

In another embodiment, the analyte is a carcinogen. Non-limiting examples of a carcinogen detected by a redox-enzyme as described herein include but are not limited to any substance, radionuclide, or radiation that promotes carcinogenesis, the formation of cancer including but not limited to radioactive substances, inhaled asbestos, certain dioxins, and tobacco smoke.

Although only four sectors have been listed here there are many more as the biological world around us operates on chemical signals and at the moment there are inadequate ways to measure them in real-time at a low cost.

In some embodiments the analyte is a drug or drug metabolite, for example, opioid drug (including natural alkaloids, and synthetic and semi-synthetic opioids) or opioid metabolite (e.g., oxymorphone, noroxycodone, morphine, hydrocodone, norcodeine, oxymorphone, 6-hydroxy-oxymorphone, hydromorphine, norhydrocodone, dihydrocodeine, hydromorphol, codeine-6-glucuronide and norcodeine, morphine-6-glucuronide (M6G)), cocaine, cocaine metabolites, cannabis or cannoboid-based drug or metabolite, marijuana, benzodiazepine, barbiturate, amphetamine, methtamphetamine, alcohol. In some embodiments, the analyte is selected from an of: cannabidiol (terahydrocannabinol) and other marijuana metabolite: a metabolite of cocaine, opiates metabolites, phencyclidine (the PCP, angel dust), amphetamines, barbiturates, benzene, dinitrogen classes, methaqualone, and propoxyphene. Such redox-enzymes that detect such analytes are useful for caregivers and enforcement officials (e.g., police officers, sports testing, prison officers etc.) as well as clinical practitioners for drug screening purposes and/or to assess if a subject has taken a drug or other regulated substance, and also to quantify the drug dose.

In some embodiments, the analyte is of mammalian origin, e.g., human origin and in some embodiments, the analyte is non-mammalian origin. Additional examples of small molecules and hormones that can be measured according to the current invention are well known to a person of ordinary skill in the art and such embodiments are within the purview of the current invention.

In all aspects herein, the sample can be a biological sample obtained from the subject. Exemplary samples include, but are not limited to serum, plasma, cell lysate, milk, saliva, vitreous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers or adults. In some embodiments, the sample may be from a subject who has been treated with a drug, or may be from an untreated or drug naive subject. In some embodiments, the biological sample may be from an animal, including economically useful animals such as goats, cows, sheep, chicken. In some embodiments, the biological samples may be from milk-producing animals. Moreover, the sample can be in various forms including but not limited to a liquid, frozen, chilled, lyophilized sample. The sample may be subjected to additional purification or treatment steps prior to and/or following the redox-enzyme measurement as described herein. In some embodiments, the sample is a non-biological fluid, such as a number of ecological environments such as river or lake water, ocean, drinking water supply or lab solution.

VIII. Detection Means of Signals from Redox Mediators

The MRE assay detection system generates an electrochemically or non-electrochemically detectable product or by-product directly, or alternatively, the MRE assay system can also include at least one further component, such as a readout enzyme and readout product as disclosed herein. In some embodiments, the further component may be: one or more additional enzyme(s) forming an enzymatic pathway utilizing the product or by-product of the initial redox-enzyme reaction to thereby generate a photometrically or electrochemically detectable product or by-product; or at least one signal mediator; or both the additional enzyme(s) and the signal mediator(s). The signal mediator(s) may be selected from, for example: indicators, such as a pH-change indicators; electron transfer mediators; photometric mediators, chemiluminescence, and other components.

In some embodiments in an electrochemical embodiment of the assay, the redox-enzyme system utilizes an electrochemically detectable cofactor, such as NADH, or generates a by-product, such as $H_2O_2$, during the course of the enzymatic reaction with the target analyte. However, detection of the target analyte is not limited to electrochemical means, and the redox-enzyme system disclosed herein may employ different detection methods, e.g., UV, fluorescence, or other suitable methods of detecting the target analyte and redox-enzyme interactions.

(i) Non-Electrochemical Detection Means

Non-electrochemical detection of redox-mediators (Med), or readout enzymes involves, for example, any colorimetric or photometric detection mode known in the art (for example, any colorimetric, spectrometric, spectrophotometric, luminescence-based, chemiluminescence-based, or fluorescence-based detection method.) In some embodiments, the detection of $H_2O_2$ probes can be by chemiluminescence, fluorescence, potentiometric or amperometric methods.

A fluorescence detection device has the following minimum requirements: it must be light-tight to eliminate stray light from its surroundings, its fluorophore must be stored in the dark to prevent photobleaching (that is increase shelf life), and its optics must be at a 90° angle. A diode emitting the desired excitation wavelength can function as the light source, and a PMT can function as the detector. These need not be elaborate since both the excitation and emission λmax of the fluorophore are known, and these are the only wavelengths required. The same breath collection and acetone partitioning apparatus used in an enzyme electrochemical device can be used in a fluorescence device. A portable fluorescence detector for aflatoxin has been described in the literature (M A Carlson et al., An automated handheld biosensor for aflatoxin, Biosens. Bioelectr. 14:841 (2000)), so a precedent for a portable fluorescence detector exists.

Both direct and indirect fluorescence allows the detection of the target analyte and redox-enzyme interactions, via the redox-mediator. The $H_2O_2$-generating systems can use $H_2O_2$ and an additional fluorophore. In these systems, $H_2O_2$ production causes an increase in fluorescence intensity that is proportional to the target analyte concentration.

Indirect fluorescence of NADH can be detected using the dye rhodamine 123. In some embodiments, non-radiative energy transfer (also called fluorescence resonance energy transfer, FRET) occurs between the excited states of NADH and rhodamine 123. FRET is a well-known technique for determining the proximity of two species, i.e. FRET is utilized as a "molecular yardstick" both in vitro and in vivo. In this context of the target analyte and redox-enzyme interactions, a donor fluorophore, e.g., NADH, transfers its excited state energies to the acceptor fluorophore, rhodamine 123. (R P Haugland, Handbook of Fluorescent Probes and Research Products, 2002 (9th ed.; Molecular Probes, Inc.; Eugene, Oreg.); K Van Dyke et al., eds. Luminescence Biotechnology. Instruments and Applications, 2002 (CRC Press; Boca Raton, Fla.) and references contained therein). The NADH-rhodamine 123 FRET method has been successfully employed in other enzymatic assays (M H Gschwend et al., Optical detection of mitochondria) NADH content in intact human myotubes, Cell. Mol. Biol. 47:OL95 (2001); H. Schneckenberger et al., Time-gated microscopic imaging and spectroscopy in medical diagnosis and photobiology, Opt. Eng. 33:2600 (1994)). Bioluminescence resonance energy transfer, or BRET, may also be used in conjunction with an acetone-specific enzyme system according to the present invention. In BRET, the donor fluorophore is replaced by a luciferase. Bioluminescence from luciferase in the presence of a substrate excites the acceptor fluorophore. BRET has also been applied in vitro and in vivo (K Van Dyke et al., 2002).

ATP can be derivatized with a fluorophore for indirect fluorescence. Several commercially available dyes include BODIPY ATP and trinitrophenyl ATP (Haugland, 2002). These analogs change their fluorescence intensity or become fluorescent when bound to an enzyme's ATP binding site.

Indirect fluorescence detection of $H_2O_2$ has also been reported (Carr & Bowers, 1980). These methods utilize dyes that reduce the peroxide to $H_2O_2$ and are themselves oxidized. Homovanillic acid (4-hydroxy-3-phenylacetic acid) and p-hydroxyphenylacetic acid are among the most commonly used in clinical chemistry (Can and Bowers, 1980). A commercially available kit uses the dye Amplex™ UltraRed for fluorescence detection of $H_2O_2$ (Haugland, 2002).

Any fluorescent dyes and fluorescence-detectable enzyme substrate or cofactor analogs can be used in a fluorescence device to detect the target analyte and redox-enzyme interactions.

Chemiluminescence (CL) and electrogenerated chemiluminescence (ECL) (collectively referred to herein as "(E)CL") are widely used in medical diagnostics and analytical chemistry (C Dodeigne et al., Chemiluminescence as a diagnostic tool: A review, Talanta 2000, 51:415; K A Fahnrich et al., Recent applications of electrogenerated chemiluminescence in chemical analysis, Talanta 2001, 54:531). Enzyme-based (E)CL systems are sensitive and specific, and many CL systems are used with enzyme cycling to detect $H_2O_2$ (Dodeigne et al., 2000). (E)CL can detect picomolar (pM; 10-12M) concentrations of analyte over a wide linear range (Dodeigne et al., 2000; Fähnrich et al., 2001). An (E)CL device can be constructed in accordance with the following principles. Since the reaction itself emits light, an (E)CL device does not need a light source. A photomultiplier tube (PMT) can function as the detector; (E)CL is visible to the unaided, dark-adapted eye. A battery can be the power source for ECL. ECL requires electrodes and a source of applied potential. Like a fluorescence detection device, (E)CL devices need to be light tight and their reagents need to be protected from light until use. Also like fluorescence, (E)CL requires derivatized reagents or additional enzymes and reagents to detect acetone. (E)CL devices can be used with disposable strips (B D Leca et al., Screen-printed electrodes as disposable or reusable optical devices for Luminol electrochemiluminescence, Sens. Actuat. B. 2001, 74: 190) and can be miniaturized (Y Lv et al., Chemiluminescence biosensor chip based on a microreactor using carrier airflow for determination of uric acid in human serum, Analyst 2002, 127:1176).

An optical electrode (or optrode) can be fabricated using for detection of the target analyte and redox-enzyme interactions according to the present invention. For example, an optrode such as that used in a glucose optrode that uses ECL, may be employed (see C H Wang et al., Co-immobilization of polymeric Luminol, iron(II) tris(5-aminophenanthroline) and glucose oxidase at an electrode surface, and its application as a glucose optrode, Analyst 2002, 127:1507)).

The most common CL systems involve the detection of $H_2O_2$ or another reactive oxygen species (Carr & Bowers, 1980; Haugland, 2002; Dodeigne et al., 2000; K Van Dyke et al., 2002) and references contained therein). The classic system is Luminol-peroxidase. In basic solution, $H_2O_2$ oxidizes Luminol to an excited amino-phthalate ion; the excited amino-phthalate ion emits a 425-nm photon to return to its ground state. When used in medical diagnostics, this reaction is catalyzed with horseradish peroxidase (HRP) (Can & Bowers, 1980; Dodeigne et al., 2000). Thus any enzyme system that produces $H_2O_2$ or requires a cofactor that can react with additional reagents to form $H_2O_2$ can be used in a CL device. The $H_2O_2$-generating systems described herein can use Luminol-HRP directly for acetone detection. These enzyme cycling schemes increase the light emission over time because the substrates are continuously recycled (Dodeigne et al., 2000). While Luminol itself is frequently used in CL, its improved analogs can also be used in a CL-based detector according to the present invention, in place of Luminol, in order to increase the sensitivity. Examples of such analogs are those described in Carr & Bowers, 1980; and Dodeigne et al., 2000.

NADH detection using CL is a common technique (Dodeigne et al., 2000). For example, in the presence of 1-methoxy-5-methylphenazinium me thylsulfate, NADH reduces $O_2$ to $H_2O_2$ which generates light using the Luminol-peroxidase system (Dodeigne et al., 2000). For an acetone monitor, the $O_2$ in ambient air is sufficient to detect acetone using this system. NADH also reacts with oxidized methylene blue to form $H_2O_2$ that reacts with Luminol (Can and Bowers, 1980). NADH can also act as a CL quencher. The fluorescence intensity of the substrate ALPDO is decreased in the presence of NADH and HRP (Van Dyke et al., 2002). NADH also can be used with Ru(bpy)3 2+ for ECL (E S Jin et al., An electrogenerated chemiluminescence imaging fiber electrode chemical. sensor for NADH, Electroanal. 2001, 13(15):1287). Rhodamine B isothiocyanate can also be used for ECL detection of $H_2O_2$(Fähnrich et al., 2001). ECL also offers another advantage in that, by use of a properly poised electrode, the electroactive species can be regenerated at the electrode surface. Regeneration both conserves reagents and allows durable and/or "reagentless" sensors. All these systems can be used in a (E)CL device interfaced to an acetone-specific enzyme system according to the present invention.

CL is widely used to quantitate ATP simply and sensitively (Can & Bowers, 1980). The enzyme luciferase catalyzes the reaction of ATP and luciferin to produce excited-state oxyluciferin, which returns to its ground state with the emission of a 562-nm photon (Carr & Bowers, 1980; Haugland, 2002). The quantum yield for this reaction is very high; 10-14 mol ATP can be detected. A kit for this reaction is commercially available (Haugland, 2002). Because luciferase is the enzyme that causes fireflies to "glow," this reaction is referred to as bioluminescence. Both native and recombinant luciferase are commercially available, and several groups have reported using bioluminescence ATP assays to quantify biological analytes (P Willemsen et al., Use of specific bioluminescence cell lines for the detection of steroid hormone [ant]agonists in meat producing animals, Anal. Chim. Acta 2002, 473:119; S J Dexter et al., Development of a bioluminescent ATP assay to quantify mammalian and bacterial cell number from a mixed population, Biomat. 2003, 24:nb27). In addition to the Luminol-HRP system, $H_2O_2$ can also be detected using peroxyoxalic acid derivatives (Dodeigne et al., 2000). $H_2O_2$ can also be detected with CL non-enzymatically with ferricyanide as the catalyst (Dodeigne et al., 2000). In these (E)CL systems, detection of the target analyte and redox-enzyme interactions as described herein either produce $H_2O_2$ or require cofactors that can be utilized to form $H_2O_2$.

Optical biosensors use photometric detection (that is, absorbance, fluorescence) of substrates consumed or products formed by the reaction catalyzed by the enzyme system incorporated into the sensor. The target analyte and MRE reactions as described may be monitored by several photometric methods-namely by measuring NAD(P)H absorbance at 340 nm for the pyridine nucleotide-dependent enzymes or absorbance of the quinoneimine dye for the $H_2O_2$ forming enzyme systems. For the later, addition of a peroxidase allows detection of $H_2O_2$ by catalyzing the reduction of $H_2O_2$ with concomitant oxidation of a dye compound that upon oxidation absorbs at a specified wavelength. Peroxidase enzymes (for example, commercially available horseradish peroxidase) typically have broad substrate specificities so several different electron donor compounds may be used. NAD(P)H consumption may also be measured by fluorescence detection (excitation at 350 nm and emission at 450 nm).

calorimetry may be employed as a detection means to detect the target analyte and redox-enzyme interactions according to the present invention. Chemic reactions are typically either exo- or endothermic; that is, they release or absorb heat as they occur calorimeters detect and measure this heat by measuring a change in the temperature of the reaction medium (K Ramanathan & B Danielsson, Principles and applications of thermal biosensors, Biosens Bioelectr. 16:417 (2001); B Danielsson, Enzyme Thermistor Devices. In Biosensor Principles and Applications. Vol. 15, pp. 83-105 (L J Blum & P R Coulet, eds.; Bioprocess Technology Series, volume 15; Marcel Dekker, Inc: New York, 1991, pp. 83-105, and references contained therein).

Thus, the action of the target analyte and redox-enzyme interactions may be monitored calorimetrically. Calorimeters have been designed that are sensitive enough to detect protein conformational changes, and calorimetry has been used to study many enzymatic reactions in detail (M. J. Todd & J Gomez, Enzyme kinetics determined using calorimetry: a general assay for enzyme activity? Anal. Biochem. 2001, 296:179 (2001)).

The major advantage of calorimetry is the lack of derivatization required for analysis (Danielsson, 1991). Since most reactions involve heat exchange, and this heat is detected, no chromophores, fluorophores, luminophores, "mediators," or other modifications of the analyte are required. Reagents and analytes can be used "as is." This allows the analysis of both reactions that lack a chromophore or fluorophore and/or would be difficult or impossible to derivatize or couple to the generation of an electroactive species.

Miniaturized or chip-based thermosensors have been reported in the literature (Ramanathan & Danielsson, 200:1; B Xie & B Danielsson, Development of a thermal microbiosensor fabricated on a silicon chip. Sens. Actuat. B 6:127 (1992); P Bataillard et al., An integrated silicon thermopile as biosensor for the thermal monitoring of glucose, urea, and penicillin. Biosen. Bioelect. 8:89 (1993)). These devices range from radically arranged thermopiles on freestanding membranes to groups of thermopiles constructed on silicon/glass microchannels. These devices have been used to detect specific, single enzymatic reactions (Danielsson, 1991; Xie & Danielsson, 1992; Bataillard et al., 1993). Moreover, two groups have reported thermosensors for glucose (B Xie et al., Fast determination of whole blood glucose with a calorimetric micro-biosensor, Sens. Actuat. B 15-16:141 (1993); M J Muehlbauer et al., Model for a thermoelectric enzyme glucose sensor, Anal. Chem. 61:77 (1989); B C Towe & E J Guilbeau, Designing Medical Devices, 1998. Preliminary experiments using a conventional calorimeter indicate that the secondary alcohol dehydrogenase-acetone reaction is exothermic (data not shown).

A. Fluorescent Dyes and Molecules

In one aspect, described herein is a method for determining the presence or absence of a MRE comprising contacting an analyte of interest with a nucleic acid probe wherein the probe contains a marker; and wherein in the presence of a MRE capable of detecting an analyte of interest, the analyte will be degraded and will generate a product that binds to the marker resulting in the emission of a fluorescent signal and wherein in the absence of a MRE capable of detecting an analyte of interest, the analyte will not generate a signal and selecting an analyte that generates a signal.

In one embodiment, droplets above a preset fluorescence threshold will be sorted and sequenced. Droplets that show an increase or decrease in fluorescence emission of at least 1, of at least 2, of at least 3, of at least, 5, of at least 10, of at least 20, of at least 50, of at least 100, of at least 200, of at least 500, of at least 1000 compared to a control sample containing PBS and the fluorescent molecule will be sorted and sequenced.

Putative Open Reading Frames will be cloned into expression vectors followed by enzyme purification and characterization. The choice of a proper enzyme purification and characterization system for a particular application is well within the abilities of one skilled in the art.

In one embodiment, the two redox enzymes, APEX2 and NicA2, are expressed in a cell-free system and tested for functionality using Amplex™ UltraRed. As enclosed herein, a microfluidic device with droplets containing cell-free mix & X-Gal. Droplets contain either no DNA, or plasmid DNA driving LacZ (β-galactosidase) expression. Only droplets expressing LacZ produce a blue color change, demonstrating functional protein can be expressed within droplets.

As disclosed herein, the second part of the platform used to identify novel MRE oxidases relies on the fluorescent molecule 10-Acetyl-3,7-dihydroxyphenoxazine. 10-Acetyl-3,7-dihydroxyphenoxazine as a reporter fluorescent molecule. In one embodiment, the fluorescence molecule is 10-Acetyl-3,7-dihydroxyphenoxazine. In one aspect of any of the embodiments, the one or more fluorescence probes to detect $H_2O_2$ is 10-Acetyl-3,7-dihydroxyphenoxazine (N-Acetyl-3,7-dihydroxyphenoxazine or ADHP) (Amplex™ UltraRed or AUR). 10-Acetyl-3,7-dihydroxyphenoxazine is highly specific and stable. The substrate itself is nearly colorless and nonfluorescent until it is oxidized by $H_2O_2$ (reacting in a 1:1 stoichiometry) in the presence of horseradish peroxidase (HRP) to become the highly red fluorescent resorufin.

The structure of 10-Acetyl-3,7-dihydroxyphenoxazine (N-Acetyl-3,7-dihydroxyphenoxazine

Figure 41A:
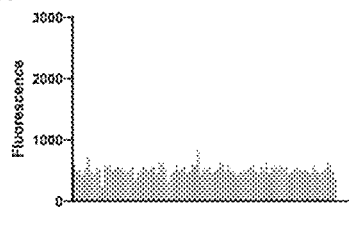
FIG. 41A-41F shows an analysis of a candidate MRE identified using the optimized MRE assay to identify a MRE responsive to hydrocortisone in Rosetta2 (DE3) cells comprising a synthetic mixture of seven gDNA libraries constructed from microbes known to be responsive to sterols.
Figure 41B:
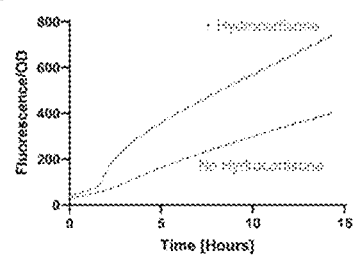
Figure 41C:
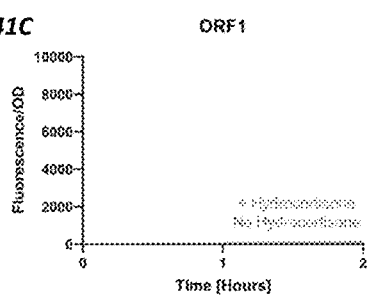
Figure 41D:
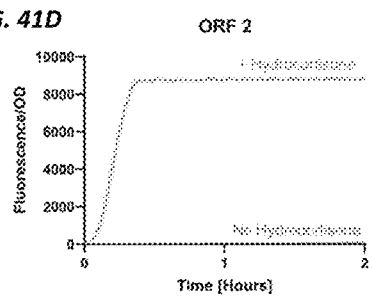
Figure 41E:
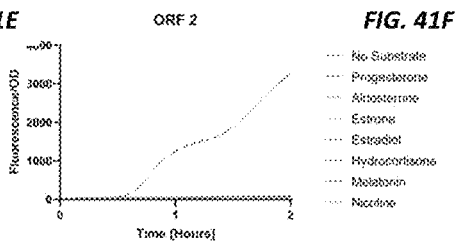
Figure 41F:
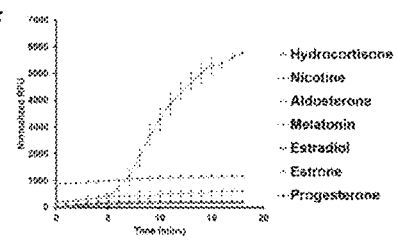
Figures 42, 43:
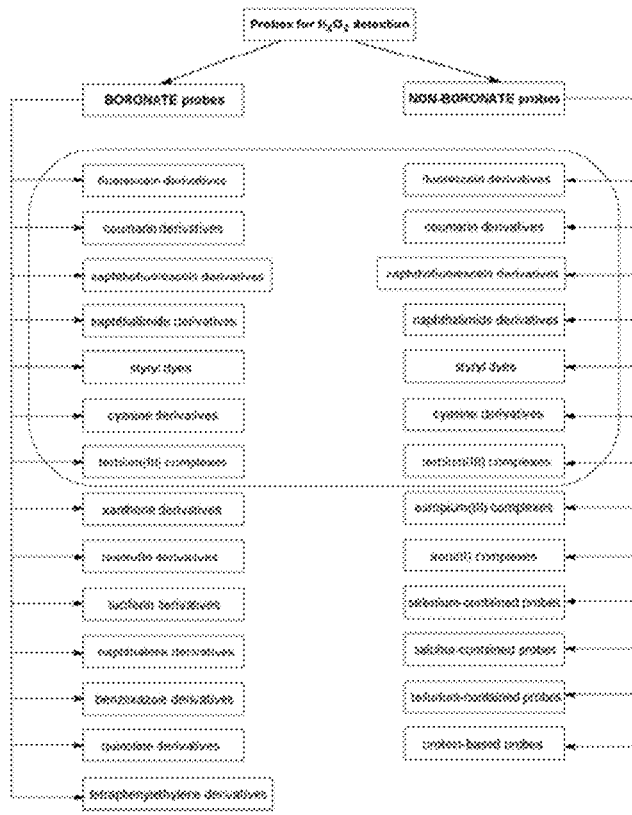
FIG. 42 shows a schematic of exemplary classes of probes to detect hydrogen peroxide under biological conditions, including classes of boronate and non-boronate based $H_2O_2$ probes.
FIG. 43 shows a table of exemplary boronate-based $H_2O_2$ probes that can be used to detect $H_2O_2$ produced from a candidate oxidase MRE in a MRE assay as disclosed herein.
Figure 44A:
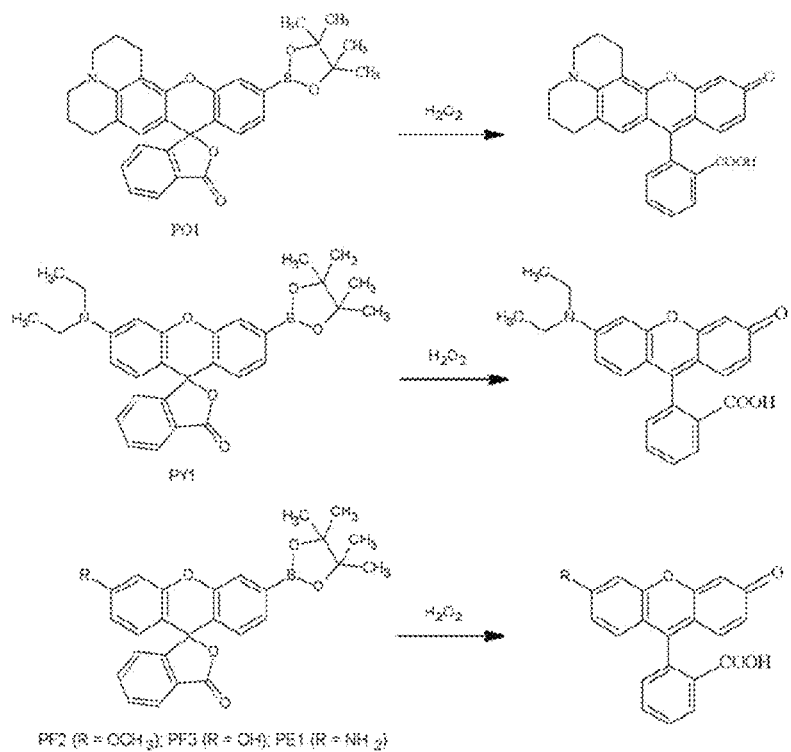
FIG. 44A-44P shows exemplary boronate-based probes that can be used instead of the readout enzyme, readout substrate system used herein.
Figure 44B:
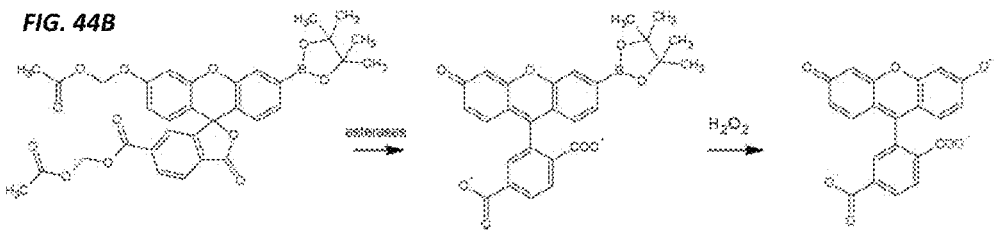
FIG. 44B shows the conversion of peroxyflur-6-acetoxymethyl ester into a fluorescent product in the presence of $H_2O_2$.
Figure 44C:
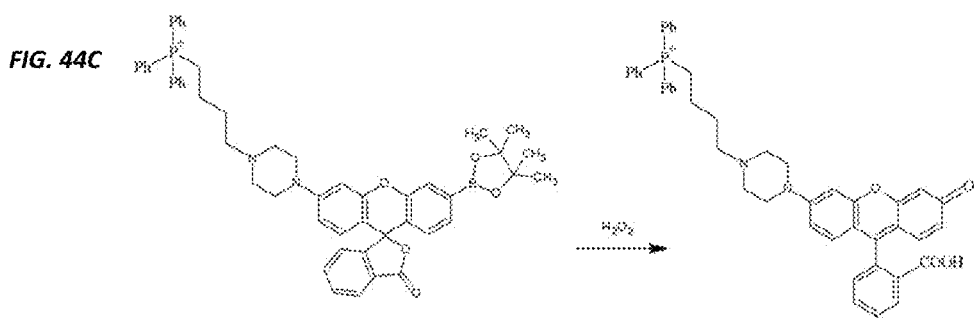
FIG. 44C shows the conversion of MitoPY1 into a fluorescent product in the presence of $H_2O_2$.
Figure 44D:
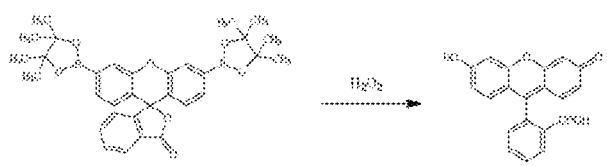
FIG. 44D shows the conversion of Peroxyfluror-1 (PF1) into a fluorescent product in the presence of $H_2O_2$.
Figure 44E:
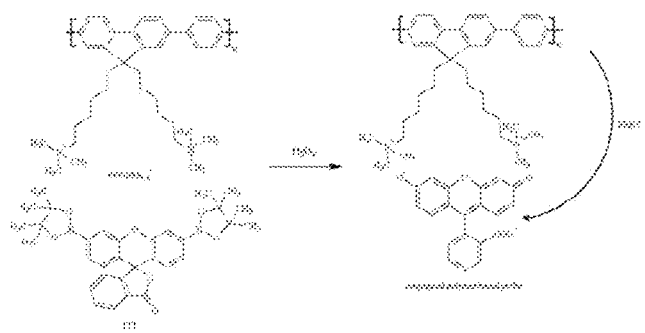
FIG. 44E shows the conversion of PFP-NMe$_3^+$ into fluorescein in the presence of $H_2O_2$.
Figure 44F:
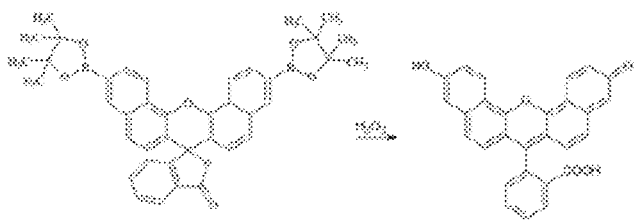
FIG. 44F shows the $H_2O_2$-mediated release of naphthofluorescein PFP-NMe$_3^+$ into fluorescein in the presence of $H_2O_2$.
Figure 44G:
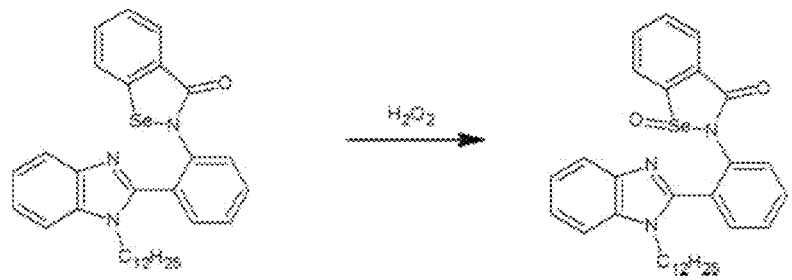
FIG. 44G shows the $H_2O_2$-mediated oxidation of D-HMSe to form D-HMseO.
Figure 44H:
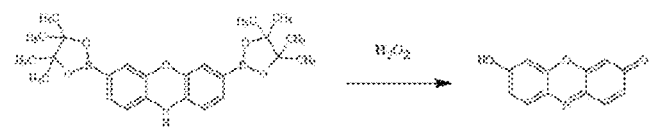
FIG. 44H shows the $H_2O_2$-mediated conversion of peroxyresorufin-1 into a fluorescent product in the presence of hydrogen peroxide.
Figure 44I:
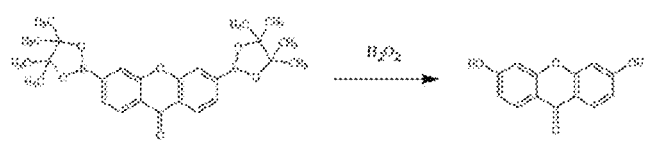
FIG. 44I shows the $H_2O_2$-mediated conversion of peroxyxanthone-1 into a fluorescent product in the presence of hydrogen peroxide.
Figure 44J:
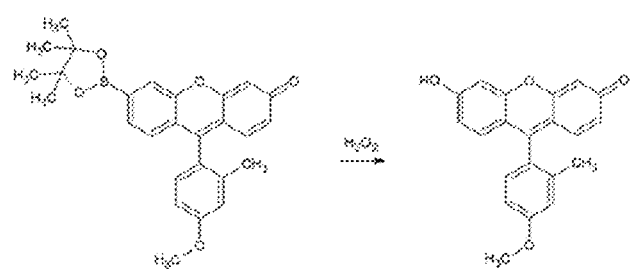
FIG. 44J shows the $H_2O_2$-mediated conversion of non-fluorescent peroxy green 1 into a fluorescent product in the presence of hydrogen peroxide.
Figure 44K:
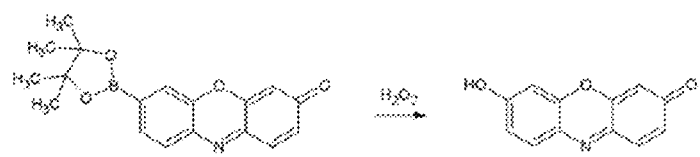
FIG. 44K shows the $H_2O_2$-mediated conversion of non-fluorescent peroxy crimson 1 into a fluorescent product in the presence of hydrogen peroxide.
Figure 44L:
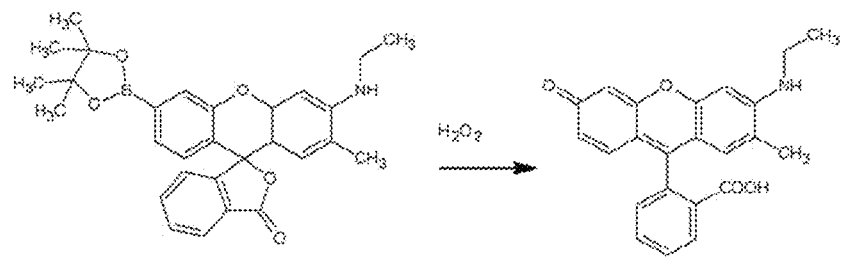
FIG. 44L shows the $H_2O_2$-mediated conversion of NucPE1 into a fluorescent product in the presence of hydrogen peroxide.
Figure 44M:
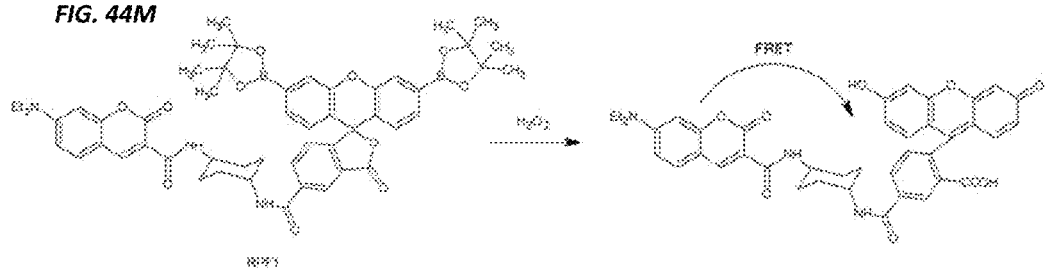
FIG. 44M shows the $H_2O_2$-mediated conversion of RPF1 into a fluorescent product in the presence of hydrogen peroxide.
Figure 44N:
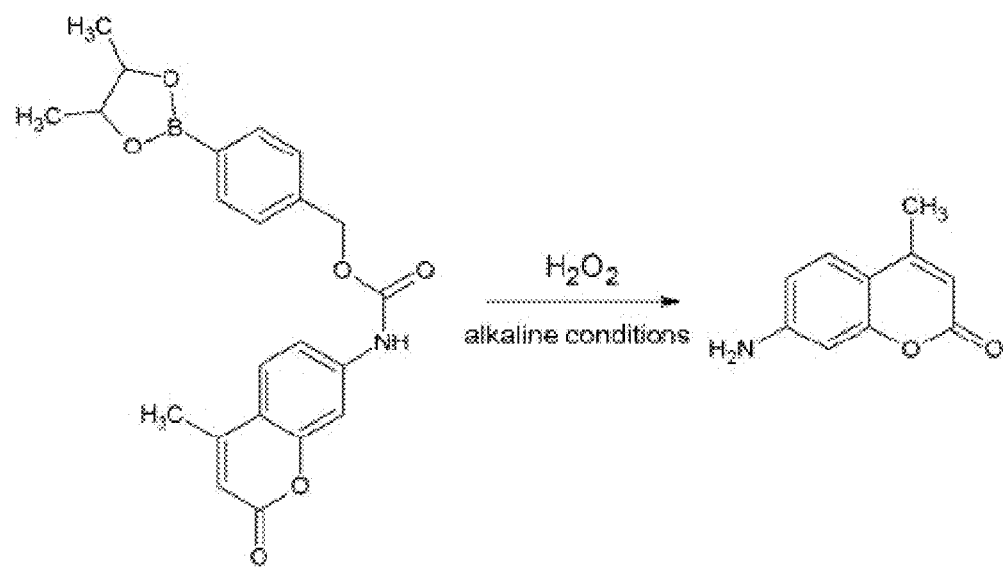
FIG. 44N shows the $H_2O_2$-mediated conversion of 7-amino-4-methylcoumarin into a fluorescent product in the presence of hydrogen peroxide.
Figure 44O:
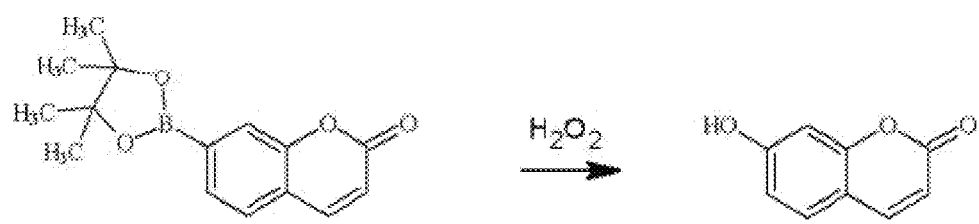
FIG. 44O shows the $H_2O_2$-mediated release of umbelliferone.
Figure 44P:
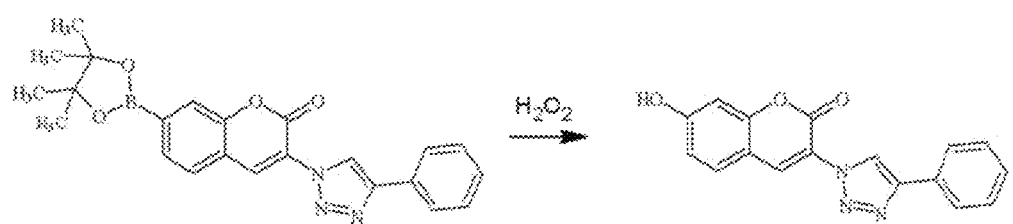

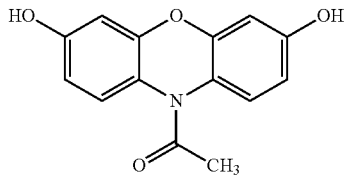 [SMILES: CC(=O)N1c2ccc(O)cc2Oc2cc(O)ccc21]

or Amplex™ UltraRed) is as follows:

In some embodiments, boronate-based and non-boronate based hydrogen-peroxide probes can be used, for example, as disclosed in FIGS. 41A-41N. Exemplary $H_2O_2$ probes which are boronate-based probes that can be used are selected from any of: 1a and 1b, PG1, PF1, RPF1, PC1, PY1-ME, PCL-1, Fl-B, which are disclosed in Zamajc et al., Crit Rev. Analytical Chemistry, 2016; 46 (3); 171-200, which is incorporated herein in its entity by reference. Such boronate-based probes do not need a catalyzing enzyme such as HRP or APEX2, rather they simply fluoresce in the presence of $H_2O_2$. Therefore, in a cell-based MRE screen, incubating cells expressing the MRE in the presence of an analyte and a boronate-based probe, if the cell comprises a MRE responsive to the target analyte, it will fluoresce and can be selected. Similarly, in a cell-free MRE system, droplets contacted with the target analyte and a boronate-based probe, droplets that fluoresce indicate that the droplet comprises a gDNA fragment comprising a candidate oxidase MRE.

IX. Electroconductive Devices comprising MREs for the measurement of analytes

The MRE as disclosed herein can be modified by persons of ordinary skill in the art for analyte sensing using electroconductive devices.

For illustrative purposes only, the oxidase MRE enzyme can be conjugated to an electroactive molecule and the analyte probe is attached or on the surface of a conducting surface of a semiconductor device, such that when the oxidase enzyme is bound to the analyte probe, the electroconductive molecule conjugated to the oxidase enzyme and the analyte are in close proximity to allow electron transfer, and the flow of electrons to the semiconductor device which is detected by an increase in current on the surface.

In another embodiment, electrochemical impedance spectroscopy can be used to measure the resistance of the system by using redox markers.

Other methods to modify the oxidase enzyme and analyte probes for electrochemical detection of the analyte and generating electroconductive biosensors for use herein are described in Electrochemical methods—Fundamentals and applications, 2Ed., Allen Bard and Larry Faulkner, and Electrochemistry for biomedical researchers, Richie L C Chen, World Scientific Press, each of which are incorporated herein in their entirety by reference.

The technology described herein relates to identification of a MRE useful in a biosensor for the accurate, reliable and sensitive measurement of an analyte of interest (i.e., target analyte) in the environmental, industrial, or clinical setting.

Another aspect of the technology described herein is a method for the ultra-high throughput microfluidic screening platform for the discovery of novel MREs, the inventors have utilized microfluidic devices designed and fabricated in polycarbonate via a CNC micromill, using software developed by the inventors. The devices encapsulate single members of a metagenomic DNA library into individual droplets containing cell-free protein synthesis reagents to express putative enzymes from library DNA. MRE enzymatic activity is then monitored using an Amplex™ UltraRed assay, and droplets containing enzymes which degrade the molecule of interest are sorted by fluorescence intensity. DNA within sorted droplets are then sequenced and Open Reading Frames (ORFs) are validated automatically using cell-free protein synthesis, and liquid handling robots (e.g. see, FIGS. 1A and 1B).

X. Definitions:

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E.

Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As used herein, the term "biological sample" refers to a sample obtained from a subject. The sample may be from a subject who has been treated with a drug, or may be from an untreated or drug naïve subject. Exemplary samples include, but are not limited to serum, plasma, cell lysate, milk, saliva, vitrous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers, adults or animals. Moreover, the sample can be in various forms including but not limited to a liquid, frozen, chilled, lyophilized sample. The sample may be subjected to additional purification or treatment steps prior to and/or following the affinity purification step herein.

As used herein, the term "analyte" refers to a substance which is catalyzed by the candidate redox-enzyme. In some embodiments, an analyte can be a "biological marker" or "biomarker", which is an analyte in a biological system and may be used as an indicator of the risk or progression of disease.

The term "redox" or "oxidation-reduction" or "oxidoreduction" reaction describes any reaction in which electrons are transferred from one molecule, compound, molecular group, etc. to another. The process of oxidation occurs in conjunction with (is coupled with) a reduction reaction, thus resulting in the transfer of electrons.

As used herein, a "redox enzyme" or "oxidoreductase" are used interchangeably herein and refer to an enzyme that catalyzes a reaction with one or more enzyme substrate(s), resulting in generation or utilization of electrons. The oxidoreductases (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection reduced coenzyme nicotinamide adenine dinucleotide (NADH) or hydrogen peroxide has been used galvanometer biosensor. In some instances, redox enzymes employ no prosthetic group, such as those that use reversible formation of a disulfide bond between two cysteine residues, as in the case of thioredoxin. Other redox enzymes use prosthetic groups, such as flavins, NAD, transition metal ions or clusters of such metal ions, etc. The use of the transition metal ions in these enzymes is due to their ability to attain multiple oxidation and spin states.

As used herein, the term "oxidase" refers to an enzyme that catalyzes an oxidation-reduction reaction, especially one involving dioxygen ($O_2$) as the electron acceptor. In reactions involving donation of a hydrogen atom, oxygen is reduced to water ($H_2O$) or hydrogen peroxide ($H_2O_2$).

As used herein, the term "biosensor device" refers to an analytical device which integrates a biorecognition element with a physical transducer to generate a measurable signal proportional to the concentration of an analyte recognized by the biorecognition element.

As used herein, the terms "redox molecule", "redox mediator" and "electroactive molecule" are used interchangeably herein and relate to any molecule that is able to undergo an electrochemical reaction. Upon which one or more electrons are either added to or removed from the molecule, converting it into a different oxidative state. For example, 1,4-Benzoquinone is an electroactive molecule that can be converted to hydroquione upon the reduction of the molecule with an addition of two electrons and two protons according to a specific embodiment.

As used herein, the term "environmental DNA" or "eDNA" refers to the genetic material collected from a variety of environmental samples such as soil, seawater, snow or even air rather than directly sampled from an individual organism.

As used herein, the term "genomic DNA" or "gDNA" refers to the complete set of an organism's genetic material.

As used herein, the term "metagenomics" refers to the direct genetic analysis of genomes contained with an environmental sample.

As used herein, the term "genomic library" refers to a collection of the total genomic DNA from a single organism. The DNA can be stored in a population of identical vectors, each containing a different insert of DNA. In order to construct a genomic library, the organism's DNA is extracted from cells and then digested with a restriction enzyme to cut the DNA into fragments of a specific size. The fragments can then be inserted into a vector using DNA ligase.

As used herein, the term "open reading frame" refers to a reading frame that has the ability to be translated. An ORF is a continuous stretch of codons that begins with a start codon (usually AUG) and ends at a stop codon (usually UAA, UAG or UGA). An ATG codon (AUG in terms of RNA) within the ORF (not necessarily the first) may indicate where translation starts. The transcription termination site is located after the ORF, beyond the translation stop codon. If transcription were to cease before the stop codon, an incomplete protein would be made during translation. In eukaryotic genes with multiple exons, introns are removed and exons are then joined together after transcription to yield the final mRNA for protein translation. In the context of gene finding, the start-stop definition of an ORF therefore only applies to spliced mRNAs, not genomic DNA, since introns may contain stop codons and/or cause shifts between reading frames. An alternative definition says that an ORF is a sequence that has a length divisible by three and is bounded by stop codons.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

As used herein, the term "allosteric" refers to a thermodynamic phenomenon in which the binding of a small molecule (or a posttranslational modification event) alters the affinity with which a protein binds to a second molecule. In the classical two-state Monod-Wyman-Changeux model the structural basis for this functional behavior is attributed to the ability of the allosteric protein to adopt two alternative conformations. The allosteric effector, by virtue of its preference for one versus the other structure, drives the system toward one or the other conformation. Allosteric effector binding, either the small molecule or the DNA, simply limits the conformations that are energetically available to the protein.

As used herein, the term "affinity" refers to the strength of the binding interaction between a single biomolecule (e.g. a redox-enzyme) to it substrate or analyte.

As used herein, a "nucleoside" is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As used herein, the term "analyte" refers to any compound, or chemical species is a substance or chemical constituent that is of interest in an analytical procedure. Non-limiting examples of analytes detected by the bioswitch as described herein can be selected from any of non-limiting examples of analytes that can be detected by the current invention include Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Somatostatin, Amylin, Atrial-natriuretic peptide (ANP), Gastrin, Secretin, Cholecystokinin (CCK), Fibroblast Growth Factor 19 (FGF19), Incretins, Somatostatin, Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, Irisin. Non-limiting examples of steroid hormones that can be detected by the current invention include progesterone, aldosterone, testosterone, estradiol, and Cortisol. Additional examples of hormones that can be measured according to the current invention are well known to a person of ordinary skill in the art and such embodiments are within the purview of the current invention.

As used herein, the term "small molecule" refers to low molecular weight molecules (<900 daltons) that include lipids, monosaccharides, second messengers, other natural products and metabolites, as well as drugs and other xenobiotics. They are distinct from macromolecules such as proteins. A small molecule is able to enter cells easily because it has a low molecular weight. Once inside the cells, it can affect other molecules, such as proteins. This is different from drugs that have a large molecular weight, such as monoclonal antibodies, which are not able to get inside cells very easily.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art.

As used herein, the term "ligand" refers to a substance that forms a complex with a biomolecule to serve a biological purpose. In protein-ligand binding, the ligand is usually a molecule, which produces a signal by binding to a site on a target protein. The binding typically results in a change of conformational isomerism(conformation) of the target protein. In DNA-ligand binding studies, the ligand can be a small molecule, ion, or protein, which binds to the DNA double helix. The relationship between ligand and binding partner is a function of charge, hydrophobicity, and molecular structure. The instance of binding occurs over an infinitesimal range of time and space, so the rate constant is usually a very small number.

As used herein, the term "binding" refers to an association between proteins or nucleotides that occurs through intermolecular forces, such as ionic bonds, hydrogen bonds and Van der Waals forces. The association of docking is actually reversible through dissociation. Measurably irreversible covalent bonding between a ligand and target molecule is atypical in biological systems. Ligand binding to a receptor protein or to an allosteric transcription factor can alter the conformation by affecting the three-dimensional shape orientation. The conformation of a receptor protein or allosteric transcription factor composes the functional state. Ligands include small molecules, hormones, inhibitors, activators, and neurotransmitters.

As used herein, the term "fluorescent molecule" refers to a fluorescent chemical compound that can reemit light upon light excitation. Fluorescent molecules typically contain several combined aromatic groups, or planar or cyclic molecules with several $\pi$ bonds. Current fluorescence imaging probes typically consist of single conventional fluorophore (e.g., organic dyes, fluorescent proteins), fluorescent proteins (e.g., GFP) and semiconductor quantum dots (Q-dots). Single fluorophores are usually not stable and have limited brightness for imaging. Similar to dyes, the fluorescent proteins tend to exhibit excited state interactions which can lead to stochastic blinking, quenching and photobleaching. Fluorescent molecules are known in the art and include florescent proteins (e.g. CAP, WFP, BFP, and other GFP derivatives). Other suitable fluorescent molecules are known in the art and commercially available from, for example, Molecular Probes (Eugene, Oreg.). These include, e.g., donor/acceptor (i.e., first and second signaling moieties) molecules such as: fluorescein isothiocyanate (FITC)/tetramethylrhodamine isothiocyanate (TRITC), FITC/Texas Red™ Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X (ROX), FITC/tetramethylrhodamine (TAMRA), and others. In addition to the organic fluorophores already mentioned, various types of nonorganic fluorescent labels are known in the art and are commercially available from, for example, Quantum Dot Corporation, Inc. Hayward Calif.). These include, e.g., donor/acceptor (i.e., first and second signaling moieties) semiconductor nanocrystals (i.e., 'quantum dots') whose absorption and emission spectra can be precisely controlled through the selection of nanoparticle material, size, and composition.

As used herein, the term "semiconductor quantum dots" refers to fluorophores for multi-photon excitation. It has been shown that that quantum dots are unique donor fluorophores for FRET where multiple acceptor dyes can be positioned around the quantum dot (QD) to substantially enhance the overall rate of FRET between QD and proximal dyes.

As used herein, resonance energy transfer (FRET) refers to FRET is a distance-dependent interaction between the electronic excited states of two fluorescent molecules in which excitation is transferred from an excited donor molecule to an acceptor molecule without emission of a photon. The absorption spectrum of the acceptor must overlap the fluorescence emission spectrum of the donor. FRET, between donor and acceptor, occurs over distances that typically span a distance of at least 1 Å, or of at least 5 Å or of at least 10 Å, or of at least 20 Å, or of at least 30 Å, or of at least 40 Å, or of at least 50 Å, or of at least 60 Å, or of at least 70 Å, or of at least 80 Å, or of at least 90 Å, or 100 Å. As used herein, the term "biosensor" refers to an analytical device that combines the biological recognition element with a signal transducer to convert the response with analytes into a measurable signal which is proportional to the concentration of the analytes.

As used herein, the term "device" refers to an electrically addressable unit that performs some task, such as switching, storing a single bit of information, or sensing a particular molecule or class of molecules according to an embodiment of the present invention. Depending upon the embodiment, other examples of definitions also exist.

As used herein, the term "circuit" refers to a group of devices, each of which are designed to carry out similar tasks according to a specific embodiment. For example, a transistor is a switching device. A multiplier is a logic circuit constructed from many transistors, which is a circuit. As another example, a nanowire is a chemical sensing device. An array of nanowires each coated with a different molecular probe, constitutes a sensor circuit designed to sense many different molecular targets according to a specific embodiment. Depending upon the embodiment, other examples of definitions also exist.

The term "percent (%) amino acid sequence identity" or "% sequence identity to amino acids" with respect to a particular SEQ ID NO is defined as the percentage of amino acid residues in a candidate sequence that are identical with the amino acid residues in the comparative sequence identified by the SEQ ID NO, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); available on the world wide web at: blast.wustUedu/blast/README.html). WU-BLAST-2 uses several search parameters, most of which are set to the default values. The adjustable parameters are set with the following values; overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

As used herein, the term "integrated circuit" refers to a group of circuits, each design to carry out different specific tasks, but operating together to perform some larger function. For example, a multiplier circuit can retrieve two numbers from a memory circuit, multiply them together, and store them back into the memory circuit. Depending upon the embodiment, other examples of definitions also exist.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even±0.1% of the specified amount.

Also as used herein, "and/or" refers to and encompasses any and all possible combinations of one or more of the associated listed items, as well as the lack of combinations when interpreted in the alternative ("or").

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A method to identify an oxidase microbial redox enzyme (MRE) specific to a target analyte, the method comprising (a) contacting a sample comprising at least one MRE with a target analyte and at least one readout substrate (ReadS), wherein the target analyte is catalyzed by at least one microbial oxidase MRE to produce $H_2O_2$, and wherein the ReadS can be converted to a readout product (ReadP) in the presence of hydrogen peroxide, wherein the ReadP produces a detectable signal, (b) measuring the presence of the detectable signal produced by the ReadP, and (c) isolating and identifying the MRE by sequencing the gDNA in the sample.

2. The method of paragraph 1, further comprising contacting the sample with a readout Enzyme (ReadE), wherein the ReadE catalyzes the conversion of the ReadS to ReadP only in the presence of $H_2O_2$.

3. The method of paragraphs 1 or 2, wherein the sample comprising at least one MRE is present in a bacterial population comprising a genomic DNA (gDNA) encoding a plurality of MREs.

4. The method of paragraph 1, wherein the sample comprising at least one MRE is obtained from protein synthesis of a genomic DNA (gDNA) library encoding a plurality of MRE, where protein synthesis occurs in a cell-free manner.

5. The method of any of paragraphs 1-4, wherein the readout enzyme is a peroxidase.

6. The method of any of paragraphs 1-4, wherein the peroxidase is APEX2 or HRP.

7. The method of any of paragraphs 1-6, wherein the readout substrate is a hydrogen peroxide responsive probe, wherein the hydrogen peroxide responsive probe produces a detectable signal in the presence of hydrogen peroxide.

8. The method of paragraph 7, wherein detectable signal selected from any of: fluorescence, bioluminescence, chemiluminescence, optical signal, electrochemical signal.

9. The method of paragraph 7, wherein the hydrogen peroxide responsive probe produces an electrochemical signal, wherein the electrochemical signal is detected by current passed to an electrode.

10. The method of paragraphs 1-9, wherein the detectable is fluorescence.

11. The method of any of paragraphs 1-10, wherein the fluorescence is measured by FACS.

12. The method of any of paragraphs 1-11, wherein the Readout Substrate (ReadS) is Amplex™ UltraRed (AUR).

13. The method of any of paragraphs 1-12, wherein the Readout Enzyme is APEX2, HRP, or a functional variant thereof, and the readout substrate is Amplex™ UltraRed (AUR).

14. The method of any of paragraphs 1-10, wherein the hydrogen peroxide responsive probe is a boronate-based probe.

15. The method of paragraph 12, wherein the boronate-based probe is selected from any of: PY1, PO1, Hamovanillic Acid (HVA), Luminol, OPD, DCFH, ABTS, K iodine, or ABTS, 1a and 1b, PG1, PF1, PF3, PE1, RPF1, PC1, PY1-ME, PCL-1, Fl-B.

16. The method of any of paragraphs 1-13, wherein the hydrogen peroxide responsive probe is a non-boronate-based probe.

17. The method of any of paragraphs 1-16, wherein the sample comprises a genomic DNA (gDNA) library.

18. The method of paragraph 17, wherein the gDNA library comprises genomic DNA from any environmental source.

19. The method of paragraph 17, wherein the environmental source is selected from any of: water, soil, microbiome, feces, urine, plant sources, fungal cells, fossil energy source, Artic ice samples, Antarctic ice samples, water or permafrost sources, materials of volcanic origin, materials from soil or plant sources in tropical areas, oil samples, wastewater samples, or any environmental source comprising DNA.

20. The method of paragraph 18, wherein the water source is deep water, contaminated water, waste water.

21. The method of any of paragraphs 1-20, wherein the contacting the sample with the target analyte is contacting a droplet comprising the gDNA library with an analyte of interest, a peroxidase enzyme (PE) and a hydrogen peroxidase responsive probe is by droplet merging.

22. The method of any of paragraphs 1-21, wherein the method is performed in a high-throughput manner.

23. The method of any of paragraphs 1-22, wherein the method is performed on a microfluidic device.

24. A cell-free method of identifying a candidate oxidase microbial redox enzyme (MRE), comprising: (a) providing a library of nucleic acid sequences comprising genomic DNA (gDNA) obtained from at least one environmental source with one or more reagents for cell-free protein synthesis, (b) generating nano-volume droplets of the library and contacting the droplets with a target analyte, an readout substrate (ReadS), wherein the ReadS is converted to a readout product (ReadP) in the presence of $H_2O_2$, wherein the ReadP produces a detectable signal in the presence of a candidate oxidase MRE that is specific to the target analyte, (c) measuring the presence of a detectable signal produced from the ReadP, and (d) isolating the gDNA and cloning into a vector, wherein the gDNA encodes a candidate oxidase MRE that is specific to the target analyte.

25. The method of paragraph 24, wherein the ReadS is a converted to a readout product only in the presence of a readout enzyme (ReadE).

26. The method of paragraph 24, wherein the ReadE is a peroxidase enzyme.

27. The method of paragraph 26, wherein the peroxidase enzyme is APEX2 or HRP.

28. The method of paragraph 243, wherein the readout substrate is Amplex™ UltraRed (AUR), and wherein AUR is converted to resorufin which produces a detectable florescent signal.

29. The method of paragraph 24, wherein the ReadS is a hydrogen peroxidase responsive probe.

30. The method of paragraph 29, wherein the hydrogen peroxide responsive probe is a boronate-based probe.

31. The method of paragraph 30, wherein the boronate-based probe is selected from any of: PY1, PO1, Hamovanillic Acid (HVA), Luminol, OPD, DCFH, ABTS, K iodine, or ABTS, 1a and 1b, PG1, PF1, PF3, PE1, RPF1, PC1, PY1-ME, PCL-1, Fl-B.

32. The method of paragraph 25, wherein measuring is using FACS.

33. A library of expression vectors, each comprising at least one promoter, at least one nucleic acid sequence encoding an oxidase microbial redox-enzyme (MRE), a nucleic acid encoding a readout enzyme (ReadE) or a nucleic acid encoding a hydrogen peroxide responsive probe, wherein the at least one nucleic acid sequence encoding the MRE and nucleic acid encoding the ReadE or the hydrogen peroxide responsive probe are operatively linked to the at least one promoter.

34. The library of paragraph 33, wherein the Readout Enzyme is APEX2 or HRP.

35. The library of paragraph 33, wherein the nucleic acid encoding a hydrogen peroxide responsive probe encodes a hydrogen peroxide responsive probe selected from any of: Hyper1, Hyper2, Hyper3, HyPer-Red, roGFP-Orpl or roGFP-Tsa2.

36. The library of paragraph 33, wherein the at least one nucleic acid sequence encoding the oxidase MRE is obtained from genomic DNA (gDNA) obtained from an environmental source.

37. A plurality of cells comprising the library of expression vectors of paragraph 33.

38. A method of screening, comprising:
(a) contacting a library of expression vectors of paragraphs 33-36 with a target analyte and a readout substrate (ReadS), wherein the ReadS can be converted to a readout product (ReadP) in the presence of hydrogen peroxide, wherein the ReadP produces a detectable signal,
(b) measuring the presence of a detectable signal produced from the readout product,
(c) isolating the expression vector encoding the MRE that is specific to the target analyte.

39. The method of paragraph 38, wherein the readout substrate is Amplex™ UltraRed (AUR), and wherein AUR is converted to resorufin in the presence of hydrogen peroxide to produce a florescence signal.

40. The method of paragraph 38, wherein measuring is using FACS.

41. The method of any of paragraphs 38-40, wherein the method is performed in a high-throughput manner.

42. The method of paragraph 41, wherein the method is performed on a microfluidic device.

43. A method for identifying an oxidase microbial redox enzyme (MRE) to a target analyte, comprising: (a) contacting a library comprising a genomic DNA (gDNA) with an analyte of interest, wherein the genomic library is generated from the genomic DNA obtained from a biological or an environmental source and (b) contacting with at least one of:
i. a readout enzyme (ReadE) and readout substrate (ReadS), wherein the ReadS is converted to a readout product (ReadP) in the presence of the ReadE and hydrogen peroxide, and wherein the ReadP produces a detectable signal,
ii. NAD(P) or a NAD(P)H-dependent responsive probe (NAD(P)-DP), wherein the NAD(P)-dependent probe can be reduced from an oxidized form (NAD(P)-DPox) to a reduced (NAD(P)-DPred) in the presence of a NAD(P)-dehydrogenase enzyme to produce a detectable signal;
iii. a NAD(P)-independent responsive probe (NIP), wherein the NAD(P)-independent probe can be oxidized from reduced form (NlPred) to a reduced form (NIPox) to produce a detectable signal;
(d) measuring the presence of a signal produced from any one of: the readout product (ReadP), NAD(P)-DPred, or NIPox
i. wherein ReadP is produced when the analyte is catalyzed by an oxidase enzyme,
ii. wherein NAD(P)-DPred is produced when an analyte is catalyzed by a dehydrogenase enzyme,
iii .wherein NlPred is produced when an analyte is catalyzed by a dehydrogenase enzyme,
(e) isolating the gDNA from which a signal from of ReadP, NAD(P)-DPred or NIPox was produced,
(f) sequencing the gDNA to identify the redox-enzyme that catalyzes the analyte of interest, wherein the redox-enzyme is an oxidase enzyme, a dehydrogenase enzyme or a NAD-dehydrogenase enzyme.

44. The method of any of paragraphs 1-43, wherein the analyte is selected from any of a small molecule, toxin, neurotransmitter, steroid, immunomodulator, metabolite, hormone.

45. The method of paragraph 44, wherein the hormone is selected from any of the group of: progesterone, estradiol, estrone, estriol, progesterone, testosterone, aldosterone, prednisolone, androstadienone, cortisol, cholesterol.

46. The method of any of paragraphs 1-45, wherein the detectable signal is a fluorescent molecule or a quantum dot (QD).

47. The method of any of paragraphs 1-46, wherein the fluorescent molecule comprises a FRET acceptor and a second fluorescent reporter comprises a FRET donor.

48. The method of any of paragraphs 1-47, wherein the fluorescent molecule is selected from the group consisting of a quantum dot, a fluorescent dye, a fluorescent protein, and combinations thereof.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Materials and Methods

Strain Selection: *Pseudomonas putida* (Trevisan) Migula (ATCC® BAA-2546™) was purchased from ATCC® (Manassas, Va.) and linked with a corresponding GenBank accession number (CP002870.1). The strain is aerobic and was propagated and grown in ATCC® Medium 18: Trypticase Soy Agar/Broth at 30° C. as recommended by ATCC®.

Strain Growth Curve: In order to determine the doubling time of the strain, growth curves were performed. All growth curves were done in 96 well flat clear bottom black polystyrene TC-treated microplates (Corning Inc.™, Corning, N.Y.). Measurements were taken with an Infinite M200 Pro™ (TECAN Group Ltd., Medford, Mass.) spectrophotometer at 30° C. Readings were performed over 96 cycles of 15 minutes each at 600 nm absorbance with 25 flashes in a 3×3 (XY-Line) type ReadS per well. In between ReadS there was orbital shaking at 150 rpm frequency for a total of 10 minutes. To first characterize the growth alone, a ½ serial dilution of 9 concentrations from 0.5-0.0020 $OD_{600}$ nm were prepared in M18 media. Then each concentration was measured as previously described by the TECAN microplate reader and normalized against a media background control in technical triplicate. Afterward, an appropriate starting concentration of cells was chosen which shows a substantially long lag-phase, linear log phase, and a plateau of stationary-phase.

Strain Solvent Growth Curve: Once an appropriate starting cell concentration was chosen, a secondary growth curve was performed to test the toxicity levels of the solvent used to dissolve nicotine. Since nicotine is readily soluble in water that was the solvent of choice. *P. putida* S16 was incubated under microplate reader conditions previously mentioned at a starting OD determined by the first growth curve with $H_2O$ at ½ serial dilutions for a total of eight concentrations (50-0.39%) tested in technical triplicate. Two controls were included per solvent; a positive control without solvent and a media control which allowed for appropriate normalization. Solvent exposure growth curves allowed for choosing the maximum amount of solvent concentration that *P. putida* S16 would sustain while maintaining relative viability in order to determine a range of nicotine concentrations which could be used.

Strain Nicotine Growth Curve: A tertiary growth curve was performed to test the toxicity levels of nicotine specific to *P. putida* S16. The strain was incubated under microplate reader conditions previously mentioned at a starting OD determined by the first growth curve and the highest solvent concentration with nicotine at ½ serial dilutions for a total of seven concentrations tested in singlet. Three controls were included; a positive control with the highest tolerable solvent concentration (%), a positive control with media, and a media control alone which allowed for normalization. Nicotine exposure growth curves allowed for choosing the maximum amount of nicotine concentration that *P. putida* S16 would sustain while maintaining relative phenotypic viability.

Strain RNA Extraction: Cells were grown in 5 mL M18 at a starting $OD_{600}$ of 0.005 with 21.6 µM nicotine in 14 mL polypropylene round-bottom tubes (Corning Inc.™, Corning, N.Y.) in singlet. The cells were incubated at 30° C. with continuous orbital shaking at 150 rpm until the end of lag-phase (3 hours) and mid-log phase (7.5 hours) from the start of inoculation. Controls were grown in the same conditions without nicotine. Afterward, samples were removed and a 1:1 ratio of RNAprotect Bacteria Reagent™ (Qiagen Inc.™, Germantown, Md.) was added followed by spinning down at 4° C. for 10 minutes at 4000×g. Supernatant was removed and the pellet re-suspended in 300 µL of RNAprotect™ and transferred into 2.0 mL Safe-Lock Tubes™ (Eppendorf™, Hauppauge, N.Y.). The samples were then spun down at 4° C. for 10 minutes at 10000×g. RNA extraction was done by Qiacube™ (Qiagen Inc.™, Germantown, Md.) set to the RNeasy Protect Bacteria Mini Kit™ protocol of bacterial cell pellet with enzymatic lysis. Lysis buffer was prepared as described by the protocol with the exception of the addition of 150 mg/mL lysozyme (Sigma-Aldrich Corp.™, St. Louis, Mo.) and 20 mg/mL proteinase K (F. Hoffmann-La Roche Ltd™, Indianapolis, Ind.) all diluted in 1×TE buffer. RNA samples were subsequently quantified using Qubit RNA HS Assay Kit™ (Thermo Fisher Scientific Inc.™, Cambridge, Mass.) and analyzed using a RNA 6000 Pico Kit™ (Agilent Technologies Inc.™, Santa Clara, Calif.) in a 2100 Bioanalyzer™ (Agilent Technologies Inc.™, Santa Clara, Calif.). RNA samples were either immediately used for RNA-Seq library preparation or stored long-term at −80° C. after addition of 1 µL RNase Inhibitor, Murine (New England Biolabs™ Mass.).

RNA-Seq Library Preparation: After RNA samples have been quantified and analyzed they were DNase treated using TURBO™ DNase 2 U/4 (Thermo Fisher Scientific Inc™., Cambridge, Mass.) and cleaned using Agencourt RNA-Clean™ XP SPRI beads (Beckman Coulter, Inc™., Brea, Calif.). RNA-Seq libraries were then produced from these samples using a modified ScriptSeq v2 RNA-Seq Library Preparation Kit™ (Illumina Inc.™, San Diego, Calif.) ensuring use of unique index primers through ScriptSeq™ Index PCR Primers (Sets 1-4) 48 rxns/set (Illumina Inc.™, San Diego, Calif.). Libraries were quantified by both a Qubit dsDNA HS Assay Kit™ Thermo Fisher Scientific Inc.™ Cambridge, Mass.) and by Bioanalyzer™ with the High Sensitivity DNA Kit™ (Agilent Technologies Inc.™, Santa Clara, C). The samples were then pooled to 2 nM and submitted to a sequencing core facility. Whole transcriptome RNA sequencing was performed by a NextSeq 500™ (Illumina Inc.™ San Diego, Calif.) at high output (400 M ReadS) with 75 bp paired end sequencing read length. The data was then analyzed in-house through a proprietary lab computational pipeline.

Enzyme Expression and Purification: NicA2 was recombinantly produced with poly-histidine tags in *Escherichia coli*. Plasmids containing the gene for NicA2 were obtained through collaborative exchange (see e.g., Xue et al. 2015, supra). Plasmids were chemically transformed into *E. coli* BL21 (DE3) (New England Biolabs™, Mass.) with induction of lysogeny broth cultures at $OD_{600}$ 0.6 to 0.8 using 1 mL of 1M isopropyl b-D-1-thiogalactopyranoside (IPTG) before analysis by SDS-polysaccharide gel electrophoresis (SDS-PAGE). Confirmed expression prompted 1 L cultures for expression and protein purification through disruption of cells using lysozyme and by passing cell lysate over a HisPur™ Ni-NTA Resin-packed column (Fisher Scientific™, Pittsburgh, Pa.). Final protein products were quantified using the Pierce Micro BCA Protein Assay™ kit (Fisher Scientific™ Pittsburgh, Pa.).

In Vitro Enzyme Characterization: Amplex™ UltraRed assays were performed per instruction of the manufacturer (Thermo Fisher Scientific, Cambridge, Mass.). Final concentrations of Amplex™ UltraRed, 500 uM, and HRP, 1 U/mL, in a total volume of 20 µL were used. Nicotine and NicA2 concentrations varied with experiment. All measurements of fluorescence were done in a 384 well flat bottom black polystyrene microplate (Corning Inc.™, Corning, N.Y.) and read in an Infinite M200 Pro™ (TECAN Group Ltd.™, Medford, Mass.) spectrophotometer at room temperature with the excitation set to 490 nm and emission at 585 nm. Readings were done over 1 hour with each well read every 30 seconds.

Sensor Preparation: Electrochemical experiments were performed with VersaSTAT MC™ (Ametek Inc.™, Pennsylvania, Pa.). Sensors were prepared with Screen-Printed Prussian Blue/Carbon Electrode (Metrohm USA™, Riverview, Fla.). Equal volume of NicA2 (400 µM) and 1 wt % chitosan in 0.5 wt % acetic acid (Sigma-Aldrich Corp.™, St. Louis, Mo.) were mixed. NicA2 was immobilized onto the SPEs by drop-casting 10 µL of this mixture onto the working electrode. The sensors were allowed to dry overnight at 4° C. with no light prior to use.

Sensor Characterization: In order to quantify the current response of the nicotine biosensor, chronoamperometric experiments were performed where various concentrations of nicotine in PBS (0-1000 µM) were deposited onto SPEs with 2 nmol NicA2.

Chronoamperometric responses were recorded over time, with a potential −0.2 V (versus Ag/AgCl). At the beginning of the experiment, 30 µL 1×DPBS was added to the biosensor, followed by an addition of 30 µL nicotine solution at predefined time point. To evaluate the selectivity of the sensor chronoamperometric responses to nicotine were measured in the presence of the common interferents at relevant physiological concentrations in sweat (see e.g., Table 4). Addition of 30 µL 200 µM nicotine solution to 30 µL mixture was performed at a predefined time point and the current was recorded over time. Similar experiments were performed to evaluate the selectivity of the sensor to cotinine. Current was recorded where 30 µL 200 µM nicotine solution was added to 30 µL cotinine solutions. Additionally, to confirm that the current response observed was due to NicA2, myosmine, an inhibitor of NicA2, was added in the middle of a chronoamperometric experiment.

Table 4 shows interferents and their estimated concentrations in human matrices. A sweat mixture was prepared based on the values in Table 4 and tested (see e.g., FIG. 22C).

| | Expected Concentrations (mM) | |
|---|---|---|
| Interferent | Sweat | Interstitial Fluid |
| L-(+)-Lactic acid | 5 | 0.8 |
| Ascorbic acid | 0.01 | 0.3 |
| Uric acid | 0.06 | 0.4 |
| Dopamine | 0.001 | <nmol |
| (−)-Epinephrine | 0.005 | 1.20E−01 |
| Creatinine | 84 | 0.13 |
| D-(+)-Glucose | 0.17 | 0.7 |
| Sodium | 36 | 136 |
| Calcium | 1.1 | 1.5 |
| Magnesium | 0.3 | 0.6 |
| Potassium | 11 | 3.2 |
| Phosphate | 40 mg/L | 0.6 |
| Albumin | ND | 0.18 |
| Amino acids | 6 | 2.6 |
| Cotinine | N/A | N/A |

Example 1

General Platform for Identification of MRE Oxidase Enzymes

There is significant need to measure the presence & concentration of molecules (hormones, toxins, etc.) in complex samples (blood, saliva, drinking water, etc.) and in real-time. This space is currently limited to blood glucose measurements via the ubiquitous finger prick tests available at local pharmacies, and is, itself, a billion dollar market. These blood glucose tests rely on enzymes which convert biological signals (glucose concentration) into electrical signals (electrons) that can be read by an electronic device in real-time. Though the blood glucose meter is the only commercially successful sensor of it's type, novel sensors which detect new molecules could easily be generated using the preexisting infrastructure and knowledge, which would disrupt the entire real-time sensing market. Unfortunately, we lack a general platform that we can leverage to identify novel enzymes from the environment which can detect new and interesting molecules. To address this need we have developed a general platform that can be used to identify novel oxidase enzymes capable of detecting molecules of interest. The platform will require two inputs from the user: 1) a genomic DNA (gDNA) library from which to screen for novel oxidase enzymes, and 2) the molecule the user is interested in sensing. Given these two inputs, the platform will detect oxidases responsive to the analyte of interest and separate out the DNA which contains the oxidase 'hit' which could be sequenced downstream and used to build a biosensor.

The first part of the platform, the creation of the gDNA library can be performed in two ways. The first would be to use a commercially available cloning kit, CopyControl Fosmid Library Production Kit (Lucigen #CCFOS059), and the other would be to use an in-house developed protocol.

The second part of the platform, the genetic circuit used to identify oxidase 'hits', relies on a commercially available chemical probe, Amplex™ UltraRed (Thermo Fisher Scientific #A36006). While this probe has been used in a number of diagnostic tests, it has not been used in a platform to screen for novel MRE enzyme function. Our platform will be the first of its kind to use a peroxidase enzyme, APEX2, for high-throughput functional screening of oxidase enzymes.

gDNA libraries of metagenomic samples can be prepared in one of two ways. The first can use a commercially available cloning kit, CopyControl Fosmid Library Production Kit (Lucigen #CCFOS059), and the other would be to use an in-house developed protocol. If using the in-house protocol, the main steps would be to isolate the gDNA using the GenElute Bacterial Genomic DNA kit (Sigma-Aldrich #NA2110-1KT). Then fragment the gDNA using a g-TUBE (Covaris #520079) followed by end-repairing the fragments with the Quick Blunting Kit (NEB #E12015). The vector backbone, which the fragmented gDNA will be inserted into, was engineered to have a single Pm1I (NEB # #R05325) site between a T7 promoter, a ribosome binding site (RBS), and a T7 terminator. This single blunt-end restriction enzyme site would allow for the blunt-end ligation of vector to gDNA fragments. To prepare the vector it should be digested with Pm1I and then dephosphorylated with the Quick Dephosphorylation Kit (NEB #M0508S) to prevent self-ligation. Finally, the vector and fragmented gDNA should be ligated overnight and transformed by electroporation into *E. coli* TOP10 (Thermo Fisher Scientific #C404010) and incubated overnight on carbenicillin agar plates. A sufficient number of plates will be necessary to generate a library of sufficient diversity. Once the colonies have grown sufficiently, plates will be scraped and pooled into fresh LB media with carbenicillin, which will serve as the initial gDNA library. Plasmid DNA containing gDNA fragments from this library culture will be purified (Qiagen #27104) so that the DNA library can be moved into a new strain of *E. Coli* for screening assays.

The isolated plasmids containing gDNA would then be transformed into an in-house developed strain of *E. coli*. This strain, Rosetta2 (DE3), constitutively expresses an engineered ascorbate peroxidase, APEX2, which serves as the selection "chassis" for screening. APEX2 is an enzyme which catalyzes the generation of a fluorescent product (resorufin) from Amplex™ UltraRed (AUR) only in the presence of hydrogen peroxide ($H_2O_2$). Cells containing a gDNA fragment encoding an oxidase MRE enzyme which degrades the analyte of interest will become fluorescent due to the production of $H_2O_2$ by that oxidase enzyme. This is because $H_2O_2$ becomes a substrate, along with AUR, for APEX2 to produce a fluorescent product. Fluorescent cells are then identified and sorted by a fluorescence-activated cell sorting (FACS) machine. They will then be grown in 2×YT media and plated on carbenicillin agar plates overnight. The colonies will then be inoculated into fresh LB media with carbenicillin and their plasmids isolated (Qiagen #27104). Isolated plasmids will be sequenced to identify the gene responsible for producing the oxidase enzyme responsive to the analyte of interest.

Possible variations of the invention include modifying the APEX2 enzyme into either an evolved version with improved enzyme kinetics or another HRP derivative. Another modification includes changing AUR into another $H_2O_2$ responsive probe like PY1, PO1, Amplex™ UltraRed, Hemovanillic acid (HVA), Luminol, OPD, DCFH, ABTS, K iodide, or ABTS. Other possibly changes include changing APEX2 into another enzyme which is sensitive to other enzyme products. For example, if the targeted enzyme were to be changed from an oxidase to a dehydrogenase the product of interest would change to NAD or NADH. Possible enzyme products include NAD, NADH, NADP, NADPH, $O_2$, and $H_2O$. One can vary the method disclosed herein to use transcription factors (TFs) in order to respond to $H_2O_2$. One such modification would be use of OxyR, a TF responsive to $H_2O_2$, to regulate GFP expression downstream of it's binding site, or other genetically-encoded $H_2O_2$ probes as disclosed herein. Another modification would be a different mode of detection instead of fluorescence. This might include luminescence or optical readouts.

In some embodiments, to make the assay a high-throughput assay, one could screen for fluorescence bacteria with a microfluidic device. For example, one could grow the gDNA library in 2×YT media to mid-log phase and then encapsulating individual bacterial cells in nL sized droplets of fresh media using an in-house fabricated microfluidic droplet generator device. Cells within droplets would then be incubated at 37° C. to allow for cell growth for 2 hours, followed by addition of 5 µM AUR with the analyte of interest to be screened at 1 mM via picoliter injection or droplet merging. Merged droplets will be incubated for 3 hours within the microfluidic device to allow for enzyme-mediated degradation of the molecule of interest which will result in a fluorescent signal accumulation within the cell due to AUR reduction by APEX2. Droplets will then be sorted based of fluorescence intensity, pooled into a collection tube, and DNA extracted using a commercially available kit (Qiagen #27104). Purified DNA will be re-transformed into *E. coli* TOP10 (Thermo Fisher Scientific #C404010) via electroporation, and individual colonies will be grown in liquid culture overnight at 37oC. Plasmid DNA from these cultures will be purified and sequenced for identification of enzyme hits.

In some embodiments, one could modify the assay described herein to screen individual plasmids of the gDNA library ex-vivo. These droplets would contain all the necessary components to express the plasmid which when incubated with the analyte of interest would produce fluorescence. These droplets would be sorted the same way as described previously.

Example 2

Characterization of the MRE assay using NicA2 microbial redox enzyme

A. Genomic Mining

Figure 18:
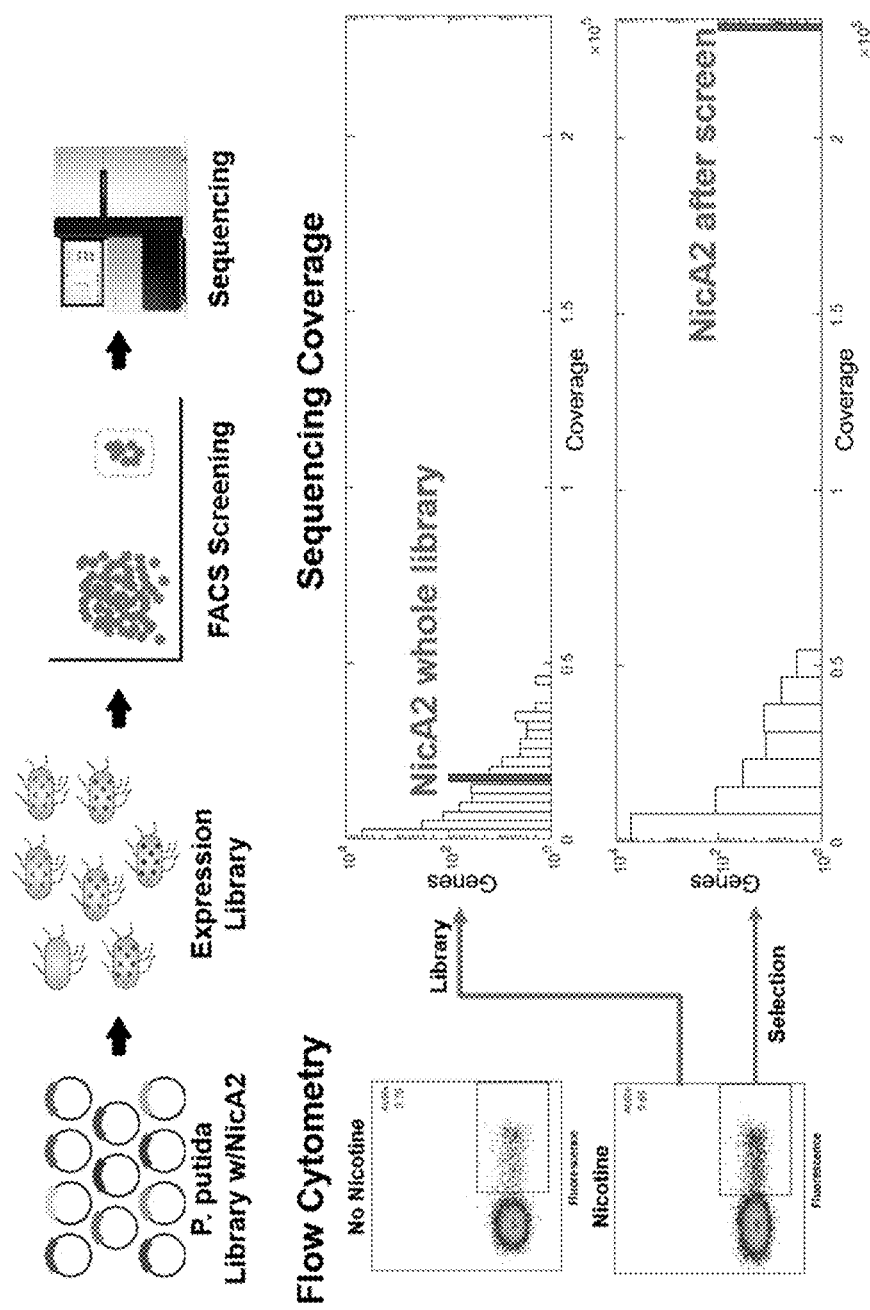
FIG. 18 is a schematic of an exemplary experimental setup to test for the enrichment of an oxidase using the screening technology described herein. Rosetta2 (DE3) cells containing a plasmid expressing apex2 and a *Pseudomonas putida* S16 gDNA library with and without nicotine were prepared and ran through on the FACS. From the sample with nicotine events from the non-fluorescent gate and the fluorescent gate were sorted. NGS analysis of the sorted cells revealed an enrichment of the oxidase gene nicA2.
Figure 20:
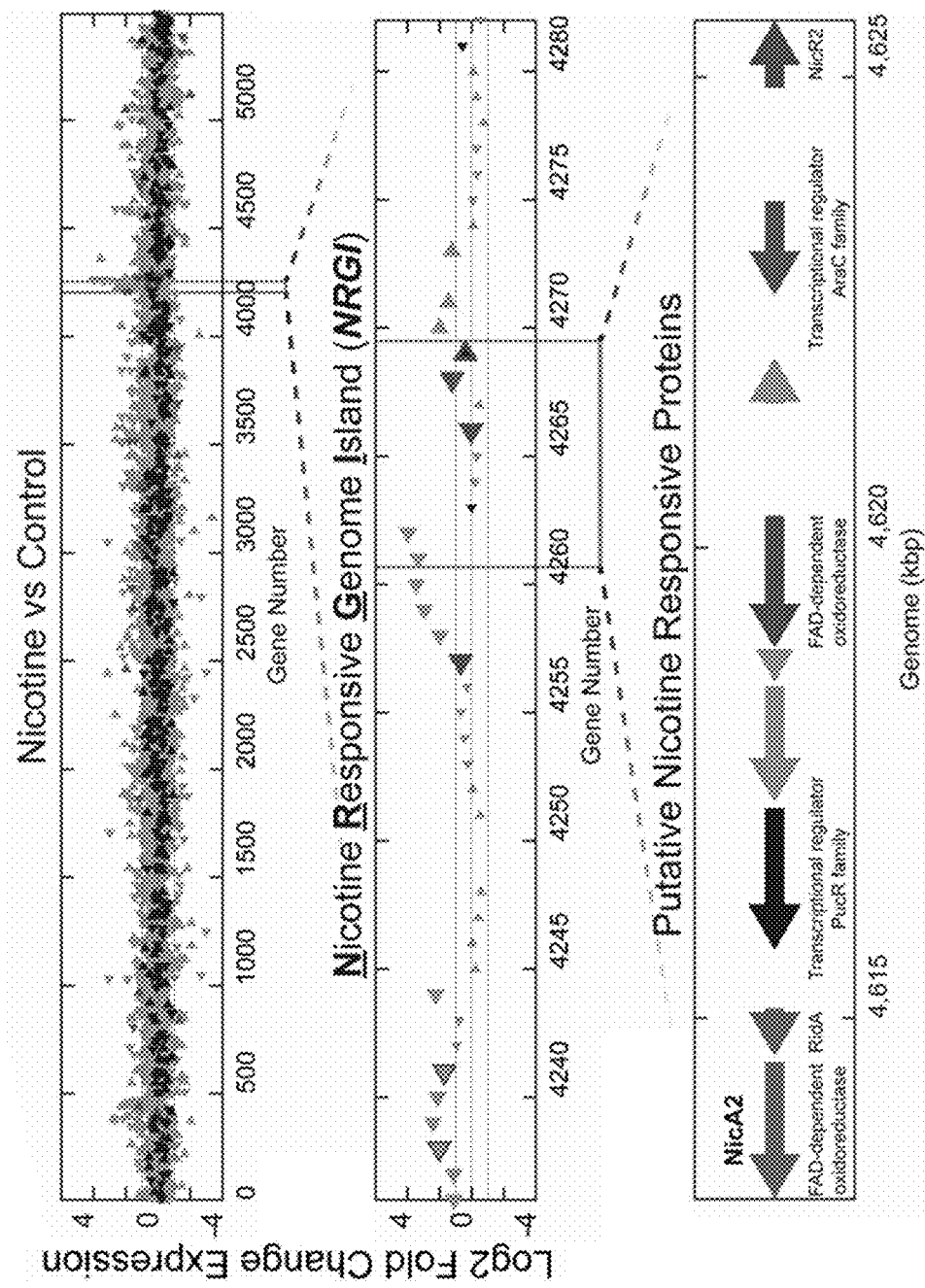
FIG. 20 is a series of graphs showing that RNA-Seq correctly identified the reported nic2 nicotine degrading genome cluster. In the nic2 cluster, the nicotine oxidoreductase enzyme gene (nicA2) is the highest differentially expressing redox enzyme which was used to develop an enzyme-based electrochemical nicotine biosensor described herein.

As an exemplary, proof-of-principal experiment to demonstrate the method and assays described herein can be used to identify redox-enzymes from microbes, the inventors used nicotine as an exemplary analyte to identify a redox-enzyme specific for nicotine. As described herein, to identify a redox enzyme specific to nicotine, RNA-Seq with was performed with and without nicotine in *P. putida* S16. In order to see a distinct change in the transcriptome expression levels without drastically affecting bacterial physiological growth, serial dilution growth curves were performed the key genomic island, nic2 was identified as responsive to nicotine using computational analyses (see e.g., FIG. 18 or 20). In the nic2 genomic island, the most highly differentially expressed enzyme encoding gene was nicA2, the target oxidoreductase enzyme. These results validated the screening pipeline and showcased the ability to isolate biosensing parts from microbes which can be used for device fabrication.

Although it has been known since the 1950's that certain strains of bacteria degrade nicotine, the pathway by which this occurs has only recently been discovered. In *P. putida* S16, the nicotine sensitive gene cluster, nic1, includes nicotine oxidoreductase (NicA1) and HSP hydroxylase (HspA) while the nic2 cluster encodes another nicotine oxidoreductase NicA2, later identified as a MAO (see e.g., Tang et al. 2013, PloS Genetics 9(10) e1003923). Deleting the nicA2 gene produces a strain that no longer degrades nicotine, confirming the importance of NicA2 in the nicotine degradation pathway. To identify the nicotine specific redox enzymes, RNA-Seq was performed on *P. putida* S16 in the presence and absence of nicotine. The optimal RNA-Seq experimental conditions were selected by varying the bacterial inoculation, solvent, and nicotine concentrations used in the serial dilution growth assays so as to provide a distinct change in the transcriptome expression levels without drastically affecting bacterial physiological growth. Subsequent computational analyses revealed the key genomic island, nic2, and that the most highly differentially expressed enzyme encoding gene was nicA2, the target MAO (see e.g., FIG. 18 or 20). The nicA2 gene was cloned into a recombinant vector with a histidine tag and expressed (~10 mg/mL). The protein was purified via FPLC and SEC. NicA2 exhibited increased selectivity, but reduced catalytic activity compared to redox enzymes such as glucose oxidase ($GO_X$) and lactate oxidase ($LO_X$) (see e.g., Table 2; see e.g., Xue et al. 2015, J Am Chem Soc 137(32) 10136-9, the content of which is incorporated herein by reference in its entirety). This demonstrated that the NicA2 enzyme was the first enzyme in the pathway responsible for metabolizing nicotine and so it was the main target to see if a RNA-Seq based approach could identify redox enzymes to build enzyme-based biosensors.

Accordingly, the Nic2A oxidase MREs was identified using RNA-sequencing. The same method can be used to identify oxidoreductases, oxidases and other redox enzymes that catalyze or degrade a number of different analytes, however, the MRE assays, including the cell-based and cell-free MRE assays described herein can identify MREs at a much more efficient and high-throughput system. Exemplary analytes for screening using the MRE assays described herein include, for example, but are not limited to target steroids: estradiol, estrone, estriol, progesterone, testosterone, aldosterone, prednisolone, androstadienone, hydrocortisol, cortisol, and cholesterol. Bacteria will be exposed to each hormone, and control media, at concentrations determined from growth curves, and RNA harvested at lag, log, and stationary phase. RNA will be extracted using standard procedures, and barcoded RNA-Seq libraries produced using Illumina ScriptSeq Library Kits, and multiplexed sequencing performed on an Illumina NextSeq Sequencer using 75 bp single-end ReadS. ReadS were aligned to a reference sequence. Identified redox-enzymes genes can be cloned and/or synthesized with a Strep-tag, codon adapted as necessary, inserted into standard expression vectors, and transformed into *E. coli*. redox enzymes can then be expressed and purified.

NicA2 Enzyme Characterization

The FAD-binding nicotine oxidoreductase, NicA2, is an essential enzyme of the pyrrolidine pathway which converts nicotine to n-methylomysomine (see e.g., Tararina et al. Biochemistry 2016, 55 (48), 6595-6598, the content of which is incorporated herein by reference in its entirety). The nicA2 gene was cloned into a recombinant vector, expressed, purified, and characterized. Kinetic values of NicA2 showed increased selectivity, but reduced catalytic activity compared to well-studied redox enzymes such as glucose oxidase ($GO_X$) and lactate oxidase ($LO_X$) (see e.g., Table 2; see e.g., Xue et al. 2015, J Am Chem Soc 137(32) 10136-9, the content of which is incorporated herein by reference in its entirety). The NicA2 enzyme was also reported to have impressive stability as it was able to retain activity over 3 weeks at 37° C. in HEPES buffer at pH 7.4 (see e.g., Xue et al. 2015, supra). (see e.g., Table 2).

TABLE 2

NicA2 is a more selective, yet slower redox enzyme compared to $GO_X$ and $LO_X$.

| Enzyme | $K_M$ | $k_{cat}$ | $k_{cat}/K_M$ | $1/k_{cat}$ |
|---|---|---|---|---|
| Nicotine oxidoredactase (Nic A2) | 43.5 ± 4.7 nM | (6.64 ± 0.17) * $10^{-3}$ s$^{-1}$ | 152.64 s$^{-1}$mM$^{-1}$ | 150.6024 s |
| Glucose oxidase ($GO_X$) | 33-110 mM | 1118.81 s$^{-1}$ | 22.04 s$^{-1}$mM$^{-1}$ | 0.000894 s |
| Lactate oxidase ($LO_X$) | 0.94 mM | 280 s$^{-1}$ | 297.87 s$^{-1}$mM$^{-1}$ | 0.00357 s |

Figure 21A:
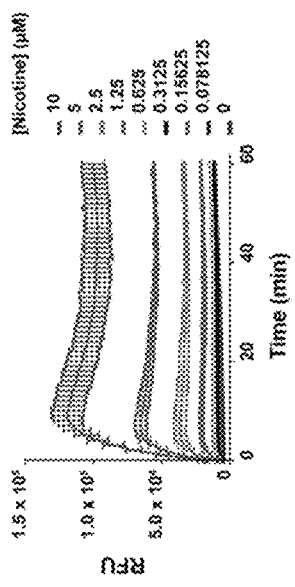
FIG. 21A-21D is a series of schematics and graphs. The Amplex™ UltraRed assay showed that fluorescence is analyte limited, not enzyme limited, and that the signal has a 1:1 dependence on the concentration of analyte present.
Figure 21B:
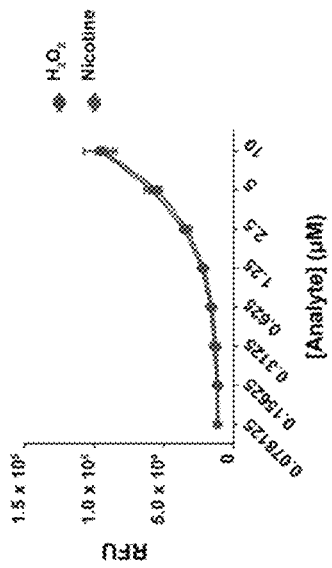
Figure 21C:
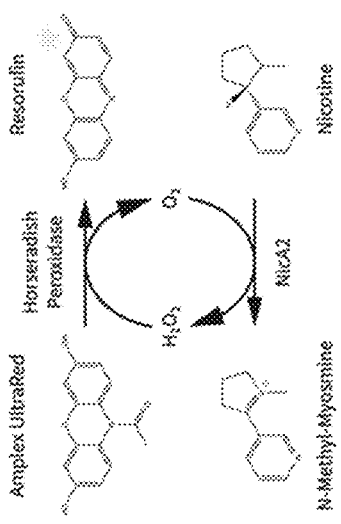
Figure 21D:
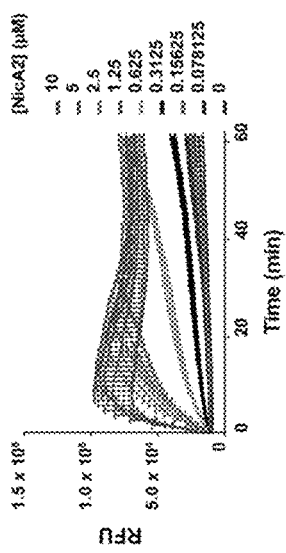

It is known that NicA2 is an oxidoreductase but its mechanism of $H_2O_2$ production from nicotine was not yet characterized. This information was critical for engineering an electrochemical biosensor because the ratio of $H_2O_2$ produced from a single nicotine molecule directly affects the current response in an electrochemical setup and therefore the final determined analyte concentration in a solution. NicA2 $H_2O_2$ production was characterized through the Amplex™ UltraRed assay (see e.g., FIG. 21A). In the presence of nicotine, NicA2 converts the analyte to n-methyl-myosmine and $H_2O_2$. In the presence of $H_2O_2$, horseradish peroxidase (HRP) converts $H_2O_2$ and Amplex™ UltraRed into oxygen and resorufin, a fluorescent molecule. The fluorescent readout of resorufin was therefore used to assess $H_2O_2$ production. Under a serial dilution of nicotine and the same amount of NicA2 there were corresponding levels of fluorescence decrease (see e.g., FIG. 21B). With a consistent amount of nicotine in solution and a serial dilution of NicA2, there was no change in fluorescence, but only in the rate of $H_2O_2$ production (see e.g., FIG. 21C). This indicated that $H_2O_2$ production was not enzyme limited, but substrate limited. The final crucial assessment was to know the ratio of $H_2O_2$ production compared to analyte addition. In order to determine this a calibration curve of $H_2O_2$ was performed and the fluorescence levels were compared to that of nicotine addition at the same concentrations (see e.g., FIG. 21D). It was found that NicA2 produces $H_2O_2$ from nicotine at a 1:1 ratio. Therefore, NicA2 produces equivalent fluorescence with the AmplexT™ UltraRed assay and current electrochemically with nicotine and $H_2O_2$.

Example 3

Optimization of the Cell-Based MRE Assay

Figure 33C:
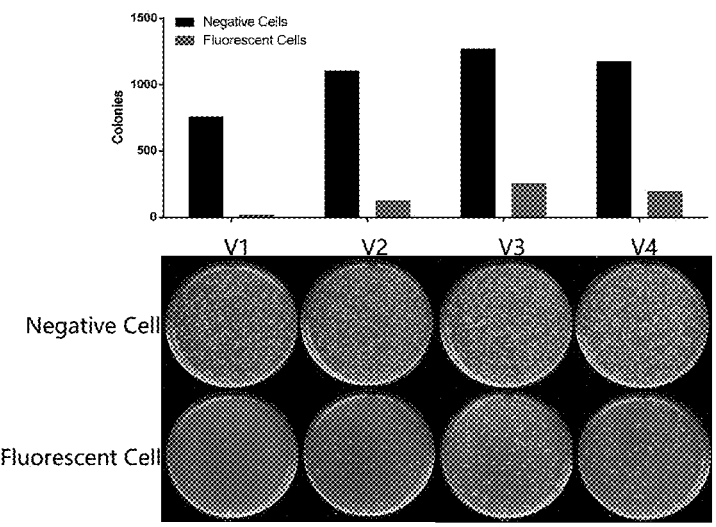
Figure 34:
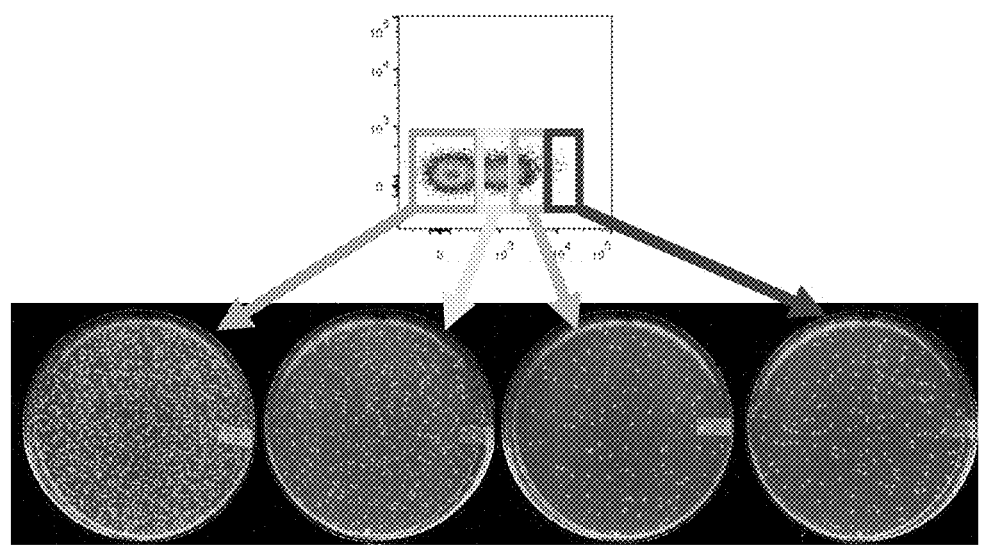
FIG. 34 shows post-cell viability is inversely correlated with AUR fluorescence in nicA2 expressing Rossetta2 cells through plating post-FACS cells on agar plates and counting colonies.
Figure 36A:
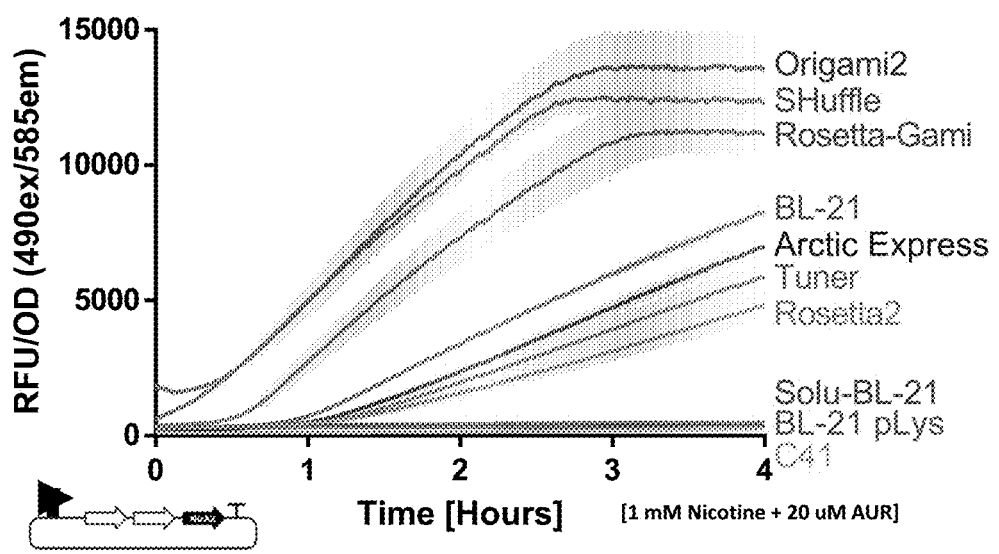
FIG. 36A-36D shows optimization of the cell-based MRE assay.
Figure 36B:
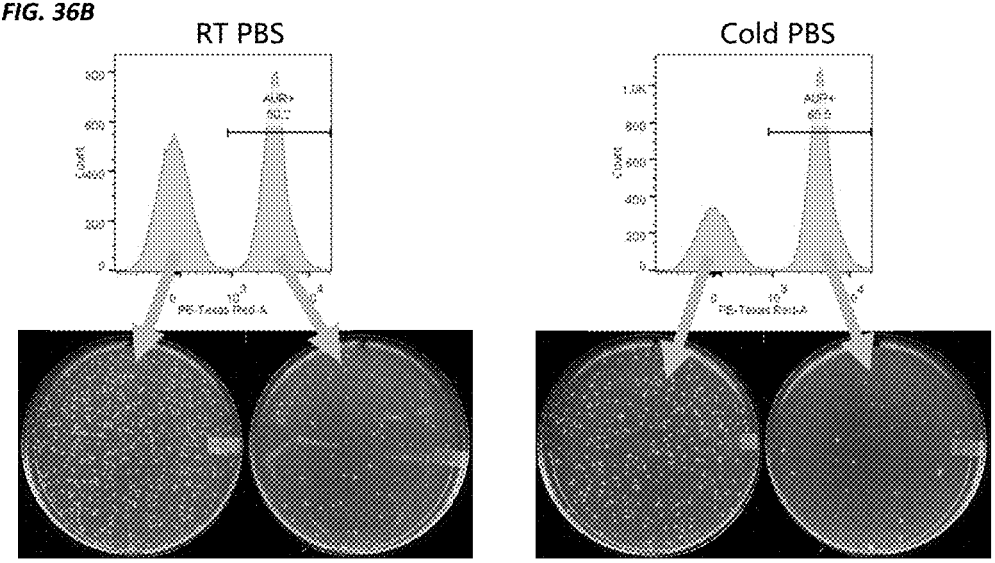
Figure 36C:
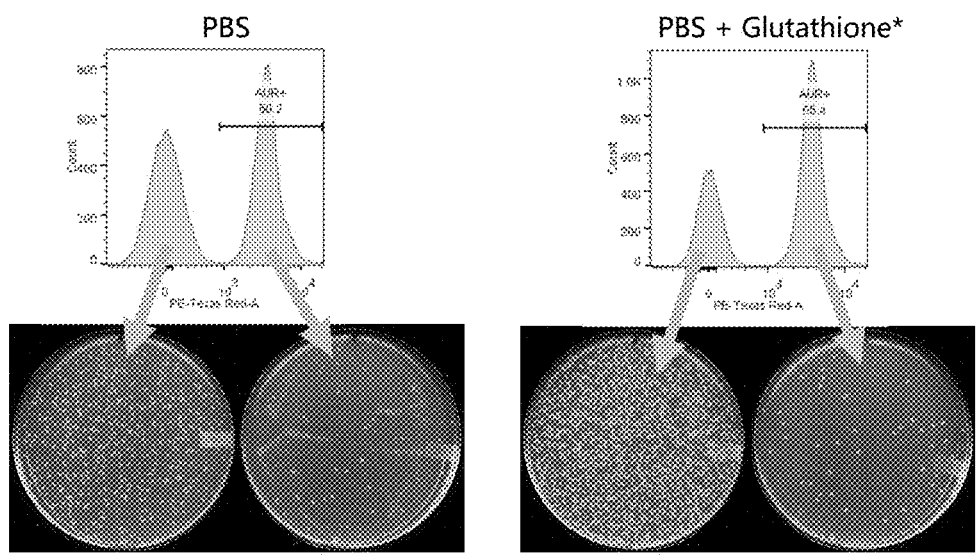
Figure 36D:
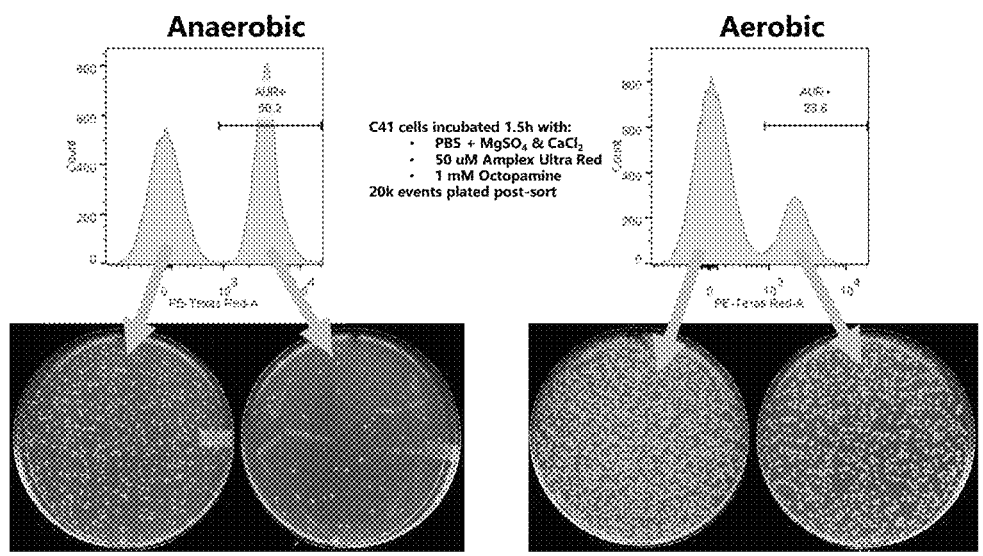
Figure 38:
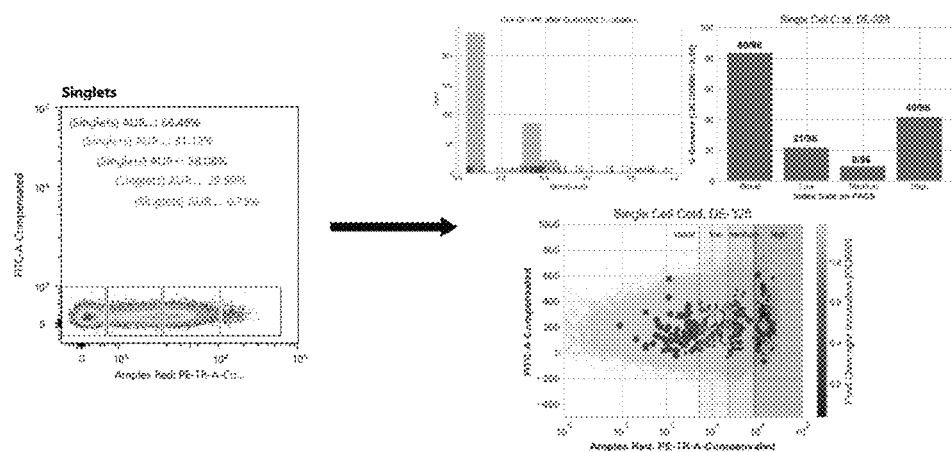
FIG. 38 shows the results of improved parameters of the cell-based MRE assay. Combined with FIG. 35B the optimized parameters include, but are not limited to: a wider FACs sorting nozzle (130 μM); anaerobic incubation during induction and analyte treatment; larger drop-sort volume (7.9 nL); specific IPTG, AUR, and DMSO concentrations (10 μM, 5 μM, and 1% final, respectively); treatment times (17 h induction and 6 h analyte treatment); 2×YTP media during induction; 37° C. and 900 RPM incubation during induction; 1×DPBS media during analyte treatment; 37° C. and 900 RPM during treatment; a drop frequency of ~12 k-drops/second; a FSC gain of 0.5/1; a particle size of <25 μm; droplet pressure of 9 psi; a droplet frequency of 12 kHz; an amplitude of 30-50%; and a 3 drop sorting mode.

Next the inventors rigorously and carefully optimized the MRE assay, including optimizing multiple different parameters to increase the viability of the cells being selected for. As shown in FIG. 33B increased fluorescent activity is linked to reduced viability, see also FIGS. 28A-32. The inventors determined that in the cell-based MRE assay, bacterial cells comprising an active redox-enzyme to a target analyte have an increased oxidative stress level and/or increased ROS, which can lead to decreased viability. In essence, before optimization, the inventors determined that the assay selects for cells that are dying or have reduced viability due to high ROS. In order to decrease this cell death and increase the viability of the cells to be selected thus enabling for selection of cells comprising an active MRE, the inventors optimized multiple parameters, including but not limited to, bacterial cell species, FACs parameters, others.

To optimize the MRE assay, the inventors assessed analyte toxicity, presence of antioxidants, treatment media, FAC sorting modes and FACS chip nozzle width, anaerobic vs. aerobic incubation, post-sort media and post-sort temperature in order to optimize the MRE assay to increase viability of cells expressing a MRE specific to a target analyte (see FIG. 33B). Therefore, the optimized cell-based MRE assay described herein enables selection of cells expressing a MRE to the target analyte without a decreased cell viability.

The inventors discovered that certain bacterial strains were more resistant to cell death (FIG. 34A) with Origami2 and Shuffle and Rosetta-Gami cells being most resistant to fluorescence-induced cell death that expressed NicA2 and were contacted with nicotine. While the inventors discovered that incubating cells chilled (FIG. 34B) or in glutathione supplemented media (FIG. 34C) post-sorting had no effect on increasing viability, the inventors surprisingly discovered that incubating the cells in anaerobic condition significantly increased viability post-sort (FIG. 34D). Each parameter was carefully assessed (FIG. 35A-35B), and the inventors determined the optimal parameters include, but are not limited to a wider FACs sorting nozzle, anaerobic incubations, larger drop-sort volume, specific IPTG & AUR concentrations, and treatment times.

Accordingly, in some embodiments, the cell-based MRE assay is optimized where FACs sorting uses a nozzle width having a range of 100 μm-130 μm in diameter. In some embodiments, the cell-based MRE assay is optimized where the cells are incubated pre- and/or post-sorting, in anaerobic conditions. In some embodiments, the cell-based MRE assay is optimized where there is a larger drop-sort volume. In some embodiments, the cell-based MRE assay is optimized so that the gDNA fragment encoding a MRE protein is under the control of an inducible promoter, e.g., a promoter responsive to IPTG, where the IPTG concentration is 10 μM. In some embodiments, the cell-based MRE assay is optimized where the AUR concentration is 5 μM. In some embodiments, the cell-based MRE assay is optimized where the cells are contacted with IPTG for 17 h and AUR for 6 h. In some embodiments, the cell-based MRE assay is optimized where the AUR concentration is 5 μM. In some embodiments, the cell-based MRE assay is optimized where the cells are contacted with IPTG for 17 h and AUR for 6 h.

Figure 39:
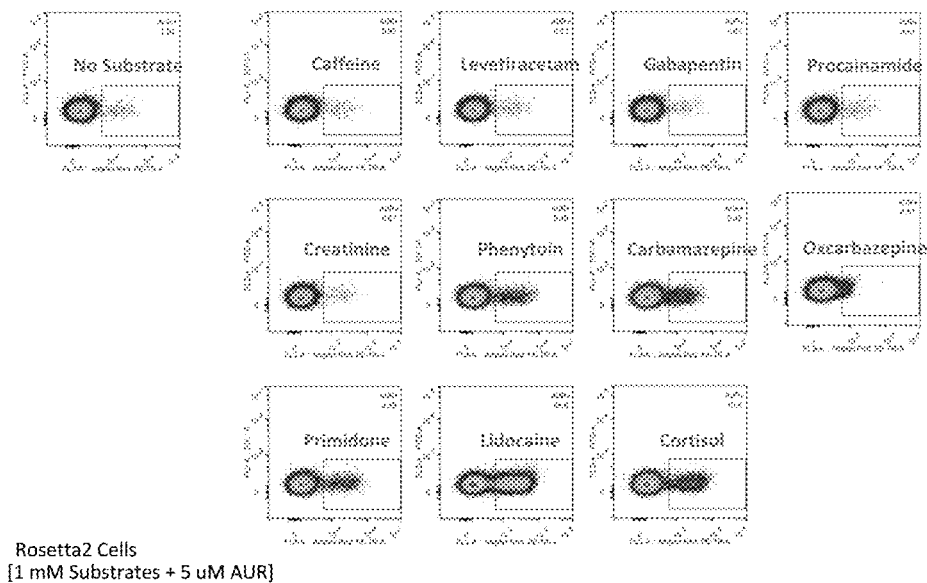
FIG. 39 shows using the optimized MRE assay in Rosetta2 (DE3) cells with a soil gDNA library, and assessing a range of target analytes including caffeine, levetracetam, gabapentin, procainamide, creatinine, phenytoin, carbamazepine, oxocarbazepine, primidone, lidocaine, or cortisol, showing a proportion of cells producing fluorescence. 1 mM of each substrate was assessed in the presence of 5 μM AUR.
Figure 40A:
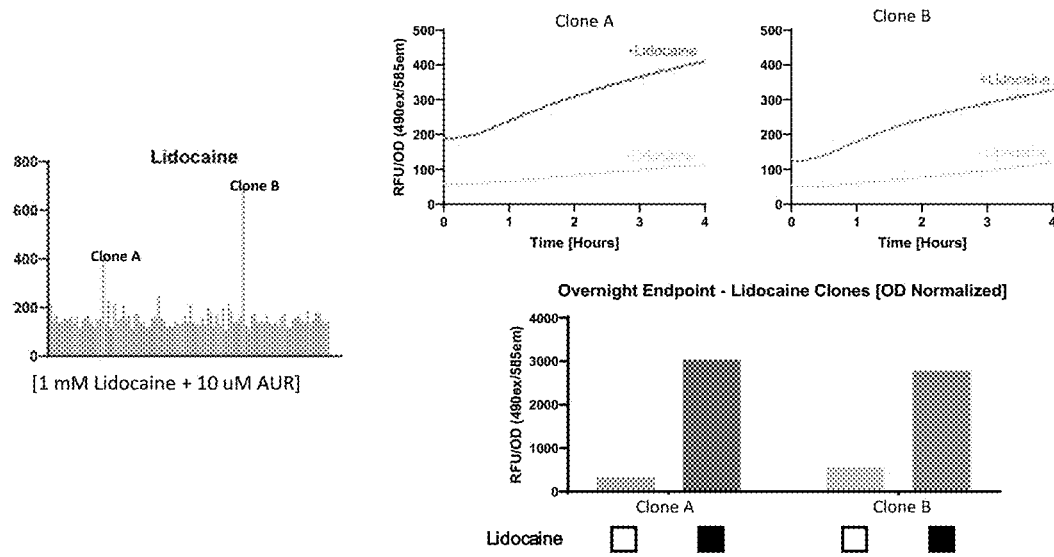
FIG. 40A-40B shows further characterization of colonies sorted from the assay performed in FIG. 39, using the optimized MRE assay in Rosetta2 (DE3) with a soil gDNA library.
Figure 40B:
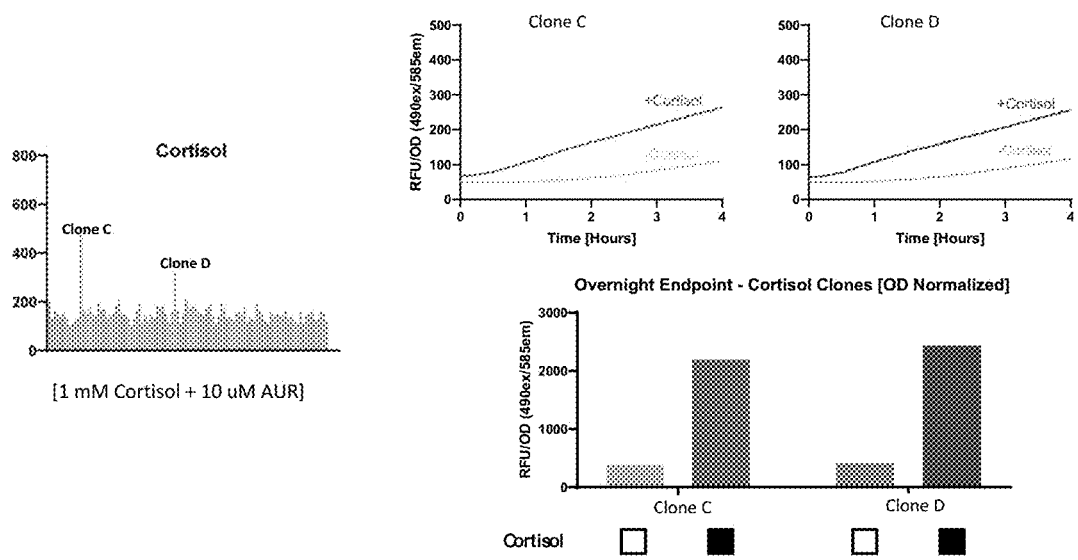

To demonstrate the optimized MRE assay is functional and can identify candidate oxidase MREs from an environmental gDNA source, the inventors screened a variety of analytes from a soil gDNA library (FIG. 39). Of each analyte assessed, there were several cells that exhibited fluorescence, indicating that the cell comprises a gDNA fragment expressing a candidate oxidase MRE that catalyes the target analyte (FIG. 39). Further analysis of the fluorescence cells identified two clones that expressed a candidate MRE responsive to lidocaine (FIG. 40A) and two clones that were responsive to cortisol (FIG. 40B). Additionally, the inventors also discovered one clone expressing a candidate MRE responsive to hydrocortisone (FIGS. 41A-41F). This demonstrates that the optimized cell-based MRE assay is sensitive to identify a candidate oxidase MRE to a number of target analytes.

Therefore, the inventors herein have described and optimized an assay and method for identification of oxidase MRE from microbes that can be used as a biorecognition element or transducing element in a biosensor, analogous to the glucose biosensor. Described herein is a platform for identifying oxidase MRE from environmental sources and microbes for use in biosensors for physiological monitoring. Using this system, the inventors have identified a number of oxidase MREs to a variety of analytes that can be useful in a biosensor, which can be used in an enzyme-based electrochemical nicotine biosensor.

Example 4

Figure 24:
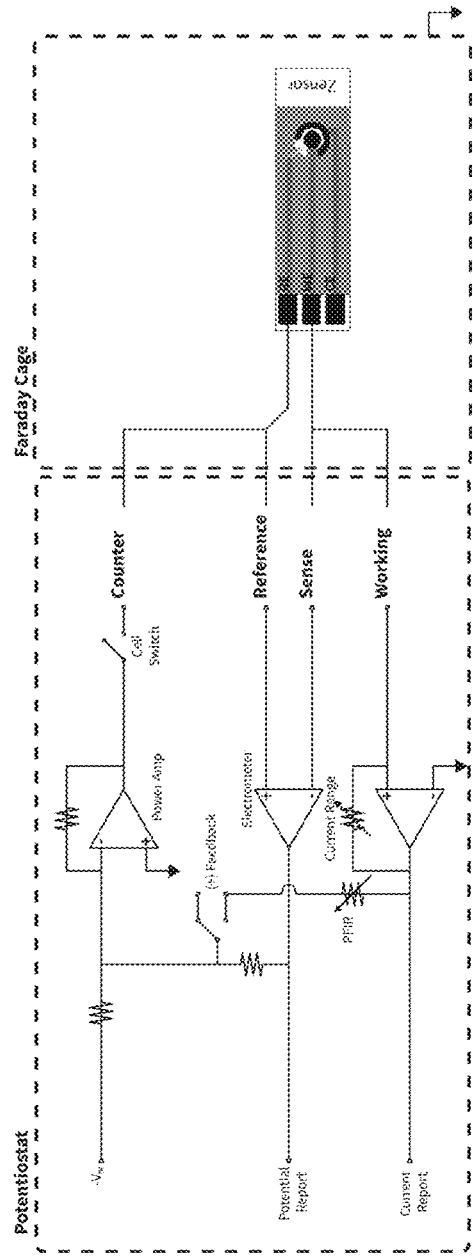
FIG. 24 shows a simplified representation of potentiostat circuitry connected to a screen-printed electrode (SPE) which allows for the accurate measurement of a current response resulting from analyte addition to the electrochemical biosensor in the presence of a redox enzyme.
Figure 25:
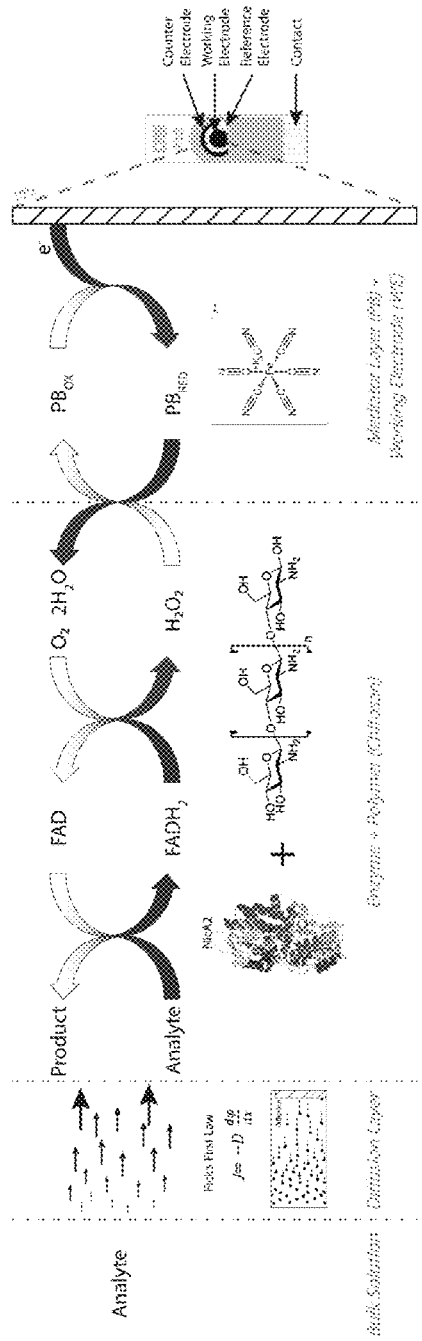
FIG. 25 shows a schematic of an electron flow mechanism. The nicotine biosensor is composed of a carbon three-electrode SPE with a Prussian Blue electrochemical mediator and a Ag/AgCl reference electrode. NicA2 is deposited onto the SPE working electrode (WE) with chitosan, a natural polymer. When analyte is added onto the three electrodes of the SPE the circuit is completed between them, and a current response can be measured when a constant potential is applied by a potentiostat. The presence of analyte in the solution causes the creation of a diffusion layer and a gradient between regions of high and low analyte concentrations. This gradient creates flux governed by Fick's Law and drives the movement of analyte to the working electrode.
Figure 26A:
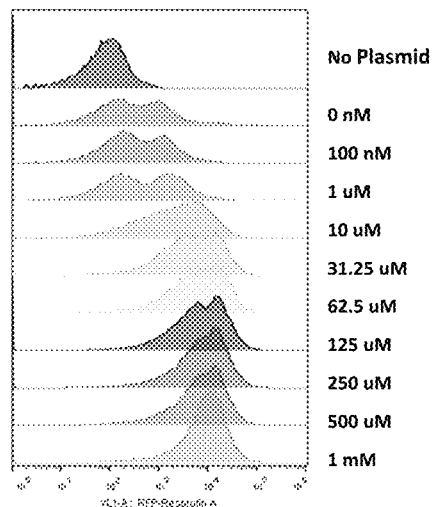
FIG. 26A-26B show that APEX2 peroxidase expressed in *E. Coli* cells can be used to detect ultra low µM exogenous $H_2O_2$.
Figure 26B:
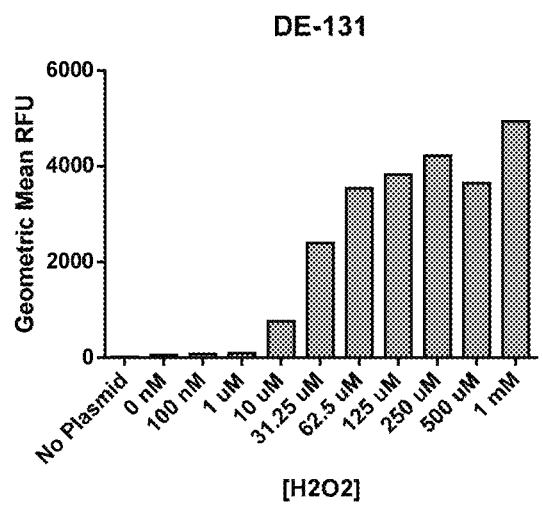
Figure 27A:
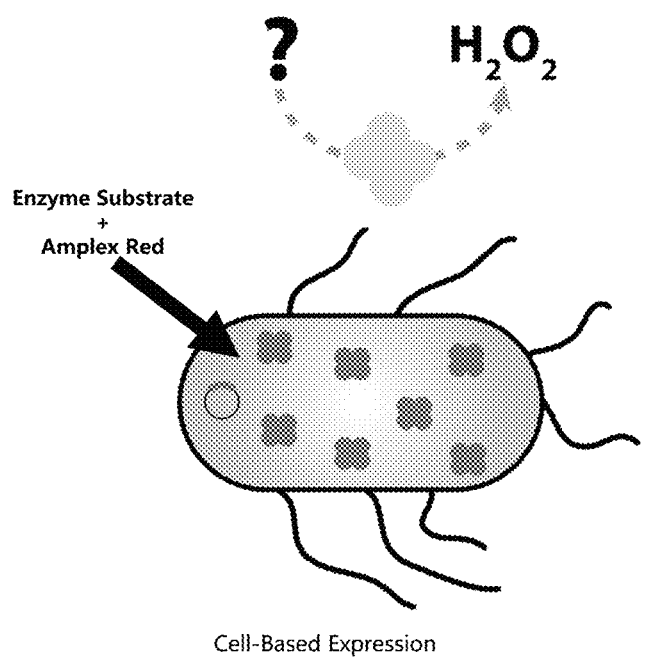
FIG. 27A-27B are schematics of exemplary MRE assays in a cell-based and cell-free system, respectively.
Figure 27B:
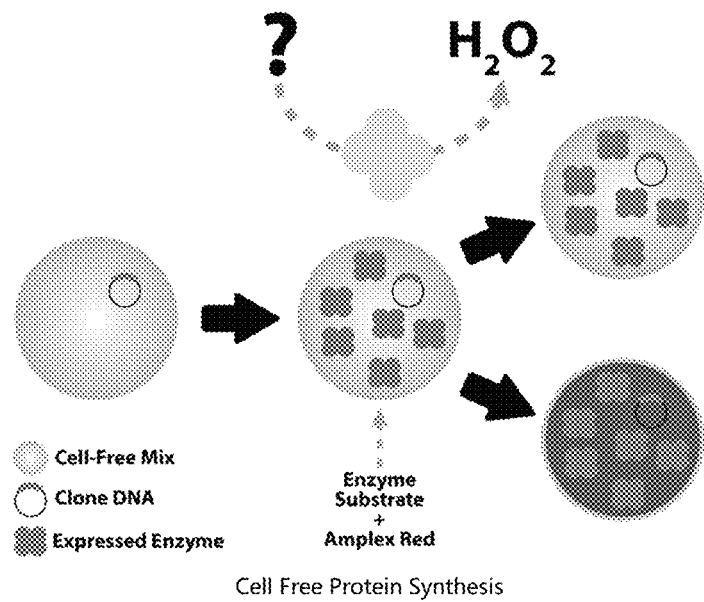
Figure 28A:
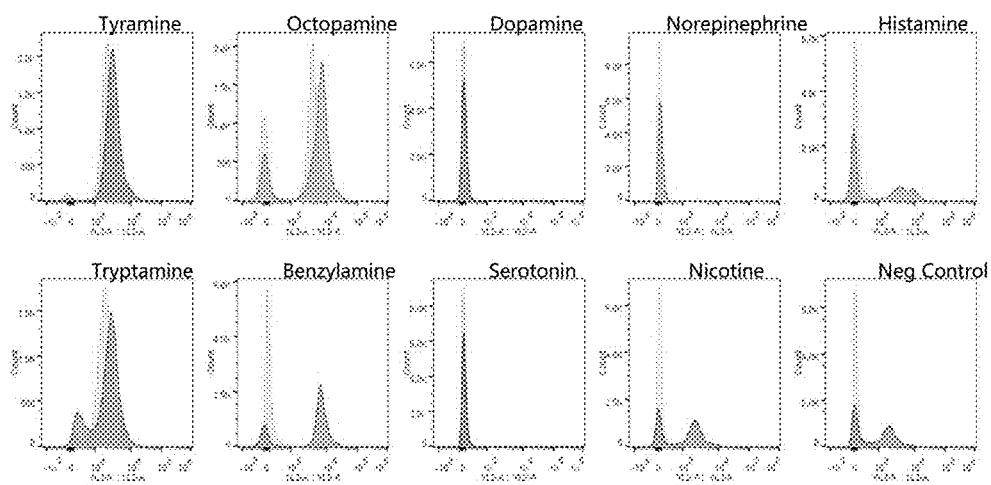
FIG. 28A-28B shows that the Amplex™ UltraRed (AUR) fluorescence assay can be used in live *E. coli* cells expressing the *C. ammoniagenes* MAO MRE.
Figure 28B:
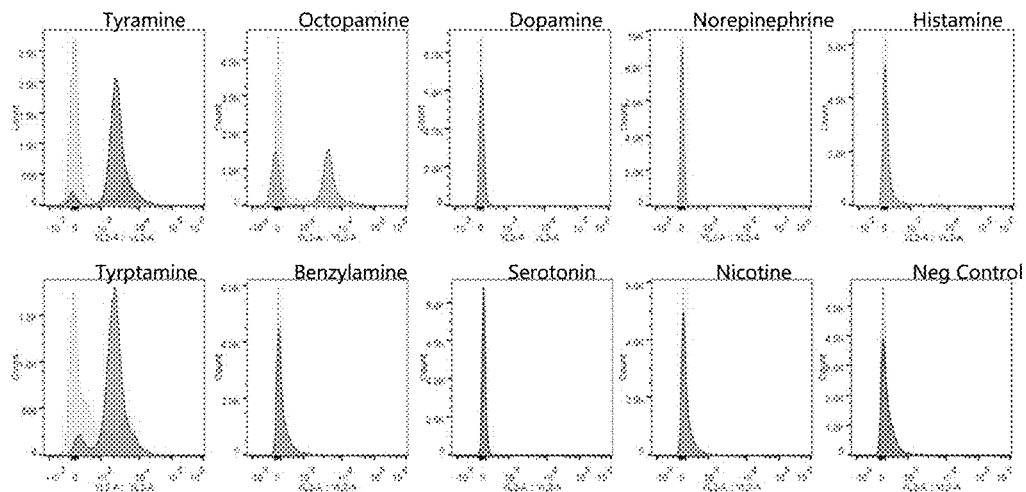
Figure 31A:
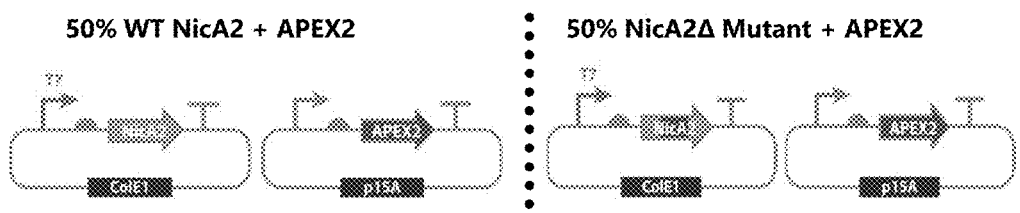
FIG. 31A-31C shows viability of Rosetta2 (DE3) and C41 cells from different FACS sorted gates expressing a 50/50% mixture of nicA2 and apex2 and nicA2Δ mutant and apex2.
Figure 31B:
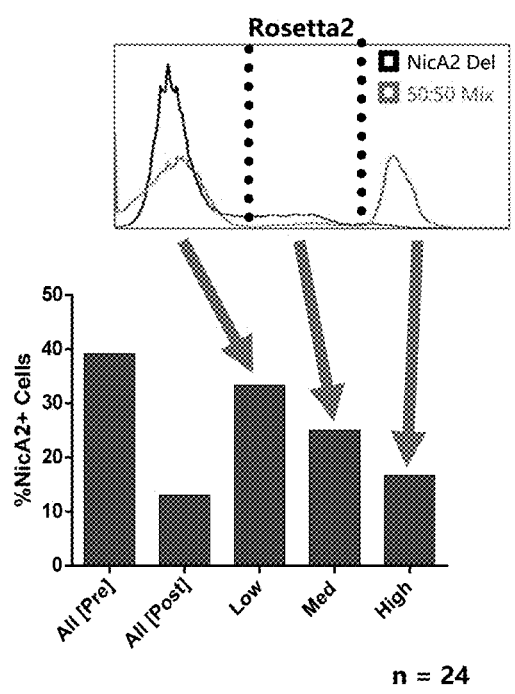
Figure 31C:
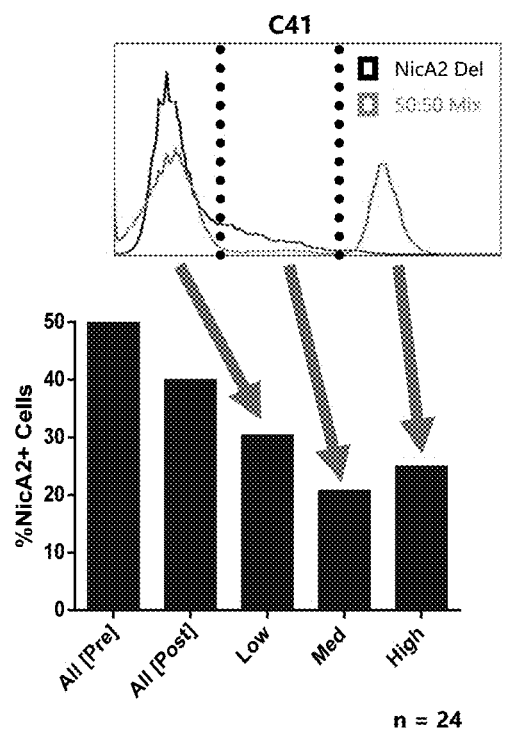
Figure 32:
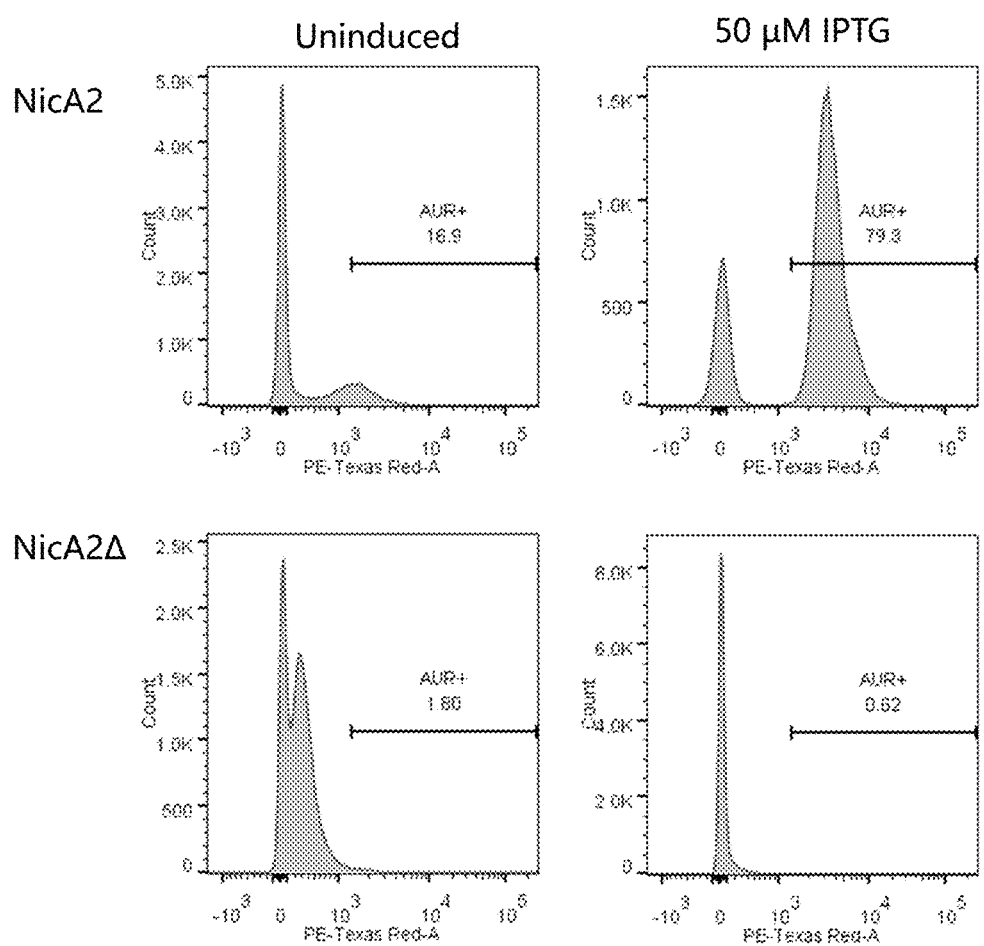
FIG. 32 shows induction of nicA2 with 50 μM IPTG shifts the percentage of cells fluorescent from 16.9% when uninduced to 79.3% when induced. Induction does not shift cells into the fluorescent state when nicA2 is mutated (nicA2Δ) confirming the fluorescence shift is due to the expression of nicA2 and nicA2 alone in the presence of APEX2, AUR, and nicotine.

Identified MREs Used as a Biorecognition Element in an Electrochemical Biosensor The use of NicA2 for use in an electrochemical biosensor was assessed, with a biosensor assembled and connected to a potentiostat (see e.g., FIG. 24-25). The electrochemical biosensor was composed of a Screen-Printed Prussian Blue/Carbon Electrode with a Ag/AgCl reference electrode (RE). To immobilize NicA2 onto the SPE working electrode (WE) chitosan polymer was used. Chronoamperometric responses were recorded over time with a potential –0.2 V versus the RE.

Figure 22A:
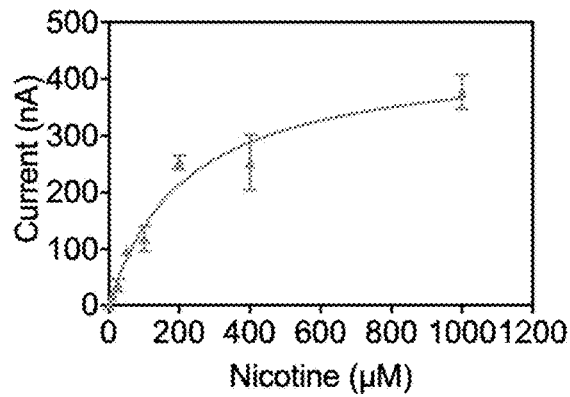
FIG. 22A-22D is a series of graphs showing that the nicotine biosensor is sensitive and accurate in PBS.
Figure 22B:
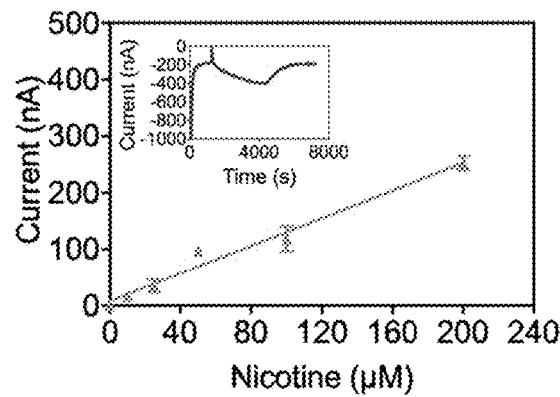

To quantify the current response, chronoamperometric experiments were performed whereby various concentrations of nicotine in PBS (0-1000 μM) were added to the biosensor with 2 nmol NicA2 (see e.g., FIG. 22A). A calibration curve of current to nicotine concentrations was produced from a range of 0-200 μM (see e.g., FIG. 22B) and the coefficient of determination, R2, was found to be 0.9768. A chronoamperometric assay with 200 μM nicotine is shown (see e.g., FIG. 22B inset). Maximal current (~250 nA) was reached after 4000 seconds with a return to baseline after 6000 seconds. The level of nicotine in active smokers' urine (see e.g., Table 3 above) falls into this range.

Figure 22C:
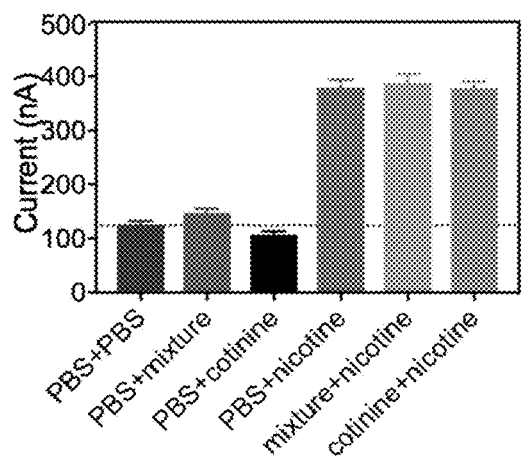
Figure 22D:
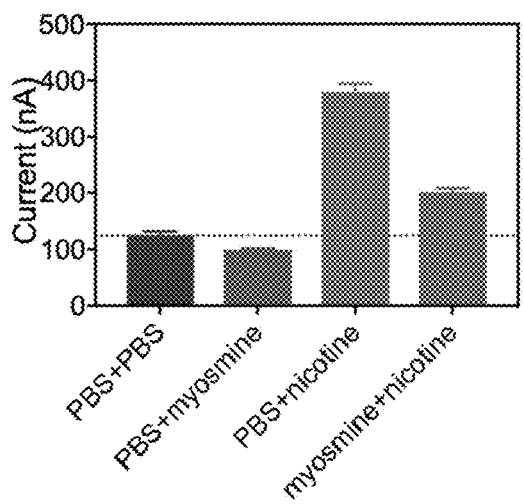
Figure 23:
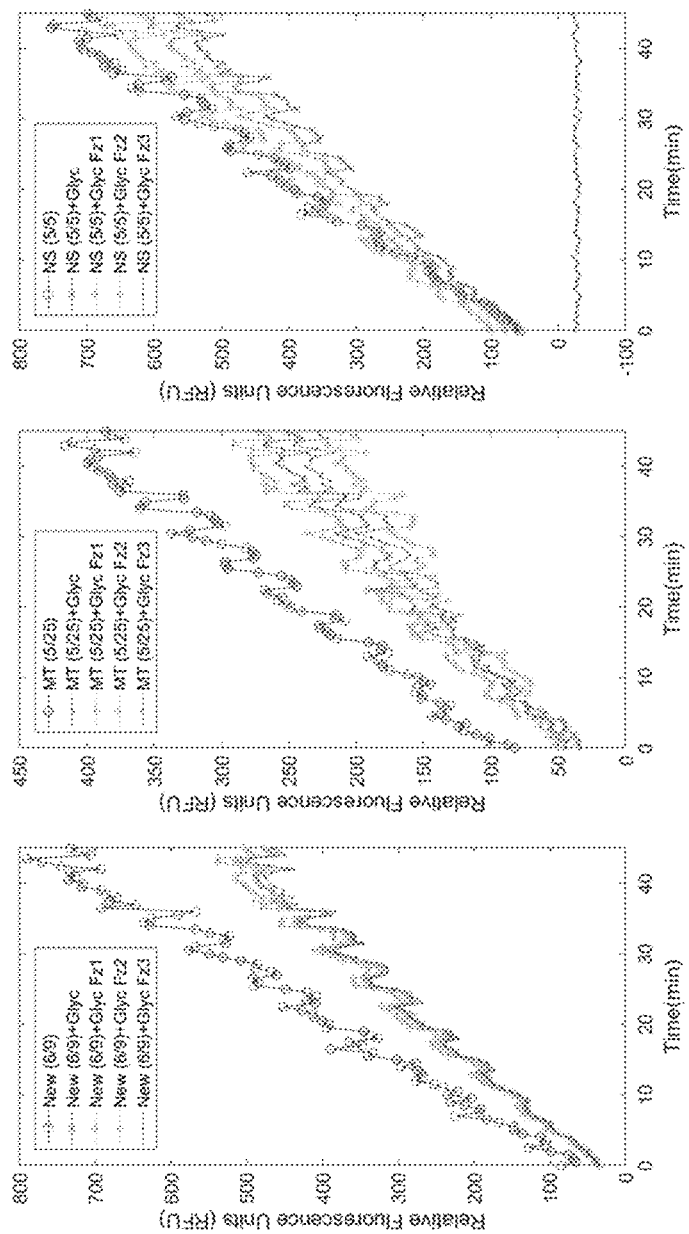
FIG. 23 is a series of graphs showing that NicA2 is resistant up to ~90% efficiency after 3 freeze/thaw cycles.

The selectivity of the biosensor was evaluated by measuring the chronoamperometric response in the presence of common interferents at relevant physiological concentrations in sweat (see e.g., FIG. 22C). These co-existing compounds had a minimal effect upon the response to nicotine. Similar experiments were performed to evaluate the selectivity of the sensor to cotinine Cotinine, the primary metabolite of nicotine in the human body, had a minimal effect upon the nicotine response (see e.g., FIG. 22C). Finally, to evaluate NicA2 dependence of the nicotine sensor's mechanism of action, myosmine, an inhibitor of NicA2, was added in the middle of a chronoamperometric experiment (see e.g., FIG. 22D). Minimal responses were observed from myosmine alone (red bar) or nicotine addition after NicA2 was inhibited by myosmine (purple bar).

The inventors have developed a system and platform for identifying enzymatic sensor parts for virtually an unlimited number of analytes. Furthermore, the sensor can be brought to a closed-loop continuous measurement system similar to the glucose biosensor. This approach thus allows capitalization on the enormous and untapped reservoir of microbes to identify biosensing elements for any analyte of interest including, but not limited to, hormones, pharmaceutical agents, pesticides, toxins, neurotransmitters, immunomodulators, metabolites, and carcinogens.

Example 5

Current physiological sensors on the market such as the Fitbit™ and Apple Watch™ are limited to the detection of pH, hydration, temperature, heart rate, UX index, oxygen, sleep health, and energy expenditure with limited accuracy and reproducibility. Presently, the single best example of a commercially successful enzymatic biosensor is the glucose biosensor which has existed for approximately 50 years and has in the past two decades evolved into the continuous glucose monitor (CGM; see e.g., Olczuk et al. Diabetes Metab Syndr 2018, 12 (2), 181-187). By 2004, the glucose biosensor was responsible for about 85% of the world market for biosensors, estimated to be $5 billion USD at the time. By 2015, the market for glucose biosensors was valued at $15.3 billion USD and is expected to surpass $31 billion USD by 2024 per Hexa Research. The glucose monitor's functionality is based on the isolation and use of a glucose oxidase (GOx) enzyme from Aspergillus niger, a fungus. Specifically, the ability of $GO_X$ to produce $H_2O_2$ from β-D-glucose and oxygen has been used to engineer the first glucose biosensor in an electrochemical fashion. With a mediator and a three-electrode system, $H_2O_2$ generated from $GO_X$ in response to β-D-glucose, along with a constant electrical potential, produces current which can be used as a readout for the amount of β-D-glucose present in solution.

Even with the immense commercial success of the glucose biosensor, comparable enzymatic biosensors have been limited. By 2007, commercially available enzyme based clinical tests could detect only glucose, lactate, choline, urea, uric acid, lysine, and oxygen. By 2008, amperometric based biosensors solely included those for glucose ($GO_X$), fructose (FDH), lactate ($LO_X$), glutamate ($LGO_X$), lysine (LDH), ethanol (ADH), and morphine (MDH) (see e.g., Dzyadevych et al. Irbm 2008, 29 (2-3), 171-180). The reason for the lack of a wide variety of biosensors is primarily due to two reasons. Of the seven biosensors listed, few have daily physiological relevance. The exception is the glucose biosensor due to diabetes affecting 382 million people and being the $8^{th}$ leading cause of death worldwide by 2013 which naturally created a large market and need for such a sensor. The second reason is that the current largest scientific vendors, such as Sigma-Aldrich™, have a limited inventory of enzymes such as $GO_X$, $LO_X$, FDH, $LGO_X$, and ADH with little intention of investing resources to provide new electrochemically relevant ones.

In response to the lack of electrochemical biosensors, the inventors have mined an unexplored reservoir of biorecognition elements in bacteria. Bacteria have evolved over 3 billion years to detect and respond to virtually all classes of stimuli relevant to human physiology, and thus contain molecular sensing enzymes of interest. Using a combination of whole transcriptome RNA sequencing (RNA-Seq) and a functional screen (Amplex™ UltraRed assay) the inventors have identified and isolated a number of biosensing oxidase enzymes, including NicA2. The redox enzymes identified using the methods and assays disclosed herein can be used in biosensors, and the development of small, easy to use, and cheap electrochemical biosensors, which started from bacterial cultures for physiologically relevant analytes. These biosensors are typically composed of a screen-printed electrode (SPE), electron mediator (e.g. Prussian Blue), and a redox enzyme. This pipeline was used to build an enzyme-based electrochemical nicotine biosensor.

Out of all current preventable deaths nicotine is the leading cause. Approximately 6 million mortalities can be accounted for by nicotine use per year globally. Tobacco-related deaths cost the United States approximately $300 billion USD each year. Furthermore, nicotine is singularly responsible for the dependence-forming properties of tobacco smoking. Although most smokers are aware of the detrimental health consequences of smoking, the addictive properties of nicotine make it difficult to abstain in short periods of time or immediately. At the moment, leading pharmacological aids for quitting, which include the anti-depressant drug bupropion and varenicline, show only a 15-30% abstinence rate after 1 year of treatment. Therefore, breaking nicotine addiction is challenging and relapse rates remain high. The extremely rapid timescale of nicotine action renders existing techniques for monitoring of nicotine levels ill-suited (see e.g., Benowitz et al. NIDA Res Monogr 1990, 99, 12-29). An alternative to pharmacological aids and their side effects is self-disciplined termination through the advent of a device which continuously measures internal nicotine levels. Such a biosensor offers smokers the ability to ease their dependency on nicotine addiction by incremental cessation. Another possibility is for a nicotine biosensor to monitor and regulate the amount of nicotine being administered to a patient, in concordance with a physician, or act as an acute-dosing product in times of particularly strong cravings (see e.g., Wadgave and Nagesh, L., Nicotine replacement therapy: An overview. International journal of health sciences 2016, 10 (3), 425).

Existing biosensor designs outside of electrochemical ones have noticeable limitations. The most common design utilizes a biorecognition element coupled to a physicochemical transduction mechanism (see e.g., Turner, A., Trends in Biotechnology 2013, 31 (3), 119-120; Mary et al., Measurement Science and Technology 2014, 25 (3), 032001; Evtugyn, G., Biosensors: Essentials. Springer: 2014; Vol. 84). The gold standard for clinical relevant analytes use antibodies as this biorecognition element. However, antibodies suffer from several important shortcomings: 1) Traditionally, antibody production requires animal immunization followed by monoclonal isolation and is expensive, highly variable, time consuming, and challenging with small molecule analytes (see e.g., Mary et al. 2014, supra). More recent recombinant techniques simplify this process and improve reproducibility, but the process remains expensive due to the use of mammalian cell lines or heterologous hosts (see e.g., Frenzel, et al. Frontiers in immunology 2013, 4, 217; Hornsby et al. Molecular & cellular proteomics: MCP 2015, 14 (10), 2833-47). 2) Binding of the analyte to the antibody leads to only a small physicochemical change, requiring the use of a secondary assay to detect the binding event (see e.g., Mary et al. 2014, supra; az-Gonzale et al. Electroanalysis 2005, 17 (21)). Enzyme-linked immunosorbent assays (ELISAs) are the most common transduction approach and are multistep, labor-intensive, time-consuming, and not well-suited for integration into wearable technology (see e.g., az-Gonzale et al. 2005, supra). More recently, aptamers have been studied as an alternative to antibodies, but also lack an intrinsic transduction mechanism (see e.g., Mary et al. 2014, supra; Marrazza, G., Aptamer Sensors. Biosensors (Basel) 2017, 7 (1)). Due to these limitations, non-electrochemical biosensors often are suboptimal design choices for physiological monitoring.

Numerous non-enzymatic nicotine sensors have been reported in literature. These include electrochemical biosensors which function by electropolymerization of o-aminophenol (see e.g., Wu et al. Frontiers of Chemistry in China 2006, 1 (2), 183-187), alumina-coated silica nanocomposites (see e.g., Wang et al. Electrochemistry Communications 2009, 11 (4), 733-735), pyrolytic graphite (see e.g., Sims et al. Sensors and Actuators B: Chemical 2010, 144 (1), 153-158), cerium nanoparticles (see e.g., Fekry et al. RSC Advances 2015, 5 (64), 51662-51671), carbon nanotubes (see e.g., Goodarzi et al. Journal of Nanostructure in Chemistry 2015, 5 (3), 237-242), carboxylated graphene (see e.g., Xiao et al. Analytical Methods 2015, 7 (3), 1147-1153), polydopamine functionalized nanoparticles (see e.g., Jing et al. Sci Rep 2016, 6, 29230), and nitrogen-doped graphene sheets (see e.g., Li et al. J. Electroanal. Chem. 2017, 784, 77-84). The lowest limit of detection was reported by the polydopamine functionalized nanoparticles at 15 nM and a detection range of 0.05-500 µM (see e.g., Jing et al 2016, supra), and it is the only nicotine sensor thus far to prove unresponsiveness to cotinine, the primary metabolite of nicotine in the human body. Furthermore, the same biosensor was reported to have 92.8% activity after storage at 4° C. for four weeks (see e.g., Jing et al 2016, supra). Although the reported biosensors have demonstrated sensitivity and stability, they require optimization and designing de novo for the particular analyte of interest. In contrast, evolution of bacterial enzymes for the recognition and metabolism of a multitude of physiologically relevant analytes has already been performed by nature. A pipeline to identify them in a timely fashion has not been described. Once identified, if the enzymes are not selective, sensitive, fast, or stable as desired, directed evolution, can be used to improve them (see e.g., Lutz, S.; Iamurri, S. M., Protein Engineering: Past, Present, and Future. In Protein Engineering, Springer: 2018; pp 1-12).

REFERENCES

All references and publication cited in the specification and Examples are incorporated herein in their entirety by reference.
1. Organization, W. H., WHO report on the global tobacco epidemic 2017: Monitoring tobacco use and prevention policies. 2017.
2. Xu, X.; Bishop, E. E.; Kennedy, S. M.; Simpson, S. A.; Pechacek, T. F., Annual healthcare spending attributable to cigarette smoking: an update. Am J Prev Med 2015, 48 (3), 326-33.
3. McGinnis, J. M.; Foege, W. H., Actual causes of death in the United States. *Jama* 1993, 270 (18), 2207-2212.
4. Rice, V. H.; Stead, L. F., Nursing interventions for smoking cessation. *Cochrane Database Syst Rev* 2008,1.
5. Benowitz, N. L., Clinical pharmacology of inhaled drugs of abuse: implications in understanding nicotine dependence. *NIDA Res Monogr* 1990, 99, 12-29.
6. Wadgave, U.; Nagesh, L., Nicotine replacement therapy: An overview. *International journal of health sciences* 2016, 10 (3), 425.
7. Tang, H.; Wang, L.; Wang, W.; Yu, H.; Zhang, K.; Yao, Y.; Xu, P., Systematic unraveling of the unsolved pathway of nicotine degradation in Pseudomonas. *PLoS Genet* 2013, 9 (10), e1003923.
8. Xue, S.; Schlosburg, J. E.; Janda, K. D., A New Strategy for Smoking Cessation: Characterization of a Bacterial Enzyme for the Degradation of Nicotine. *J Am Chem Soc* 2015, 137 (32), 10136-9.
9. Benowitz, N. L., Cotinine as a biomarker of environmental tobacco smoke exposure. *Epidemiologic reviews* 1996, 18 (2), 188-204.
10. Campanella, L.; Favero, G.; Tomassetti, M., Direct determination of nicotine in antismoking pharmaceutical products and in tobacco using an inhibition biosensor. *Anal. Lett.* 2001, 34 (6), 855-866.
11. Yang, Y. H.; Yang, M. H.; Wang, H.; Tang, L.; Shen, G. L.; Yu, R. Q., Inhibition biosensor for determination of nicotine. *Anal. Chim. Acta* 2004, 509 (2), 151-157.
12. Mitsubayashi, K.; Nakayama, K.; Taniguchi, M.; Saito, H.; Otsuka, K.; Kudo, H., Bioelectronic sniffer for nicotine using enzyme inhibition. *Anal. Chim. Acta* 2006, 573, 69-74.
13. Tan, Y. G.; Yin, J.; Liang, C. D.; Peng, H.; Nie, L. H.; Yao, S. Z., A study of a new TSM biomimetic sensor using a molecularly imprinted polymer coating and its application for the determination of nicotine in human serum and urine. *Bioelectrochemistry* 2001, 53 (2), 141-148.
14. Croux, D.; Weustenraed, A.; Pobedinskas, P.; Horemans, F.; Dilien, H.; Haenen, K.; Cleij, T.; Wagner, P.; Thoelen, R.; De Ceuninck, W., Development of multichannel quartz crystal microbalances for MIP-based biosensing. *Phys. Status Solidi A-Appl. Mat.* 2012, 209 (5), 892-899.
15. Alenus, J.; Galar, P.; Ethirajan, A.; Horemans, F.; Weustenraed, A.; Cleij, T. J.; Wagner, P., Detection of L-nicotine with dissipation mode quartz crystal microbalance using molecular imprinted polymers. *Phys. Status Solidi A-Appl. Mat.* 2012, 209 (5), 905-910.
16. Alenus, J.; Ethirajan, A.; Horemans, F.; Weustenraed, A.; Csipai, P.; Gruber, J.; Peeters, M.; Cleij, T. J.; Wagner, P., Molecularly imprinted polymers as synthetic receptors for the QCM-D-based detection of L-nicotine in diluted saliva and urine samples. Anal. Bioanal. Chem. 2013, 405 (20), 6479-6487.
17. Cennamo, N.; D'Agostino, G.; Pesavento, M.; Zeni, L., High selectivity and sensitivity sensor based on MIP and SPR in tapered plastic optical fibers for the detection of L-nicotine. *Sens. Actuator B-Chem.* 2014, 191, 529-536.
18. Kamra, T.; Zhou, T. C.; Montelius, L.; Schnadt, J.; Ye, L., Implementation of Molecularly Imprinted Polymer Beads for Surface Enhanced Raman Detection. *Anal. Chem.* 2015, 87 (10), 5056-5061.
19. Peeters, M.; Csipai, P.; Geerets, B.; Weustenraed, A.; van Grinsven, B.; Thoelen, R.; Gruber, J.; De Ceuninck, W.; Cleij, T. J.; Troost, F. J.; Wagner, P., Heat-transfer-based detection of L-nicotine, histamine, and serotonin using molecularly imprinted polymers as biomimetic receptors. Anal. Bioanal. Chem. 2013, 405 (20), 6453-6460. 20. Geerets, B.; Peeters, M.; van Grinsven, B.; Bers, K.; de Ceuninck, W.; Wagner, P., Optimizing the Thermal Read-Out Technique for MIP-Based Biomimetic Sensors: Towards Nanomolar Detection Limits. *Sensors* 2013, 13 (7), 9148-9159.
21. Wackers, G.; Vandenryt, T.; Cornelis, P.; Kellens, E.; Thoelen, R.; De Ceuninck, W.; Losada-Perez, P.; van Grinsven, B.; Peeters, M.; Wagner, P., Array Formatting of the Heat-Transfer Method (HTM) for the Detection of Small Organic Molecules by Molecularly Imprinted Polymers. *Sensors* 2014,14 (6), 11016-11030.
22. Wang, S. J.; Liaw, H. W.; Tsai, Y. C., Low potential detection of nicotine at multiwalled carbon nanotube-alumina-coated silica nanocomposite. *Electrochemistry Communications* 2009, 11 (4), 733-735.

23. Sims, M. J.; Rees, N. V.; Dickinson, E. J. F.; Compton, R. G., Effects of thin-layer diffusion in the electrochemical detection of nicotine on basal plane pyrolytic graphite (BPPG) electrodes modified with layers of multi-walled carbon nanotubes (MWCNT-BPPG). Sens. Actuator B-Chem. 2010, /44 (1), 153-158.

24. Lo, T. W. B.; Aldous, L.; Compton, R. G., The use of nano-carbon as an alternative to multi-walled carbon nanotubes in modified electrodes for adsorptive stripping voltammetry. Sens. Actuator B-Chem. 2012, 162 (1), 361-368.

25. Svorc, L.; Stankovic, D. M.; Kalcher, K., Boron-doped diamond electrochemical sensor for sensitive determination of nicotine in tobacco products and anti-smoking pharmaceuticals. Diam. Relat. Mat. 2014, 42, 1-7.

26. Jing, Y. Q.; Yuan, X. X.; Yuan, Q.; He, K. X.; Liu, Y. J.; Lu, P.; Li, H. Q.; Li, B.; Zhan, H.; Li, G. L., Determination of nicotine in tobacco products based on mussel-inspired reduced graphene oxide-supported gold nanoparticles. Sci Rep-Uk 2016, 6, 8.

27. Jing, Y. Q.; Lin, E. G.; Su, X. H.; Liu, Y. J.; Li, H. Q.; Yuan, X. X.; Ping, L.; Fan, Y. K., Electrodeposition of Au nanoparticles on poly(diallyldimethylammonium chloride) functionalized reduced graphene oxide sheets for voltammetric determination of nicotine in tobacco products and anti-smoking pharmaceuticals. RSC Adv. 2016, 6 (31), 26247-26253.

28. Li, X. Q.; Zhao, H. L.; Shi, L. B.; Zhu, X.; Lan, M. B.; Zhang, Q.; Fan, Z. H., Electrochemical sensing of nicotine using screen-printed carbon electrodes modified with nitrogen-doped graphene sheets. J. Electroanal. Chem. 2017, 784, 77-84.

29. Wang, R.; Blackburn, G.; Desai, M.; Phelan, D.; Gillinov, L.; Houghtaling, P.; Gillinov, M., Accuracy of wrist-worn heart rate monitors. Jama cardiology 2017, 2 (1), 104-106.

30. Wallen, M. P.; Gomersall, S. R.; Keating, S. E.; Wisloff, U.; Coombes, J. S., Accuracy of heart rate watches: implications for weight management. PLoS One 2016, 11 (5), e0154420.

31. Sanders, J. P.; Loveday, A.; Pearson, N.; Edwardson, C.; Yates, T.; Biddle, S. J.; Esliger, D. W., Devices for self-monitoring sedentary time or physical activity: a scoping review. Journal of medical Internet research 2016, 18 (5).

32. Harrison, D.; Marshall, P.; Bianchi-Berthouze, N.; Bird, J. In Activity tracking: barriers, workarounds and customisation, Proceedings of the 2015 ACM International Joint Conference on Pervasive and Ubiquitous Computing, ACM: 2015; pp 617-621.

33. El-Amrawy, F.; Nounou, M. I., Are currently available wearable devices for activity tracking and heart rate monitoring accurate, precise, and medically beneficial? Healthcare informatics research 2015, 21 (4), 315-320.

34. Ko, P.-R. T.; Kientz, J. A.; Choe, E. K.; Kay, M.; Landis, C. A.; Watson, N. F., Consumer sleep technologies: a review of the landscape. Journal of clinical sleep medicine: JCSM: official publication of the American Academy of Sleep Medicine 2015, 11 (12), 1455.

35. Olczuk, D.; Priefer, R., A history of continuous glucose monitors (CGMs) in self-monitoring of diabetes mellitus. Diabetes Metab Syndr 2018, 12 (2), 181-187.

36. Newman, J.; Tigwell, L.; Turner, A.; Warner, P., Biosensors: a clearer view. Biosensors 2004.

37. Turner, A., Biosensors: then and now. Trends in Biotechnology 2013, 31 (3), 119-120.

38. Dzyadevych, S. V.; Arkhypova, V. N.; Soldatkin, A. P.; El'skaya, A. V.; Martelet, C.; Jaffrezic-Renault, N., Amperometric enzyme biosensors: Past, present and future. Irbm 2008, 29 (2-3), 171-180.

39. Tao, Z.; Shi, A.; Zhao, J., Epidemiological Perspectives of Diabetes. Cell Biochem Biophys 2015, 73 (1), 181-5.

40. Mary, A. A.; Aleksandr, S., Novel trends in affinity biosensors: current challenges and perspectives. Measurement Science and Technology 2014, 25 (3), 032001.

41. Evtugyn, G., Biosensors: Essentials. Springer: 2014; Vol. 84.

42. Frenzel, A.; Hust, M.; Schiiiniann, T., Expression of recombinant antibodies. Frontiers in immunology 2013, 4, 217.

43. Hornsby, M.; Paduch, M.; Miersch, S.; Saaf, A.; Matsuguchi, T.; Lee, B.; Wypisniak, K.; Doak, A.; King, D.; Usatyuk, S.; Perry, K.; Lu, V.; Thomas, W.; Luke, J.; Goodman, J.; Hoey, R. J.; Lai, D.; Griffin, C.; Li, Z.; Vizeacoumar, F. J.; Dong, D.; Campbell, E.; Anderson, S.; Zhong, N.; Graslund, S.; Koide, S.; Moffat, J.; Sidhu, S.; Kossiakoff, A.; Wells, J., A High Through-put Platform for Recombinant Antibodies to Folded Proteins. Molecular & cellular proteomics: MCP 2015, 14 (10), 2833-47.

44. az-Gonzalez, M. i. D.; a, M. a. B. G.-G.; ia, A. n. C.-G., Recent Advances in Electrochemical Enzyme Immunoassays. Electroanalysis 2005, 17 (21).

45. Marrazza, G., Aptamer Sensors. Biosensors (Basel) 2017, 7 (1).

46. Wu, Z.; Zhang, X.; Yang, Y.; Shen, G.; Yu, R., A sensitive nicotine sensor based on molecularly imprinted electropolymer of o-aminophenol. Frontiers of Chemistry in China 2006, 1 (2), 183-187.

47. Wang, S.-J.; Liaw, H.-W.; Tsai, Y.-C., Low potential detection of nicotine at multiwalled carbon nanotube-alumina-coated silica nanocomposite. Electrochemistry Communications 2009, 11 (4), 733-735.

48. Sims, M. J.; Rees, N. V.; Dickinson, E. J.; Compton, R. G., Effects of thin-layer diffusion in the electrochemical detection of nicotine on basal plane pyrolytic graphite (BPPG) electrodes modified with layers of multi-walled carbon nanotubes (MWCNT-BPPG). Sensors and Actuators B: Chemical 2010, 144 (1), 153-158.

49. Fekry, A.; Azab, S.; Shehata, M.; Ameer, M., A novel electrochemical nicotine sensor based on cerium nanoparticles with anionic surfactant. RSC Advances 2015, 5 (64), 51662-51671.

50. Goodarzi, Z.; Maghrebi, M.; Zavareh, A. F.; Mokhtari-Hosseini, Z. B.; Ebrahimi-Hoseinzadeh, B.; Zarmi, A. H.; Barshan-Tashnizi, M., Evaluation of nicotine sensor based on copper nanoparticles and carbon nanotubes. Journal of Nanostructure in Chemistry 2015, 5 (3), 237-242.

51. Xiao, H.; Sun, L.; Yan, H.; Wang, W.; Liu, J.; Yan, Q.; Chao, L.; Chen, C.; Xie, Q.; Wen, J., Electroanalysis of nicotine at an electroreduced carboxylated graphene modified glassy carbon electrode. Analytical Methods 2015, 7 (3), 1147-1153.

52. Jing, Y.; Yuan, X.; Yuan, Q.; He, K.; Liu, Y.; Lu, P.; Li, H.; Li, B.; Zhan, H.; Li, G., Determination of nicotine in tobacco products based on mussel-inspired reduced graphene oxide-supported gold nanoparticles. Sci Rep 2016, 6, 29230.

53. Lutz, S.; Iamurri, S. M., Protein Engineering: Past, Present, and Future. In Protein Engineering, Springer: 2018; pp 1-12.

54. Liu, J.; Ma, G.; Chen, T.; Hou, Y.; Yang, S.; Zhang, K.-Q.; Yang, J., Nicotine-degrading microorganisms and their potential applications. *Applied microbiology and biotechnology* 2015, 99 (9), 3775-3785.

55. Yu, H.; Tang, H.; Wang, L.; Yao, Y.; Wu, G.; Xu, P., Complete genome sequence of the nicotine-degrading *Pseudomonas putida* strain S16. *J Bacteriol* 2011, 193 (19), 5541-2.

56. Tang, H.; Wang, S.; Ma, L.; Meng, X.; Deng, Z.; Zhang, D.; Ma, C.; Xu, P., A novel gene, encoding 6-hydroxy-3-succinoylpyridine hydroxylase, involved in nicotine degradation by *Pseudomonas putida* strain S16. *Appl Environ Microbiol* 2008, 74 (5), 1567-74.

57. Tang, H.; Wang, L.; Meng, X.; Ma, L.; Wang, S.; He, X.; Wu, G.; Xu, P., Novel nicotine oxidoreductase-encoding gene involved in nicotine degradation by *Pseudomonas putida* strain S16. *Appl Environ Microbiol* 2009, 75 (3), 772-8.

58. Tang, H.; Yao, Y.; Wang, L.; Yu, H.; Ren, Y.; Wu, G.; Xu, P., Genomic analysis of *Pseudomonas putida*: genes in a genome island are crucial for nicotine degradation. *Sci Rep* 2012, 2, 377.

59. Tararina, M. A.; Janda, K. D.; Allen, K. N., Structural Analysis Provides Mechanistic Insight into Nicotine Oxidoreductase from *Pseudomonas putida*. *Biochemistry* 2016, 55 (48), 6595-6598.

60. Russell, M. A.; Jarvis, M.; Iyer, R.; Feyerabend, C., Relation of nicotine yield of cigarettes to blood nicotine concentrations in smokers. *Br Med J* 1980, 280 (6219), 972-6.

61. Moyer, T. P.; Charlson, J. R.; Enger, R. J.; Dale, L. C.; Ebbert, J. O.; Schroeder, D. R.; Hurt, R. D., Simultaneous analysis of nicotine, nicotine metabolites, and tobacco alkaloids in serum or urine by tandem mass spectrometry, with clinically relevant metabolic profiles. *Clin Chem* 2002, 48 (9), 1460-71.

62. Lindell, G.; Lunell, E.; Graffner, H., Transdermally administered nicotine accumulates in gastric juice. *Eur J Clin Pharmacol* 1996, 51 (3-4), 315-8.

63. Henningfield, J. E.; London, E.; Pogun, S., *Nicotine psychopharmacology*. Springer Science & Business Media: 2009; Vol. 192.

64. Etter, J. F.; Vu Duc, T.; Perneger, T. V., Saliva cotinine levels in smokers and nonsmokers. *Am J Epidemiol* 2000, 151 (3), 251-8.

65. Balabanova, S.; Buhler, G.; Schneider, E.; Boschek, H. J.; Schneitler, H., [Nicotine excretion by the apocrine and eccrine sweat in smokers and passive smokers]. *Hautarzt* 1992, 43 (2), 73-6.

66. Tararina et al., Crystallography Coupled with Kinetic Analysis Provide Mechanistic Underpinnings of a Nicotine-Degrading Enzyme. Biochemistry. 2018 Jul. 3; 57(26): 3741-3751.

67. Xue et al., An Enzymatic Advance in Nicotine Cessation Therapy, Chem Commun (Camb). 2018 Feb. 13; 54(14): 1686-1689.

OTHER REFERENCES

All references and publication cited in the specification and Examples are incorporated herein in their entirety by reference.

1. Popovic, A., et al., Activity screening of environmental metagenomic libraries reveals novel carboxylesterase families. Sci Rep, 2017. 7: p. 44103.

2. Ferrer, M., et al., Metagenomics for mining new genetic resources of microbial communities. J Mol Microbiol Biotechnol, 2009. 16(1-2): p. 109-23.

3. Bellin, D. L., et al., Integrated circuit-based electrochemical sensor for spatially resolved detection of redox-active metabolites in biofilms. Nat Commun, 2014. 5: p. 3256.

4. Fei, Y., et al., Screening small-molecule compound microarrays for protein ligands without fluorescence labeling with a high-throughput scanning microscope. J Biomed Opt, 2010. 15(1): p. 016018.

5. Woronoff, G., et al., Activity-Fed Translation (AFT) Assay: A New High-Throughput Screening Strategy for Enzymes in Droplets. Chembiochem, 2015. 16(9): p. 1343-9.

6. Uchiyama, T., et al., Substrate-induced gene-expression screening of environmental metagenome libraries for isolation of catabolic genes. Nat Biotechnol, 2005. 23(1): p. 88-93.

7. van der Helm, E., H. J. Genee, and M.O.J.N.c.b. Sommer, The evolving interface between synthetic biology and functional metagenomics. 2018: p. 1.

8. Roelofs, K. G., et al., Differential radial capillary action of ligand assay for high-throughput detection of protein-metabolite interactions. Proceedings of the National Academy of Sciences, 2011. 108(37): p. 15528-15533.

9. Ferrer, M., et al., Interplay of metagenomics and in vitro compartmentalization. 2009. 2(1): p. 31-39.

10. Hosokawa, M., et al., Droplet-based microfluidics for high-throughput screening of a metagenomic library for isolation of microbial enzymes. 2015. 67: p. 379-385.

11. Kintses, B., et al., Picoliter cell lysate assays in microfluidic droplet compartments for directed enzyme evolution. 2012. 19(8): p. 1001-1009.

12. Choi, S.-L., et al., Toward a generalized and high-throughput enzyme screening system based on artificial genetic circuits. 2013. 3(3): p. 163-171.

13. Daniel, R. J. D. M. E. o. P. o. H. t. I. E. f. B., Construction of environmental libraries for functional screening of enzyme activity. 2002: p. 63-78.

14. majs, D., S. J. Norris, and G. M. Weinstock, Construction of small genome BAC library for functional and genomic applications, in Bacterial Artificial Chromosomes. 2004, Springer. p. 47-56.

15. Lam, S. S., et al., Directed evolution of APEX2 for electron microscopy and proximity labeling. 2015. Nat Methods. 2015 January; 12(1): 51-54.

The invention claimed is:

1. A method to identify a microbial redox enzyme (MRE) specific to a target analyte, the method comprising:
   a. preparing a genomic DNA (gDNA) library from a sample containing microbes, wherein the microbes contained in the sample comprise gDNA encoding at least one MRE;
   b. constructing an expression vector library comprising in an expression vector the gDNA library and a nucleic acid sequence encoding a readout enzyme (ReadE);
   c. contacting the expression vector library with a target analyte and at least one readout substrate (ReadS), wherein the target analyte is catalyzed by at least one MRE to produce $H_2O_2$, and
   wherein the ReadS can be converted to a readout product (ReadP) in the presence of hydrogen peroxide, wherein the ReadP produces a detectable signal;
   d. measuring the presence of the detectable signal produced by the ReadP; and
   e. identifying the MRE by sequencing the gDNA fragment identified by the detectable signal.

2. The method of claim 1, wherein the ReadE catalyzes the conversion of the ReadS to ReadP only in the presence of $H_2O_2$.

3. The method of claim 1, wherein the microbes contained in the sample comprise a genomic DNA (gDNA) encoding a plurality of MREs.

4. The method of claim 1, wherein the sample comprising at least one MRE is obtained from protein synthesis of a genomic DNA (gDNA) library encoding a plurality of MRE, where protein synthesis occurs in a cell-free manner.

5. The method of claim 2, wherein the readout enzyme is a peroxidase.

6. The method of claim 5, wherein the peroxidase is APEX2 or HRP.

7. The method of claim 1, wherein the readout substrate is a hydrogen peroxide responsive probe, wherein the hydrogen peroxide responsive probe produces a detectable signal in the presence of hydrogen peroxide.

8. The method of claim 7, wherein the detectable signal is selected from the group consisting of: fluorescence, bioluminescence, chemiluminescence, optical signal, and electrochemical signal.

9. The method of claim 7, wherein the hydrogen peroxide responsive probe produces an electrochemical signal, wherein the electrochemical signal is detected by current passed to an electrode.

10. The method of claim 1, wherein the detectable signal is fluorescence.

11. The method of claim 10, wherein the fluorescence is measured by FACS.

12. The method of claim 2, wherein the Readout Enzyme is APEX2, HRP, or a functional variant thereof, and the readout substrate is Amplex™ UltraRed (AUR).

13. The method of claim 7, wherein the hydrogen peroxide responsive probe is a boronate-based probe.

14. The method of claim 13, wherein the boronate-based probe is selected from the group consisting of: PY1, PO1, Hamovanillic Acid (HVA), Luminol, OPD, DCFH, ABTS, K iodine, or ABTS, 1a and 1b, PG1, PF1, PF3, PE1, RPF1, PC1, PY1-ME, PCL-1, and Fl-B.

15. The method of claim 7, wherein the hydrogen peroxide responsive probe is a non-boronate-based probe.

16. The method of claim 1, wherein the sample containing microbes is from any environmental source.

17. The method of claim 16, wherein the environmental source is selected from the group consisting of: water, soil, microbiome, feces, urine, plant sources, fungal cells, fossil energy source, Artic ice samples, Antarctic ice samples, water or permafrost sources, materials of volcanic origin, materials from soil or plant sources in tropical areas, oil samples, wastewater samples, a deep water, contaminated water, waste water source and any environmental source comprising microbes.

18. The method of claim 1, wherein the method is performed in a high-throughput manner on a microfluidic device.

19. The method of claim 1, wherein the target analyte is selected from the group consisting of a small molecule, toxin, neurotransmitter, steroid, immunomodulator, metabolite, and hormone.

20. The method of claim 19, wherein the hormone is selected from the group consisting of progesterone, estradiol, estrone, estriol, testosterone, aldosterone, prednisolone, androstadienone, cortisol, and cholesterol.

21. The method of claim 1, wherein the MRE is an oxidase or a dehydrogenase.

* * * * *